US012612383B2

(12) United States Patent
Yu

(10) Patent No.: US 12,612,383 B2
(45) Date of Patent: Apr. 28, 2026

(54) POLYSUBSTITUTED PYRROLIDINE DERIVATIVE, PREPARATION METHOD THEREFOR AND USE THEREOF

(71) Applicant: SHANGHAI WENNAI THERAPEUTICS CO., LTD., Shanghai (CN)

(72) Inventor: Shanghai Yu, Shanghai (CN)

(73) Assignee: SHANGHAI WENNAI THERAPEUTICS CO., LTD., Shanghai (CN)

( * ) Notice: Subject to any disclaimer, the term of this patent is extended or adjusted under 35 U.S.C. 154(b) by 0 days.

(21) Appl. No.: 19/190,493

(22) Filed: Apr. 25, 2025

(65) Prior Publication Data

US 2025/0296922 A1 Sep. 25, 2025

Related U.S. Application Data

(63) Continuation of application No. PCT/CN2024/107303, filed on Jul. 24, 2024.

(30) Foreign Application Priority Data

Jul. 26, 2023 (CN) ......................... 202310925595.0
Oct. 18, 2023 (CN) ......................... 202311351390.2
Nov. 17, 2023 (CN) ......................... 202311541338.3

(51) Int. Cl.
*C07D 401/12* (2006.01)
*A61K 31/4155* (2006.01)
(Continued)

(52) U.S. Cl.
CPC ........ *C07D 401/12* (2013.01); *A61K 31/4155* (2013.01); *A61K 31/4439* (2013.01);
(Continued)

(58) Field of Classification Search
CPC .. C07D 401/12; C07D 207/16; C07D 401/14; C07D 403/12; C07D 207/02;
(Continued)

(56) References Cited

U.S. PATENT DOCUMENTS 10,647,661 B2 5/2020 Ahmad et al.
11,834,441 B2 12/2023 Durrant et al.
(Continued)

FOREIGN PATENT DOCUMENTS

CN 111065383 A 4/2020
CN 113272293 A 8/2021
(Continued)

OTHER PUBLICATIONS

Haberson et al., Deuterium Medicinal Chemistry: A New Approach to Drug Discovery and Development, Medchem News, 8-22, No. 2, May 2014 (Year: 2014).*
(Continued)

*Primary Examiner* — Kortney L. Klinkel
*Assistant Examiner* — Padmaja S Rao
(74) *Attorney, Agent, or Firm* — Wilson Sonsini Goodrich & Rosati

(57) ABSTRACT

The present invention discloses a kind of polysubstituted pyrrolidine derivative compounds represented by the formula (I), stereoisomers, tautomers, deutero-derivatives or pharmaceutically acceptable salts thereof, as well as preparation methods and uses of the compounds and pharmaceutical compositions comprising the compounds, stereoisomers, tautomers, deutero-derivatives or pharmaceutically acceptable salts thereof, wherein the compounds can be used as sodium channel subtype Nav1.8 inhibitors, and their pharmaceutical use in the treatment and prevention of pain-related disorders.

(Continued)

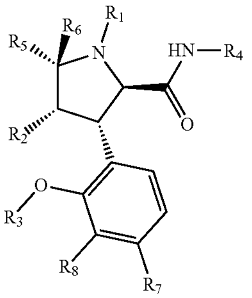

formula (I)

8 Claims, 1 Drawing Sheet

(51) Int. Cl.

| | |
|---|---|
| ***A61K 31/4439*** | (2006.01) |
| ***A61K 31/496*** | (2006.01) |
| ***C07B 59/00*** | (2006.01) |
| ***C07D 207/16*** | (2006.01) |
| ***C07D 401/14*** | (2006.01) |
| ***C07D 403/12*** | (2006.01) |

(52) U.S. Cl.
CPC .......... *A61K 31/496* (2013.01); *C07B 59/002* (2013.01); *C07D 207/16* (2013.01); *C07D 401/14* (2013.01); *C07D 403/12* (2013.01)

(58) Field of Classification Search
CPC ........................... C07D 207/04; C07D 295/04; C07D 295/195; C07D 405/12; C07D 405/14; C07D 413/14; C07B 59/002; A61K 31/4155; A61K 31/4439; A61K 31/496; A61K 31/395; A61K 31/40; A61P 25/04; A61P 29/00
See application file for complete search history.

(56) References Cited

U.S. PATENT DOCUMENTS

| | | | |
|---|---|---|---|
| 12,195,445 | B2 | 1/2025 | Arasappan et al. |
| 2007/0185056 | A1 | 8/2007 | Duan et al. |

FOREIGN PATENT DOCUMENTS

| | | | | |
|---|---|---|---|---|
| CN | 114945566 A | | 8/2022 | |
| WO | 2021113627 A1 | | 6/2021 | |
| WO | 2022256622 A1 | | 12/2022 | |
| WO | 2022256676 A1 | | 12/2022 | |
| WO | 2022256679 A1 | | 12/2022 | |
| WO | 2022256702 A1 | | 12/2022 | |
| WO | 2022256842 A1 | | 12/2022 | |
| WO | WO-2024046253 A1 | * | 3/2024 | ........... A61K 31/341 |

OTHER PUBLICATIONS

Wermuth, Molecular variations based in isosteric replacements, The Practice of Medicinal Chemistry, 203-237, 1996 (Year: 1996).*

* cited by examiner

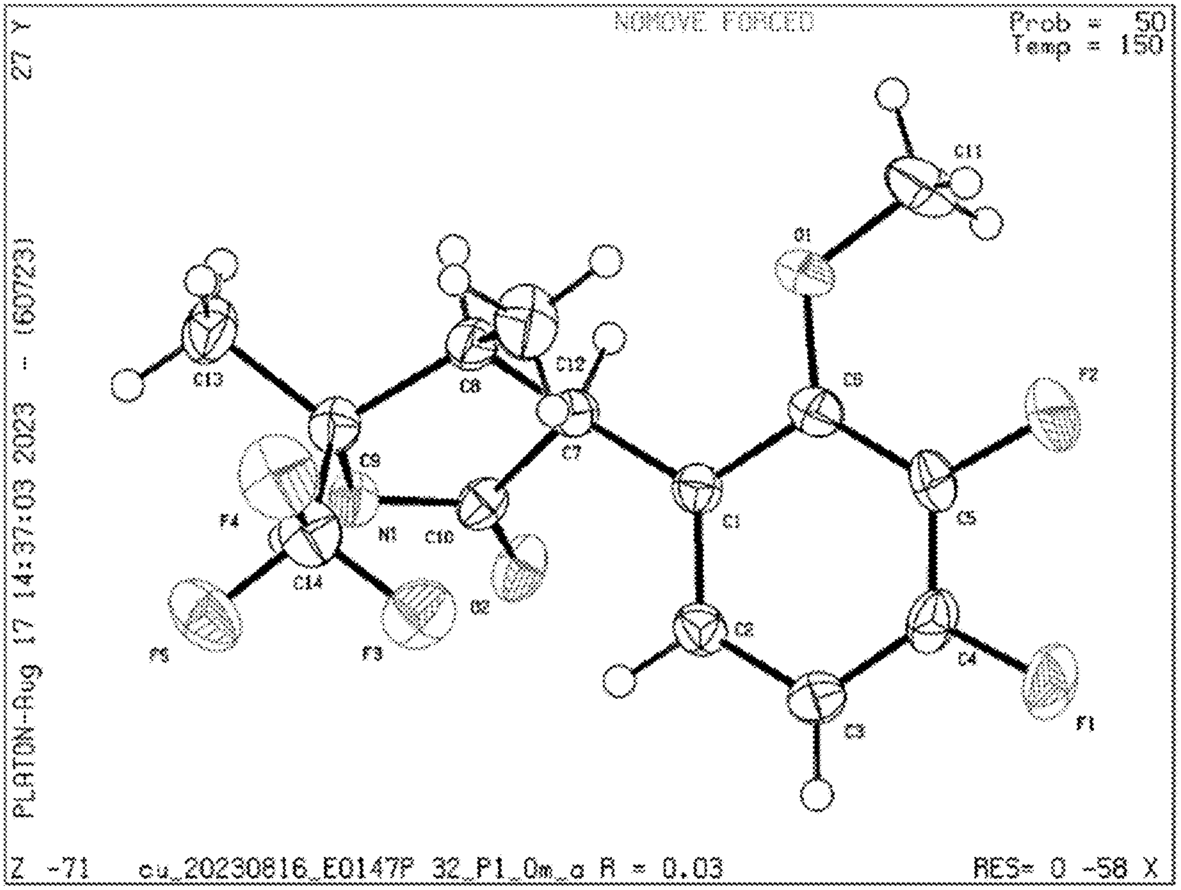
NOMOVE FORCED
Prob = 50
Temp = 150
27 Y
PLATON-Aug 17 14:37:03 2023 - (60723)
Z -71 cu_20230816_E0147P 32_P1_0m_a R = 0.03
RES= 0 -58 X

POLYSUBSTITUTED PYRROLIDINE DERIVATIVE, PREPARATION METHOD THEREFOR AND USE THEREOF

CROSS-REFERENCE TO RELATED APPLICATIONS

The present application is a continuation of International Patent Application No. PCT/CN2024/107303, filed 24 Jul. 2024 and entitled "Polysubstituted pyrrolidine derivatives, preparation methods and uses thereof," which claims priority to and benefit of Chinese Patent Application No. 202310925595.0, filed 26 Jul. 2023 and entitled "Polysubstituted pyrrolidine derivatives, preparation methods and uses thereof," Chinese Patent Application No. 202311351390.2, filed 18 Oct. 2023 and entitled "Polysubstituted pyrrolidine derivatives, preparation methods and uses thereof," and Chinese Patent Application No. 202311541338.3, filed 17 Nov. 2023 and entitled "Polysubstituted pyrrolidine derivatives, preparation methods and uses thereof," the entire contents of each of which applications are incorporated herein by reference for all purposes.

TECHNICAL FIELD

The present invention relates to the field of drug synthesis, and more specifically to a polysubstituted pyrrolidine derivative, a stereoisomer, a tautomer, a deuterated derivative or a pharmaceutically acceptable salt thereof, as well as preparation methods and uses of the compounds, and pharmaceutical compositions comprising such compounds, stereoisomers, tautomers, deuterated derivative or pharmaceutically acceptable salts thereof, wherein the compounds can be used as sodium channel subtype Nav1.8 inhibitors, and their pharmaceutical use in the treatment and prevention of pain-related disorders.

TECHNICAL BACKGROUND

Pain is one of the most common clinical conditions. The National Institutes of Health (NIH) estimates that 100 million people in the United States suffer from chronic pain, and the annual global healthcare costs for pain management have reached $75 billion. In China, more than 300 million people suffer from chronic pain, and the number is increasing by 20 million per year. Currently, commonly used analgesic drugs are mainly non-steroidal anti-inflammatory drugs (NSAIDs) and opioid analgesics. The analgesic effect of NSAIDs is weak and there is a ceiling effect. Opioid analgesics are commonly associated with constipation, respiratory depression, and addiction, as well as serious drug abuse. There is a huge unmet clinical need in the analgesic market.

Pain is an important protective mechanism of a healthy organism against further injury of tissues. However, the organism sometimes suffers from useless, long-standing chronic, pathological pain, such as neuropathic pain, at the same time. The main causes of neuropathic pain include physical mechanical damage to neurons, metabolic or trophic neurological changes, structural abnormalities of neurons, neurotransmitter dysfunction, etc. Herpes, diabetes, and medications can sometimes induce metabolic or trophic neurological changes.

An organism perceives pain as a process in which injurious stimuli are generated and transmitted between neurons, and sodium channel activity is an important factor in the transmission of excitatory stimuli by neurons. Voltage gated sodium channels (VGSCs) are multisubunit transmembrane glycoproteins expressed on the cell membrane, consisting of α-subunit (functional unit) and β-subunit. Based on different α subunits, they are divided into 9 subtypes, i.e., the 9 members of sodium channel type 1 (Nav1)-Nav1.1~1.9. The a subunit of Nav1 consists of 4 homologous transmembrane structural domains (I~IV), each of which contains 6 transmembrane hydrophobic a helices (S1-S6), the positively charged S4 fragment has the function of a voltage receptor, and is able to modulate the hydrophilic pore between S5 and S6 that allows the passage of sodium ions, causing cellular depolarization or hyperpolarization, and completing the transmembrane transmission of signals. When a neuron is stimulated, the Nav1 channel turns on, allowing positively charged sodium ions to pass across the cell membrane into a previously negatively charged cell. The change in charge on the cell membrane produces an electric current that increases the excitability of the neuron and initiates the downstream signal transmission resulting pain.

Different subtypes of Nav1 are expressed in different tissues and are involved in different types of nociceptive transmission. For example, some are expressed only in peripheral neurons, while others mediate signal transmission in both central and peripheral neurons. According to the classification of channel sensitivity to tetrodotoxin (TTX), Nav1.1-1.4, Nav1.6 and Nav1.7 are TTX-sensitive channels (TTX-S), and Nav1.5, Nav1.8 and Nav1.9 are TTX-resistant channels (TTX-R). Studies show that broad-spectrum sodium channel blockers will produce severe side effects after blocking Nav1.4 associated with skeletal muscle and Nav1.5 associated with cardiac muscle, so designing selective blockers for specific Nav channels is the direction of pain drug development. As an important ion channel in nociceptors, Nav1.8 is distributed only in peripheral neurons and plays a key role in nociceptive signal transduction in the peripheral nervous system, and is a major causative factor involved in neuropathic pain, chronic itch, inflammatory pain, atrial fibrillation and Brugada syndrome. In currently available technology, such as WO2021113627A1, WO2022256622A1, WO2022256676A1, WO2022256679A1, WO2022256702A1, and WO2022256842A1, inhibitors targeting Nav1.8 are furan derivatives. Currently there are no specific pain drugs targeting Nav1.8 subtype on the market globally, and clinical studies have demonstrated that Nav1.8 selective blockers have good neuropathic pain inhibition, so the design of highly active and specific Nav1.8 inhibitors is expected to provide efficient therapeutic options in the field of pain.

SUMMARY OF THE INVENTION

According to an aspect of the present invention, an object of the present invention is to provide a kind of compounds represented by the formula (I), stereoisomers, tautomers, deuterated derivatives or pharmaceutically acceptable salts thereof:

formula (I)

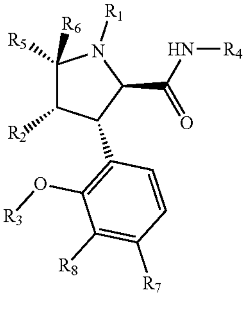

wherein $R_1$ is selected from the group consisting of hydrogen atom, $C_{1-15}$ alkyl, $C_{1-15}$ alkoxy, $C_{1-15}$ alkylcarbonyl, $C_{3-15}$ cycloalkyl, and four- to eight-membered heterocyclyl containing 1 to 3 heteroatoms selected from N, O and S, wherein the $C_{1-15}$ alkyl, $C_{1-15}$ alkoxy, $C_{1-15}$ alkylcarbonyl, $C_{3-15}$ cycloalkyl, four- to eight-membered heterocyclyl containing 1 to 3 heteroatoms selected from N, O and S may be substituted with one or more $R_a$ substituents, the $R_a$ is selected from the group consisting of hydrogen atom, $C_{1-6}$ alkyl, $C_{1-6}$ alkoxy, $C_{3-6}$ cycloalkyl, halogen atom, amino, hydroxyl, and amide;

$R_2$ is selected from the group consisting of hydrogen atom, $C_{1-8}$ alkyl, $C_{1-8}$ alkoxy, deutero-$C_{1-8}$ alkyl, halo-$C_{1-8}$ alkyl, halo-$C_{1-8}$ alkoxy, and $C_{3-6}$ cycloalkyl;

$R_3$ is selected from the group consisting of hydrogen atom, $C_{1-8}$ alkyl, deutero-$C_{1-8}$ alkyl, halo-$C_{1-8}$ alkyl, $C_{3-6}$ cycloalkyl, and three- to eight-membered heterocyclyl containing 1 to 3 heteroatoms selected from N, O and S;

$R_4$ is selected from the group consisting of $C_{6-14}$ aryl, five- to eight-membered heteroaryl containing 1 to 3 heteroatoms selected from N, O and S, five- to eight-membered heteroaryl oxide containing 1 to 3 heteroatoms selected from N, O and S, wherein the $C_{6-14}$ aryl, five- to eight-membered heteroaryl containing 1 to 3 heteroatoms selected from N, O and S may be substituted with one or more $R_b$ substituents, wherein the $R_b$ is selected from the group consisting of hydrogen atom, $C_{1-6}$ alkyl, $C_{3-6}$ cycloalkyl, halogen atom, nitro, amino, hydroxyl, carbonyl, cyano, formamido, oxyl, sulfonamido, aza-hydroxyformamidinyl, aza-hydroxyamidino, $C_{1-6}$ alkyl substituted by 1 to 3 halogen atoms, $C_{3-6}$ cycloalkyl substituted by 1 to 3 halogen atoms, $C_1$. 6 alkyl substituted by 1 to 3 hydroxyl, $C_{3-6}$ cycloalkyl substituted by 1 to 3 hydroxyl, and four- to six-membered heterocyclyl containing 1 to 3 heteroatoms selected from N, O and S and unsubstituted or substituted by 1 to 3 $C_{1-6}$ alkyl;

$R_5$ is selected from the group consisting of $C_{1-6}$ alkyl, halo-$C_{1-6}$ alkyl, and $C_{3-6}$ cycloalkyl;

$R_6$ is selected from the group consisting of hydrogen atom, $C_{1-6}$ alkyl, halo-$C_{1-6}$ alkyl, and $C_{3-6}$ cycloalkyl;

$R_7$ is selected from the group consisting of hydrogen atom, $C_{1-6}$ alkyl, halo-$C_{1-6}$ alkyl, $C_{1-6}$ alkoxy, halo-$C_{1-6}$ alkoxy, $C_{3-6}$ cycloalkyl, halogen atom, cyano, and amide;

$R_8$ is selected from the group consisting of hydrogen atom, $C_{1-6}$ alkyl, halo-$C_{1-6}$ alkyl, halogen atom, and cyano.

Preferably, $R_1$ is selected from the group consisting of hydrogen atom, $C_{1-6}$ alkyl, $C_{1-6}$ alkoxy, $C_{1-6}$ alkylcarbonyl, $C_{3-8}$ cycloalkyl, and four- to six-membered heterocyclyl containing 1 to 3 heteroatoms selected from N, O, and S, wherein the $C_{1-6}$ alkyl, $C_{1-6}$ alkoxy, $C_{1-6}$ alkylcarbonyl, $C_{3-8}$ cycloalkyl, four- to six-membered heterocyclyl containing 1 to 3 heteroatoms selected from N, O and S may be substituted with 1 to 3 $R_a$ substituents, the $R_a$ is selected from the group consisting of hydrogen atom, $C_{1-4}$ alkyl, $C_{1-4}$ alkoxy, $C_{3-6}$ cycloalkyl, halogen atom, amino, hydroxyl, and amide.

Preferably, $R_1$ is selected from the group consisting of hydrogen atom, $C_{1-4}$ alkyl, $C_{1-4}$ alkoxy, $C_{1-4}$ alkylcarbonyl, $C_{3-6}$ cycloalkyl, and four- to six-membered heterocyclyl containing 1 or 2 heteroatoms selected from N, O and S, wherein the $C_{1-4}$ alkyl, $C_{1-4}$ alkoxy, $C_{1-4}$ alkylcarbonyl, $C_{3-6}$ cycloalkyl, four- to six-membered heterocyclyl containing 1 or 2 heteroatoms selected from N, O and S may be substituted with 1 to 3 $R_a$ substituents, the $R_a$ is selected from the group consisting of hydrogen atom, $C_{1-4}$ alkyl, $C_{1-4}$ alkoxy, $C_{3-6}$ cycloalkyl, halogen atom, amino, hydroxyl, and amide.

Preferably, $R_1$ is selected from the group consisting of hydrogen atom, methyl, trifluoroacetyl, ethyl, n-propyl, isopropyl, n-butyl, sec-butyl, tert-butyl, cyclopropyl, cyclobutyl, cyclopentyl, and cyclohexyl, wherein the above substituents may be substituted with 1 or 2 $R_a$ substituents, the $R_a$ is selected from the group consisting of hydrogen atom, methyl, ethyl, propyl, isopropyl, n-butyl, sec-butyl, tert-butyl, methoxy, ethoxy, propoxy, isopropoxy, n-butoxy, sec-butoxy, tert-butoxy, cyclopropyl, cyclobutyl, cyclopentyl, cyclohexyl, fluorine atom, chlorine atom, bromine atom, amino, hydroxy, and amide.

Preferably, $R_1$ is selected from the group consisting of hydrogen atom, methyl, trifluoroacetyl, ethyl, n-propyl, isopropyl, n-butyl, and cyclopropyl, wherein the above substituents may be substituted with 1 or 2 $R_a$ substituents, the $R_a$ is selected from the group consisting of hydrogen atom, methyl, methoxy, fluorine atom, chlorine atom, bromine atom, amino, hydroxy, cyano, and amide.

Preferably, $R_2$ is selected from the group consisting of hydrogen atom, $C_{1-6}$ alkyl, $C_{1-6}$ alkoxy, deutero-$C_{1-6}$ alkyl, halo-$C_{1-6}$ alkyl, halo-$C_{1-6}$ alkoxy, and $C_{3-6}$ cycloalkyl.

Preferably, $R_2$ is selected from the group consisting of hydrogen atom, $C_{1-4}$ alkyl, $C_{1-4}$ alkoxy, deutero-$C_{1-4}$ alkyl, halo-$C_{1-4}$ alkyl, halo-$C_{1-4}$ alkoxy, and $C_{3-6}$ cycloalkyl.

Preferably, $R_2$ is selected from the group consisting of hydrogen atom, methyl, ethyl, n-propyl, isopropyl, n-butyl, sec-butyl, tert-butyl, methoxy, ethoxy, n-propoxy, isopropoxy, n-butoxy, sec-butoxy, tert-butoxy, deuteromethyl, mono-fluoromethyl, difluoromethyl, trifluoromethyl, monofluoroethyl, difluoroethyl, trifluoroethyl, tetrafluoroethyl, pentafluoroethyl, difluoropropyl, trifluoropropyl, tetrafluoropropyl, pentafluoropropyl, hexafluoropropyl, perfluoropropyl, cyclopropyl, cyclobutyl, cyclopentyl, and cyclohexyl.

Preferably, $R_3$ is selected from the group consisting of hydrogen atom, $C_{1-6}$ alkyl, deutero-$C_{1-6}$ alkyl, halo-$C_{1-6}$ alkyl, $C_{3-6}$ cycloalkyl, and three- to six-membered heterocyclyl containing 1 to 3 heteroatoms selected from N, O and S.

Preferably, $R_3$ is selected from the group consisting of hydrogen atom, $C_{1-4}$ alkyl, deutero-$C_{1-4}$ alkyl, halo-$C_{1-4}$ alkyl, $C_{3-6}$ cycloalkyl, and three- to six-membered heterocyclyl containing 1 or 2 heteroatoms selected from N and O.

Preferably, $R_3$ is selected from the group consisting of hydrogen atom, methyl, ethyl, n-propyl, isopropyl, n-butyl, sec-butyl, tert-butyl, deuteromethyl, monofluoromethyl, difluoromethyl, trifluoromethyl, monofluoroethyl, difluoroethyl, trifluoroethyl, tetrafluoroethyl, pentafluoroethyl, difluoropropyl, trifluoropropyl, tetrafluoropropyl, pentafluoropropyl, hexafluoropropyl, perfluoropropyl, cyclopropyl, cyclobutyl, cyclopentyl, and cyclohexyl.

Preferably, $R_4$ is selected from the group consisting of $C_{6-10}$ aryl, five- to six-membered heteroaryl containing 1 to 3 heteroatoms selected from N and O, and five- to six-membered heteroaryl oxide containing 1 to 3 heteroatoms selected from N, O and S, wherein the $C_{6-10}$ aryl, five- to six-membered heteroaryl containing 1 to 3 heteroatoms selected from N and 0, five- to six-membered heteroaryl oxide containing 1 to 3 heteroatoms selected from N, O and S may be substituted with one or more $R_b$ substituents, wherein the $R_b$ is selected from the group consisting of hydrogen atom, $C_{1-4}$ alkyl, $C_{3-6}$ cycloalkyl, halogen atom, nitro, amino, hydroxy, carbonyl, cyano, formamido, oxyl, sulfonamido, aza-hydroxyformamidino, aza-hydroxyamidinyl, $C_{1-4}$ alkyl substituted by 1 to 3 halogen atoms, $C_{3-6}$ cycloalkyl substituted by 1 to 3 halogen atoms, $C_{1-4}$ alkyl substituted by 1 to 2 hydroxyl, $C_{3-6}$ cycloalkyl substituted by 1 to 2 hydroxyl, and four- to six-membered heterocyclyl containing 1 or 2 heteroatoms selected from N or O and unsubstituted or substituted by 1 to 3 $C_{1-4}$ alkyl.

Preferably, $R_4$ is selected from the group consisting of phenyl, naphthyl, anthracenyl, furanyl, thienyl, pyrrolyl, pyrazolyl, oxazolyl, isoxazolyl, isothiazolyl, imidazolyl, thiazolyl, pyridinyl, pyridazinyl, pyrimidinyl, pyrazinyl, indolyl, quinolinyl, isoquinolinyl, pyridinyl oxide, imidazolyl oxide, pyrrolyl oxide, pyrazolyl oxide, oxazolyl oxide, isoxazolyl oxide, isothiazolyl oxide, thiazolyl oxide, pyridazinyl oxide, pyrimidinyl oxide, pyrazinyl oxide, indolyl oxide, quinolinyl oxide, and isoquinolinyl oxide, wherein the above substituents may be substituted with one or more $R_b$ substituents, wherein the $R_b$ is selected from the group consisting of hydrogen atom, $C_{1-4}$ alkyl, $C_{3-6}$ cycloalkyl, halogen atom, amino, carbonyl, hydroxyl, cyano, formamido, oxyl, sulfonamido, aza-hydroxyformamidinyl, aza-hydroxyamidinyl, $C_{1-4}$ alkyl substituted with 1 to 3 halogen atoms, $C_{3-6}$ cycloalkyl substituted with 1 to 3 halogen atoms, $C_{1-4}$ alkyl substituted with 1 to 3 hydroxyl, $C_{3-6}$ cycloalkyl substituted with 1 to 3 hydroxyl, and four-to six-membered heterocyclyl containing 1 to 3 heteroatoms selected from N, O, and S to and unsubstituted or substituted with 1 to 3 $C_{1-4}$ alkyl.

Preferably, $R_5$ is selected from the group consisting of $C_{1-4}$ alkyl, halo-$C_{1-4}$ alkyl, and $C_{3-6}$ cycloalkyl.

Preferably, $R_5$ is selected from the group consisting of methyl, ethyl, n-propyl, isopropyl, n-butyl, sec-butyl, tert-butyl, cyclopropyl, cyclobutyl, cyclopentyl, cyclohexyl, monofluoromethyl, difluoromethyl, trifluoromethyl, monofluoroethyl, difluoroethyl, trifluoroethyl, tetrafluoroethyl, pentafluoroethyl, difluoropropyl, trifluoropropyl, tetrafluoropropyl, pentafluoropropyl, hexafluoropropyl, and perfluoropropyl.

Preferably, $R_5$ is selected from the group consisting of methyl, ethyl, n-propyl, isopropyl, n-butyl, sec-butyl, tert-butyl, and trifluoromethyl.

Preferably, $R_6$ is selected from the group consisting of $C_{1-4}$ alkyl, halo-$C_{1-4}$ alkyl, and $C_{3-6}$ cycloalkyl.

Preferably, $R_6$ is selected from the group consisting of methyl, ethyl, n-propyl, isopropyl, n-butyl, sec-butyl, tert-butyl, cyclopropyl, cyclobutyl, cyclopentyl, cyclohexyl, monofluoromethyl, difluoromethyl, trifluoromethyl, monofluoroethyl, difluoroethyl, trifluoroethyl, tetrafluoroethyl, pentafluoroethyl, difluoropropyl, trifluoropropyl, tetrafluoropropyl, pentafluoropropyl, hexafluoropropyl, and perfluoropropyl.

Preferably, $R_6$ is selected from the group consisting of hydrogen atom, methyl, ethyl, n-propyl, and isopropyl.

Preferably, $R_7$ is selected from the group consisting of $C_{1-4}$ alkyl, halo-$C_{1-4}$ alkyl, $C_{1-4}$ alkoxy, halo-$C_{1-4}$ alkoxy, $C_{3-6}$ cycloalkyl, halogen atom, cyano, and amido.

Preferably, $R_7$ is selected from the group consisting of halogen atom, methyl, ethyl, n-propyl, isopropyl, n-butyl, sec-butyl, tert-butyl, methoxy, ethoxy, n-propoxy, isopropoxy, n-butoxy, sec-butoxy, tert-butoxy, cyclopropyl, cyclobutyl, cyclopentyl, cyclohexyl, monofluoromethyl, difluoromethyl, trifluoromethyl, monofluoroethyl, difluoroethyl, trifluoroethyl, tetrafluoroethyl, pentafluoroethyl, monofluoromethoxy, difluoromethoxy, trifluoromethoxy, monofluoroethoxy, difluoroethoxy, trifluoroethoxy, tetrafluoroethoxy, and pentafluoroethoxy.

Preferably, $R_7$ is selected from the group consisting of hydrogen atom, methyl, isopropyl, cyclopropyl, cyclobutyl, fluorine atom, chlorine atom, bromine atom, methoxy, and trifluoromethoxy.

Preferably, $R_8$ is selected from the group consisting of hydrogen atom, $C_{1-4}$ alkyl, halo-$C_{1-4}$ alkyl, halogen atom, and cyano.

Preferably, $R_8$ is selected from the group consisting of hydrogen atom, halogen atom, methyl, ethyl, n-propyl, isopropyl, n-butyl, sec-butyl, tert-butyl, monofluoromethyl, difluoromethyl, trifluoromethyl, monofluoroethyl, difluoroethyl, trifluoroethyl, tetrafluoroethyl, and pentafluoroethyl.

Preferably, $R_8$ is selected from the group consisting of hydrogen atom, fluorine atom, chlorine atom, bromine atom, and methyl.

Preferably, the compounds represented by formula (I), stereoisomers, tautomers, deutero-derivatives or pharmaceutically acceptable salts thereof according to the present invention may be represented by the following formula (II):

Formula (II)

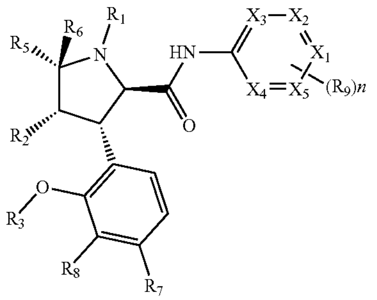

wherein the definition of $R_1$ to $R_8$ are as same as those in formula (I) respectively;

$X_1$ to $X_5$ are each independently CH, O or N or $N^+—O^-$, provided that at most three of $X_1$ to $X_5$ are N and the rest are C;

$R_9$ is selected from the group consisting of hydrogen atom, halogen atom, amino, hydroxyl, carbonyl, cyano, amido, oxo, sulfonamido, aza-hydroxyformamidine, aza-hydroxyamidinium, $C_{1-6}$ alkyl, $C_{3-8}$ cycloalkyl, $C_{6-14}$ aryl, four- to six-membered heterocyclyl containing 1 to 3 heteroatoms selected from N, O and S, five- to six-membered heteroaryl containing 1 to 3 heteroatoms selected from N, O and S, wherein the $C_{1-6}$ alkyl, $C_{3-8}$ cycloalkyl, $C_{6-14}$ aryl, four- to six-membered heterocyclyl containing 1 to 3 heteroatoms selected from N, O and S, and five- to six-membered heteroaryl containing 1 to 3 heteroatoms selected from N, O and S may be substituted with 1 to 3 $R_c$ substituents, wherein $R_c$ is selected from the group consisting of hydrogen atom, $C_{1-4}$ alkyl, $C_{3-6}$ cycloalkyl, halogen atom, nitro, amino, hydroxyl, cyano, formamido, oxyl, sulfonamido, aza-hydroxycarboxamido, and aza-hydroxyamidinamido;

n is an integer selected from 0, 1, 2, 3 or 4.

Preferably, $X_3$ and $X_4$ are CH or N.

Preferably, $X_1$, $X_2$ or $X_5$ is each independently selected from CH or N or $N^+—O^-$.

Preferably, $R_9$ is selected from the group consisting of hydrogen atom, halogen atom, amino, hydroxyl, carbonyl, cyano, formamido, oxyl, sulfonamido, aza-hydroxyformamidine, aza-hydroxyamidinium, $C_{1-6}$ alkyl, $C_{3-8}$ cycloalkyl, $C_{6-14}$ aryl, four- to six-membered heterocyclyl containing 1 to 3 heteroatoms selected from N, O, and S, and five- to six-membered heteroaryl containing 1 to 3 heteroatoms selected from N, O, and S atoms, wherein the $C_{1-6}$ alkyl, $C_{3-8}$ cycloalkyl, $C_{6-14}$ aryl, four- to six-membered heterocyclyl containing 1 to 3 heteroatoms selected from N, O and S, and five- to six-membered heteroaryl containing 1 to 3 heteroatoms selected from N, O and S may be substituted with 1 to 3 $R_c$ substituents, wherein $R_c$ is selected from the group consisting of hydrogen atom, $C_{1-4}$ alkyl, $C_{3-6}$ cycloalkyl, halogen atom, amino, hydroxyl, cyano, formamido, oxyl, sulfonamido, aza-hydroxycarboxamido, and aza-hydroxyamidinamido.

Preferably, $R_9$ is selected from the group consisting of hydrogen atom, halogen atom, amino, hydroxyl, carbonyl, cyano, formamido, oxyl, sulfonamido, aza-hydroxyformamidinyl, aza-hydroxyformamidinyl, $C_{1-4}$ alkyl, $C_{3-6}$ cycloalkyl, $C_{6-10}$ aryl, four- to six-membered heterocyclyl containing 1 to 3 heteroatoms selected from N, O, and S, and five- to six-membered heterocyclyl containing 1 to 3 heteroatoms selected from N, O and S atoms, wherein the $C_{1-4}$ alkyl, $C_{3-6}$ cycloalkyl, $C_{6-10}$ aryl, four- to six-membered heterocyclyl containing 1 to 3 heteroatoms selected from N, O and S, and five- to six-membered heteroaryl containing 1 to 3 heteroatoms selected from N, O and S may be substituted with 1 to 3 $R_c$ substituents, wherein the $R_c$ is selected from the group consisting of hydrogen atom, $C_{1-3}$ alkyl, $C_{3-6}$ cycloalkyl, halogen atom, amino, hydroxy, cyano, amido, oxo, sulfonamido, aza-hydroxycarboxamido, and aza-hydroxyamidinamido.

Preferably, $R_9$ is selected from the group consisting of hydrogen atom, halogen atom, amino, hydroxyl, carbonyl, cyano, formamido, oxyl, sulfonamido, aza-hydroxyformamidinyl, aza-hydroxyformamidinyl, $C_{1-4}$ alkyl, $C_{3-6}$ cycloalkyl, $C_{6-10}$ aryl, four- to six-membered heterocyclyl containing 1 or 2 heteroatoms selected from N and 0, and five- to six-membered heteroaryl containing 1 or 2 heteroatoms selected from N and 0, wherein $C_{1-4}$ alkyl, $C_{3-6}$ cycloalkyl, $C_{6-10}$ aryl, four- to six-membered heterocyclyl containing 1 or 2 heteroatoms selected from N and O, and five- to six-membered heteroaryl containing 1 or 2 heteroatoms selected from N and O may be substituted with 1 to 3 $R_c$ substituents, wherein $R_c$ is selected from the group consisting of hydrogen atom, $C_{1-3}$ alkyl, $C_{3-6}$ cycloalkyl, halogen atom, amino, hydroxy, cyano, formamido, oxyl, sulfonamido, aza-hydroxycarboxamido, and aza-hydroxyamidinamido.

Preferably, $R_9$ is selected from the group consisting of hydrogen atom, halogen atom, amino, hydroxyl, carbonyl, cyano, formamido, oxyl, sulfonamido, aza-hydroxyformamidinyl, aza-hydroxyformamidinyl, methyl, ethyl, n-propyl, isopropyl, n-butyl, sec-butyl, tert-butyl, cyclopropyl, cyclopentyl, cyclohexyl, phenyl

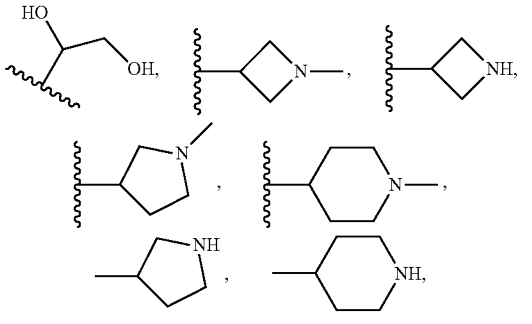

wherein the above substituents may be substituted with 1 or 2 $R_c$ substitutions, $R_c$ is selected from the group consisting of hydrogen atoms, methyl, ethyl, propyl, isopropyl, cyclopropyl, cyclobutyl, cyclopentyl, cyclohexyl, fluorine atom, chlorine atom, bromine atom, amino, hydroxyl, cyano, and formamido.

Preferably, n is an integer selected from 0, 1 or 2.

Preferably, n is an integer selected from 0 or 1.

Preferably, the compounds represented by formula (I), stereoisomers, tautomers, deutero-derivatives or pharmaceutically acceptable salts thereof according to the present invention may be represented by the following formula (III):

Formula (III)

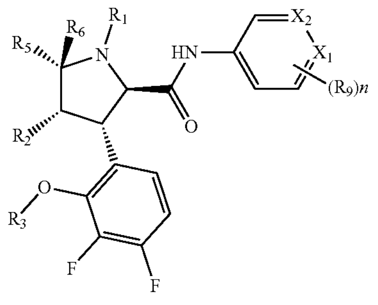

wherein the definitions of $R_1$, $R_2$, $R_3$, $R_5$, $R_6$ are as same as those in formula (I) respectively;

the definitions of $R_9$, $X_1$, $X_2$ are as same as those in formula (II) respectively.

Preferably, the compounds represented by formula (I), stereoisomers, tautomers, deutero-derivatives or pharmaceutically acceptable salts thereof according to the present invention may be represented by the following formula (IVa), formula (IVb), formula (IVc) or formula (IVd):

Formula (IVa)

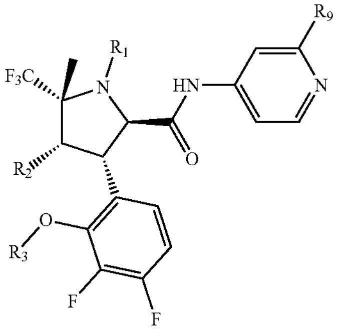

Formula (IVb)

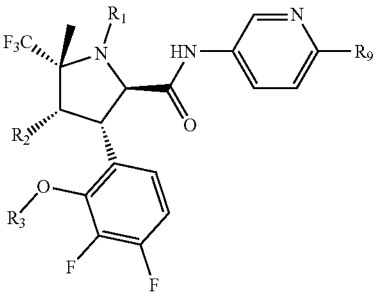

-continued

Formula (IVc)

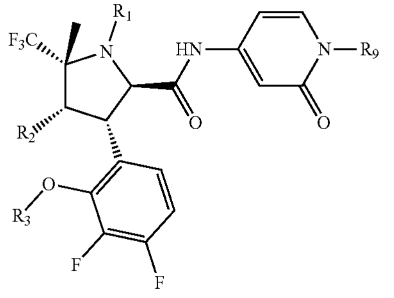

Formula (IVd)

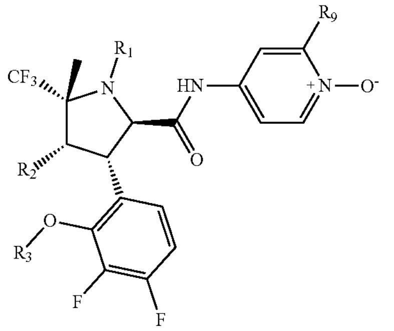

wherein the definitions of $R_1$, $R_2$, and $R_3$ are as same as those in formula (I) respectively; and the definitions of $R_5$ is as same as those in formula (II) respectively.

Preferably, the compounds represented by formula (I), stereoisomers, tautomers, deutero-derivatives or pharmaceutically acceptable salts thereof according to the present invention are selected from the following compounds:

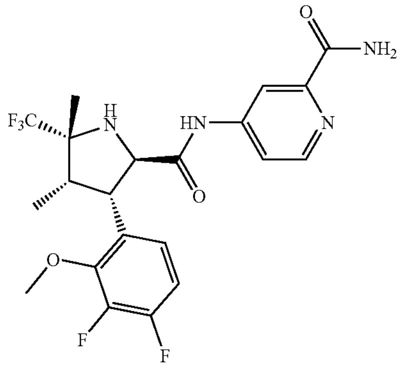

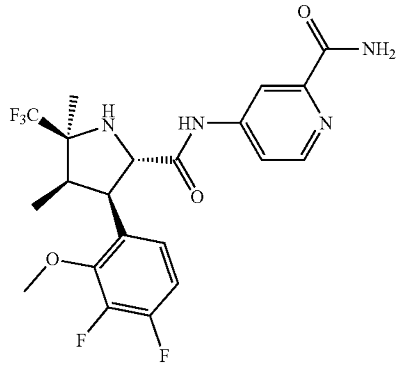

-continued

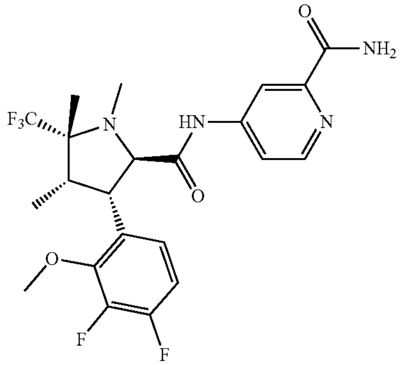

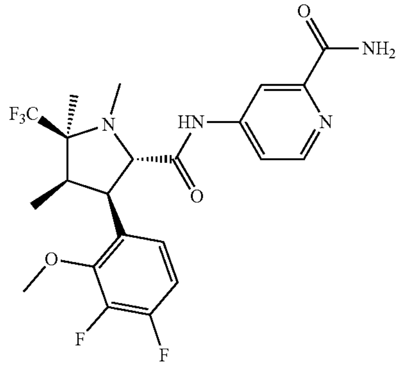

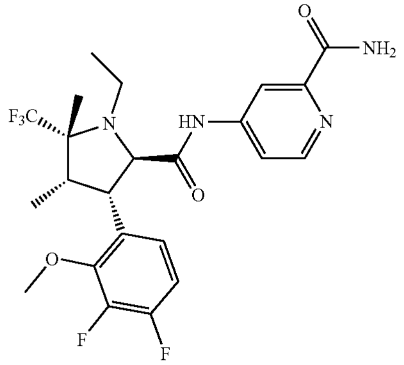

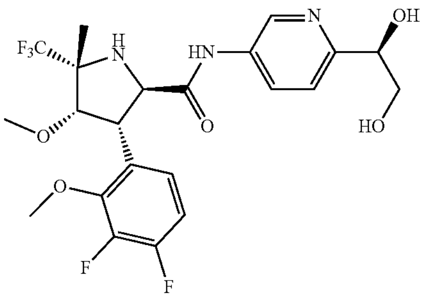

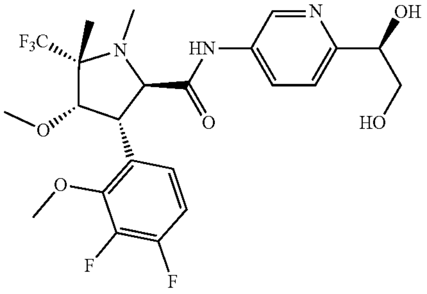

-continued
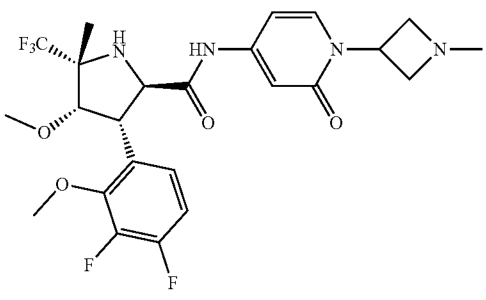
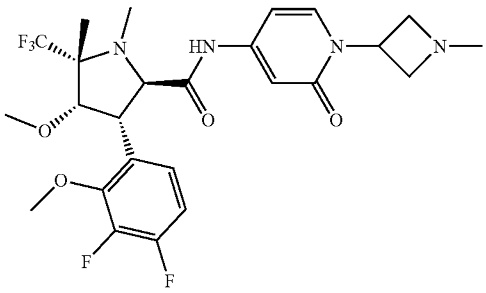
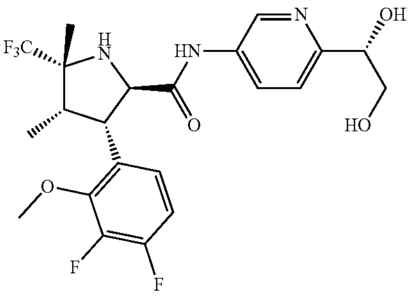
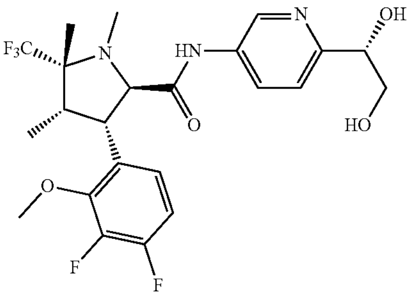
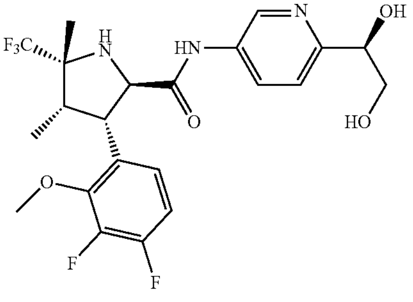
-continued
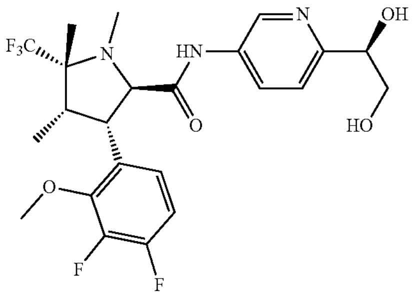
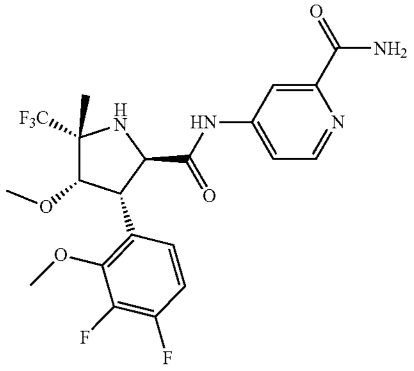
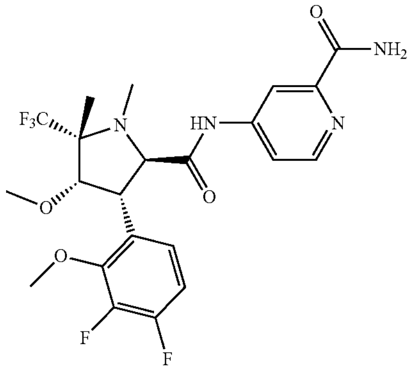
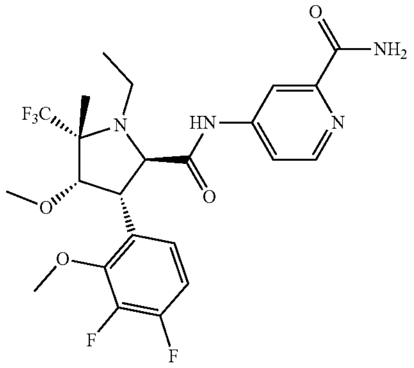
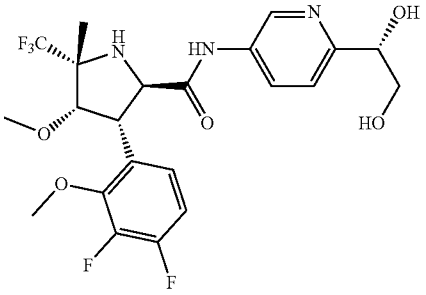

-continued
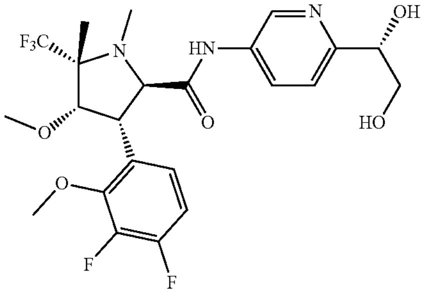
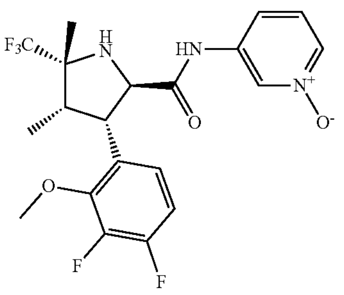
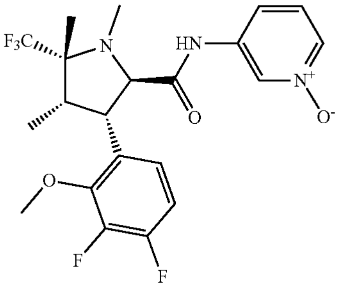
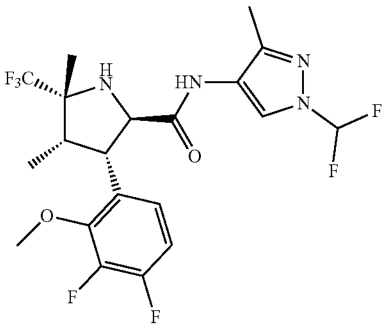
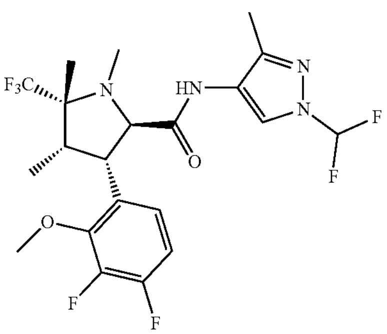
-continued
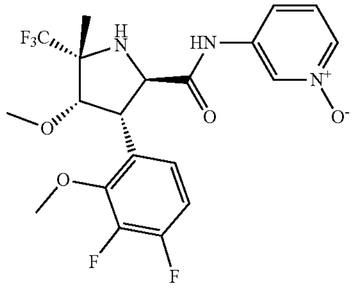
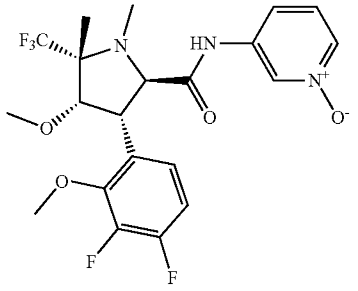
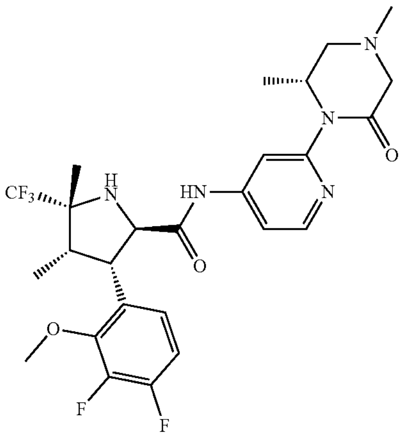
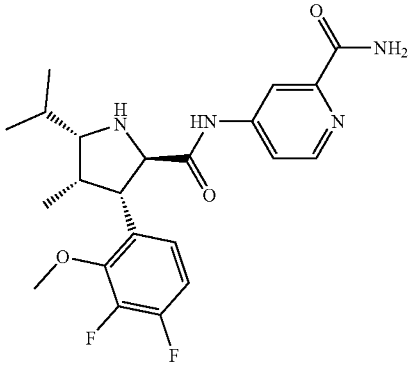

-continued
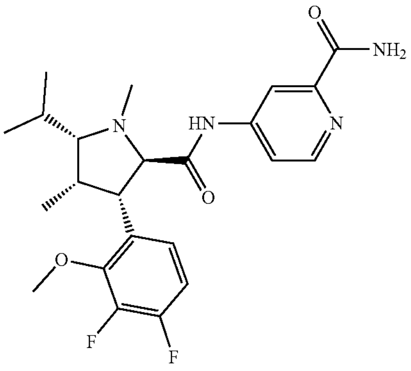
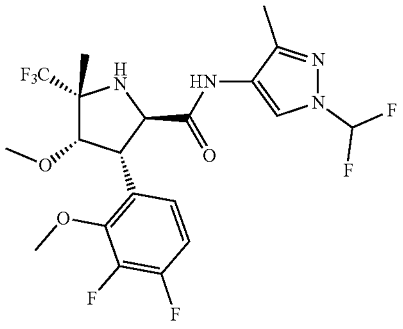
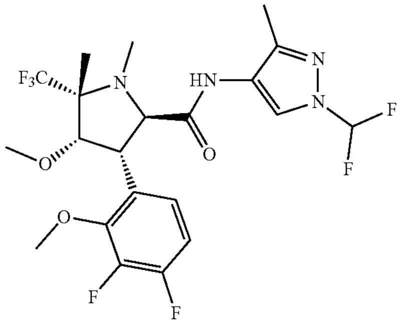
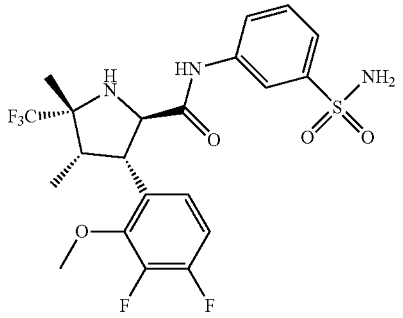
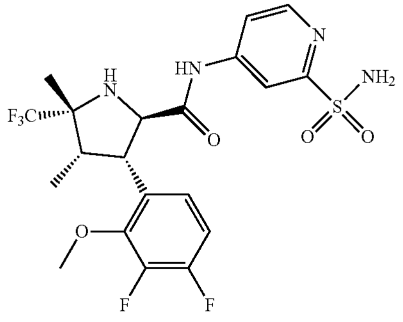
-continued
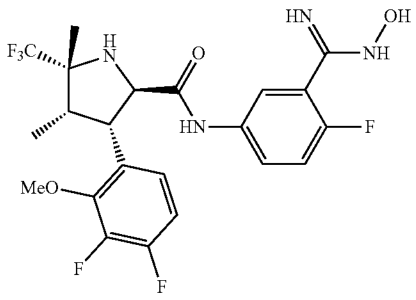
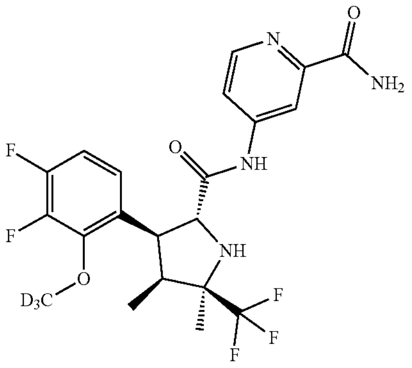
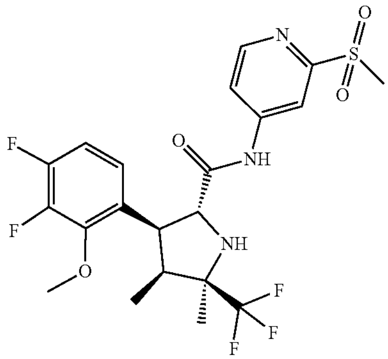
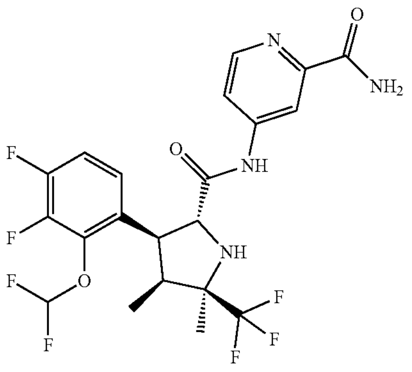
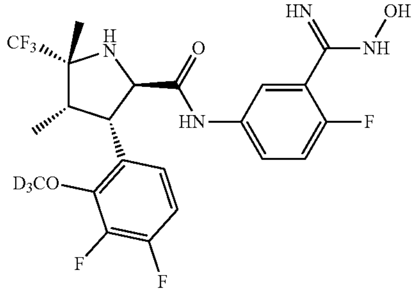

-continued
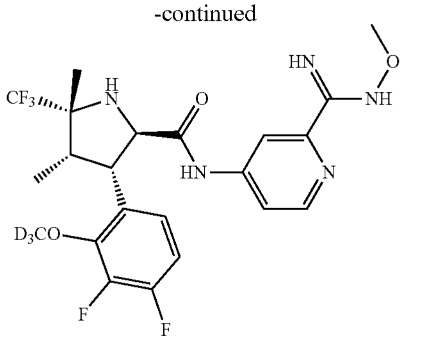
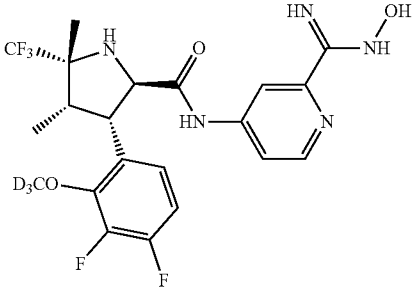
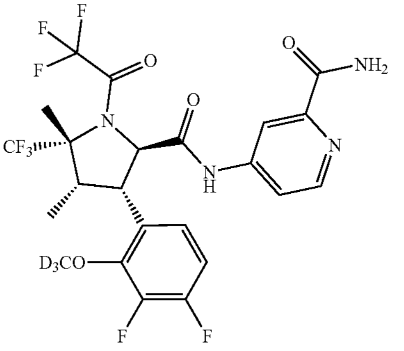
-continued
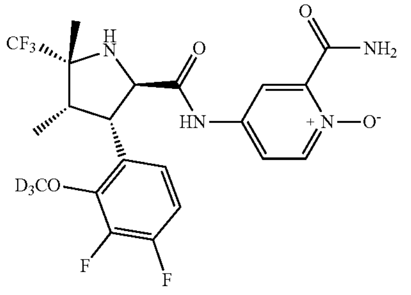
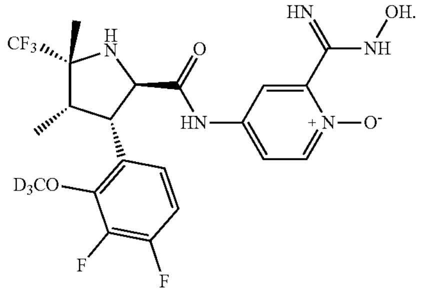
According to another aspect of the present invention, another object of the present invention is to provide a method for the preparation of the compounds represented by formula (I), stereoisomers, tautomers, deutero-derivatives or pharmaceutically acceptable salts thereof, the method comprises the steps of:
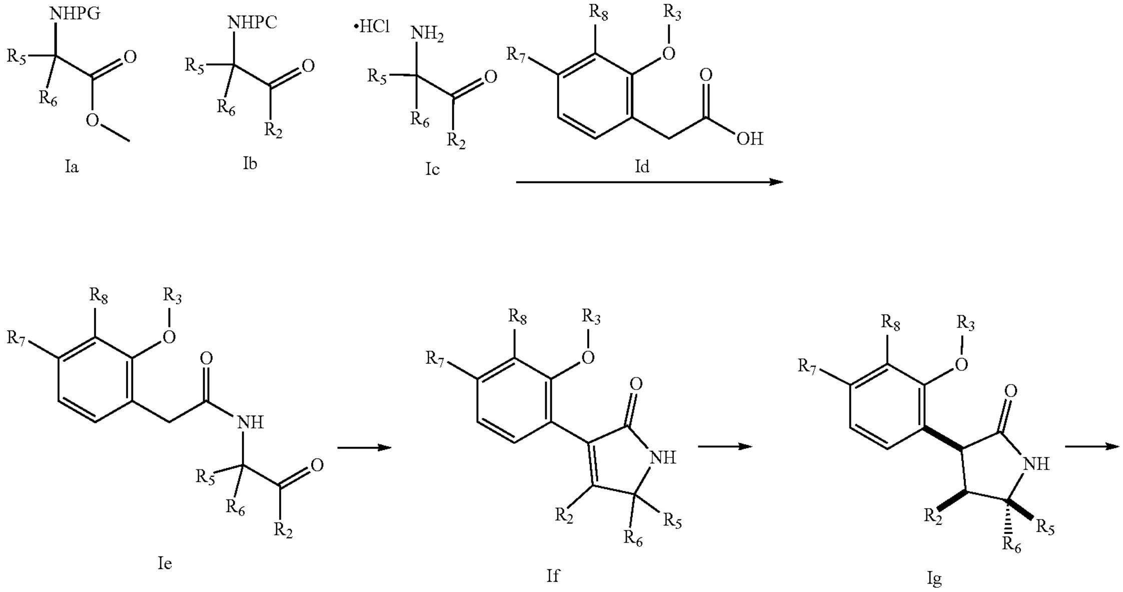
Ia Ib Ic Id
Ie If Ig -continued

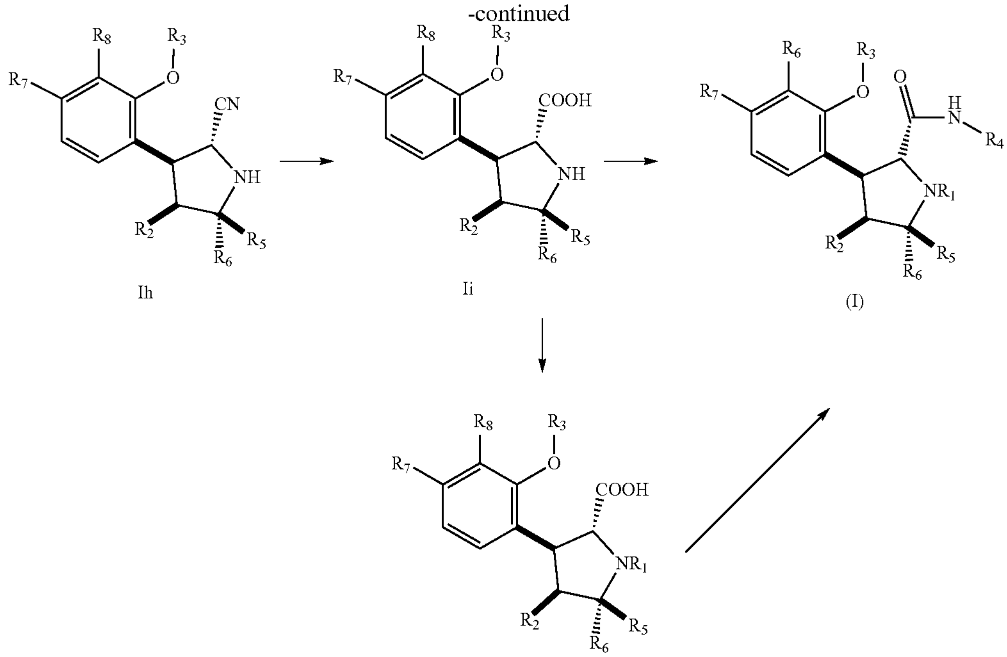

Ih Ii (I) Ii'

Step 1: reacting compound Ia, in which the amino is protected by the amino-protecting group PG, and the PG is Boc or Cbz, with alkyl metal reagent, (e.g., alkyl lithium, alkyl Grignard reagent, trimethylsilylmethyl lithium and the like) by electrophilic addition reaction to obtain compound Ib.

Step 2: removing the amino-protecting group PG from compound Ib in a hydrogen atmosphere under a strong acidic condition (e.g. hydrochloric acid/dioxane solution) or in the presence of metallic palladium carbon to obtain compound Ic.

Step 3: condensing compound Ic with compound Id, phenylacetic acid derivatives, by amide condensation to obtain compound Ie.

Step 4: performing intramolecular cyclization dehydration reaction with compound Ie under alkaline condition (e.g., potassium hydroxide, sodium hydroxide, sodium hydrogen, etc.) to obtain compound If.

Step 5: reducing the double bond in the ring with sodium borohydride and nickel chloride or palladium catalyzed hydrogenation conditions to obtain compound Ig.

Step 6: reducing lactam group in compound Ig to imine group with Schwartz reagent, then reacting with sodium cyanide or potassium cyanide by addition reaction to obtain pyrrolidine compound Ih.

Step 7: hydrolyzing the cyano in compound Ih to carboxyl group under strong acidic condition (e.g. hydrochloric acid/dioxane) or strong basic condition (e.g. aqueous potassium hydroxide) to obtain compound Ii.

Step 8: reacting compound Ii with aldehyde under palladium-catalyzed hydrogenation conditions or in the presence of a borohydride reducing agent to alkylate NH group in pyrrolidyl to obtain compound Ii'.

Step 9: Reacting Ii or Ii' with an amine by amide condensation to obtain the final product compound I.

According to another aspect of the present invention, the present invention provides a use of compounds represented by formula (I), stereoisomers, tautomers, deutero-derivatives or pharmaceutically acceptable salts thereof as Nav1.8 inhibitors.

According to another aspect of the present invention, the present invention provides a pharmaceutical composition, the pharmaceutical composition comprises a therapeutically effective amount of compounds represented by formula (I), stereoisomers, tautomers, deutero-derivatives or pharmaceutically acceptable salts thereof according to the present invention as an active ingredient, and a pharmaceutically acceptable excipient.

According to another aspect of the present invention, the present invention provides a use of the compounds represented by formula (I), stereoisomers, tautomers, deutero-derivatives or pharmaceutically acceptable salts thereof, or the pharmaceutical composition according to the present invention, in the preparation of a drug for the treatment of acute pain and chronic pain.

According to another aspect of the present invention, the present invention provides a method of treating chronic pain, the method comprises a step of providing to a subject a therapeutically effective amount of the compounds represented by formula (I), stereoisomers, tautomers, deutero-derivatives or pharmaceutically acceptable salts thereof or the pharmaceutical composition according to the present invention.

Beneficial Technical Effect

The compounds according to the present invention have high NaV1.8 inhibitory activity relative to compounds in the prior art and can be used in the treatment of acute pain and chronic pain.

BRIEF DESCRIPTION OF THE DRAWINGS

In order to more clearly illustrate the technical solutions in the specific embodiments of the present invention or prior art, the accompanying drawings that need to be used in the description of the specific embodiments or prior art will be briefly introduced, and it will be obvious that the accompanying drawings in the following description are some of the embodiments of the present invention, and that to a person skilled in the art, other drawings can be obtained based on these drawings without carrying out any creative work.

FIG. 1 shows an absolute configuration diagram of compound 5a prepared in Example 3.

DETAILED DESCRIPTION

In the following, the present invention will be described in detail. Before proceeding with the description, it should be understood that the terms used in this specification and the appended claims should not be construed to be limited to their general and dictionary meanings, but should be interpreted in accordance with meanings and concepts corresponding to the technical aspects of the present invention on the basis of the principle of permitting the inventor to define terms appropriately for optimal interpretation. Accordingly, the description presented herein is merely a preferred example for illustrative purposes and is not intended to limit the scope of the present invention, and thus it should be understood that other equivalent matters or improvements may be obtained therefrom without departing from the spirit and scope of the present invention.

Herein, the terms "comprising", "including", "having", "containing" or any other similar terms are open-ended transitional phrases which intend to cover non-exclusive contents. For example, composition or product containing elements in the plural is not limited to those elements listed herein, but may also include other elements not expressly listed but normally inherent in the composition or product. In addition, unless expressly stated to the contrary, the term "or" is meant to be inclusive rather than exclusive. For example, the condition "A or B" is satisfied in any of the following cases: A is true (or exists) and B is false (or does not exist), A is false (or does not exist) and B is true (or exists), or both A and B are true (or exist). In addition, herein, the terms "comprising", "including", "having", "containing" should be deemed to be understood as being specifically disclosed and to cover both the closed or semi-closed conjunctions "consisting of" and "substantially consisting of".

Herein, all features or conditions defined in the form of numerical ranges or percentage ranges are for the sake of brevity and convenience only. Accordingly, descriptions of numerical or percentage ranges are to be regarded as covering and specifically disclosing all possible sub-ranges and individual values within the ranges, especially integer values. For example, the description of the range "I to 8" shall be deemed to specifically disclose all sub-ranges such as 1 to 7, 2 to 8, 2 to 6, 3 to 6, 4 to 8, 3 to 8, etc., and in particular all sub-ranges defined by all integer values, and shall be deemed to specifically disclose individual values such as 1, 2, 3, 4, 5, 6, 7, 8, etc., within the range. Unless otherwise indicated, the foregoing method of interpretation applies to the entirety of the present invention, irrespective of its broad scope.

If quantity or other value or parameter is expressed as a range, a better range, or a series of upper and lower limits, it should be understood that all ranges limiting by any pair of upper or better values of the range and lower or better values of the range are specifically disclosed herein, whether or not such ranges are separately disclosed. In addition, when reference is made herein to a range of values, the range shall include its endpoints and all integers and fractions within the range, unless otherwise indicated.

Herein, a numerical value is to be understood as having a precision of the effective number of digits of the value, provided that the purpose of the invention can be achieved. For example, the number 40.0 should be understood to cover a range from 39.50 to 40.49.

Where Markush group or alternative terminology is used herein to describe features or instances of the present invention, it should be understood by those skilled in the art that subgroups or any individual element of all elements of the Markush group or options may also be used to describe the present invention. For example, if X is described as "selected from the group consisting of X1, X2, and X3", it should be understood that X is X1 and X is X1 and/or X2 have been fully described and claimed. Further, in cases where Markush group or alternative terms are used to describe features or embodiments of the present invention, it should be understood by those skilled in the art that subgroups of all the elements or any combination of individual elements within a Markush group or options may also be used to describe the present invention. Accordingly, for example, if X is described as "selected from the group consisting of X1, X2, and X3" and Y is described as "selected from the group consisting of Y1, Y2, and Y3", it means that X is X1 or X2 or X3 and Y is Y1 or Y2 or Y3 is fully described and claimed.

Definition

Definitions of specific functional groups and chemical terms are described in more detail below. The chemical elements are identified in accordance with the Periodic Table of the Elements, CAS version, *Handbook of Chemistry and Physics,* 75th Ed., inside cover, and specific functional groups are generally defined as described therein. The present invention is not intended to be limited in any way by the exemplary list of substituents described herein.

Compounds of the present disclosure can comprise one or more asymmetric centers and/or axial chirality, and thus can exist in various isomeric forms, e.g., enantiomers and/or diastereomers. For example, the compounds described herein can be in the form of an individual enantiomer, diastereomer, or geometric isomer, or can be in the form of a mixture of stereoisomers, including racemic mixtures and mixtures enriched in one or more stereoisomer. Isomers can be isolated from mixtures by methods known to those having ordinary skill in the art, including chiral high performance liquid chromatography (HPLC) and the formation and crystallization of chiral salts; or preferably, isomers can be prepared by asymmetric syntheses. The present disclosure additionally covers the compounds described herein as individual isomers substantially free of other isomers, or as mixtures of various isomers.

When a range of values is listed, it is intended to encompass each value and sub-range within the range. For example, "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$.

The term "alkyl" refers to a straight or branched saturated hydrocarbonyl having 1 to 15 carbon atoms ("$C_{1-15}$ alkyl"). In some embodiments, the alkyl has 1 to 6 carbon atoms ("$C_{1-6}$ alkyl"). In some embodiments, the alkyl has 1 to 5 carbon atoms ("$C_{1-5}$ alkyl"). In some embodiments, the alkyl has 1 to 4 carbon atoms ("$C_{1-4}$ alkyl"). In some embodiments, the alkyl has 1 to 3 carbon atoms ("$C_{1-3}$ alkyl"). In some embodiments, the alkyl has 1 to 2 carbon atoms ("$C_{1-2}$ alkyl"). In some embodiments, the alkyl has 1 carbon atom ("$C_1$ alkyl"). In some embodiments, the alkyl has 2 to 6 carbon atoms ("$C_{2-6}$ alkyl"). Examples of $C_{1-6}$ alkyl include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl (Cs) (e.g., n-pentyl, 3-pentyl, neopentyl, 3-methyl-2-butyl, tert-pentyl) and hexyl ($C_6$) (e.g., n-hexyl). Unless otherwise indicated, each example of alkyl is independently unsubstituted or substituted with one or more substituents (e.g., halogen, such as F). In some embodiments, the alkyl is an unsubstituted $C_{1-6}$ alkyl, such as —$CH_3$. In some embodiments, the alkyl is a substituted $C_{1-6}$ alkyl, such as —$CF_3$.

"Alkoxy" refers to a monovalent —O-alkyl, wherein the alkyl portion has a specified number of carbon atoms. Alkoxy in the present disclosure typically contains 1-6 carbon atoms ("$C_{1-6}$ alkoxy") and includes, for example, methoxy, ethoxy, isopropoxy, tert-butoxy, and the like. Unless otherwise indicated, each example of alkoxy is independently optionally substituted, i.e. unsubstituted ("unsubstituted alkoxy") or substituted with one or more substituents ("substituted alkoxy"), the substituents may, for example, be halogen atom, nitro, amino, hydroxy, cyano, amido, and the like. In some embodiments, the alkoxy is an unsubstituted $C_{1-6}$ alkoxy. In some embodiments, the alkoxy is a substituted $C_{1-6}$ alkoxy.

"Cycloalkyl" refers to a non-aromatic cyclic hydrocarbonyl in which the non-aromatic ring system has three to six cyclic carbon atoms ("$C_{3-6}$ cycloalkyl") and zero heteroatom. Exemplary $C_{3-6}$ cycloalkyl includes, but not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. As shown in the preceding examples, in some embodiments, the cycloalkyl is monocyclic ("monocyclic cycloalkyl") or contains a fused, bridged, or spiro ring system, such as a bicyclic system ("bicyclic cycloalkyl") and may be saturated or may be partially unsaturated. "Cycloalkyl" also includes ring systems in which cycloalkyl as defined above is fused with one or more aryl or heteroaryls at the point of attachment on carbon ring, and in which the carbon number continues to refer to the number of carbons in the carbon ring system. Unless otherwise indicated, each example of cycloalkyl is independently optionally substituted, i.e. unsubstituted or substituted with one or more substituents.

"Heterocyclyl" refers to a radical of a four- to eight-membered non-aromatic ring system having ring carbon atoms and 1 to 3 ring heteroatoms, wherein each heteroatom is independently selected from nitrogen, oxygen, sulphur, boron, phosphorus and silicon ("four- to eight-membered heterocyclyl"). In heterocyclyl containing one or more nitrogen atoms, the point of attachment can be a carbon or nitrogen atom, as valency permits. A heterocyclyl can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl, as defined above, is fused with one or more cycloalkyl groups wherein the point of attachment is either on the cycloalkyl or heterocyclyl, or ring systems wherein the heterocyclyl, as defined above, is fused with one or more aryl or heteroaryl groups, wherein the point of attachment is on the heterocyclyl, and in such instances, the number of ring members continues to designate the number of ring members in the heterocyclyl system. Unless otherwise indicated, each instance of the heterocyclyl is independently optionally substituted, i.e. unsubstituted or substituted with one or more substituents.

Exemplary 3-membered heterocyclyl containing one heteroatom includes, without limitation, aziridinyl, oxiranyl, and thiiranyl. Exemplary 4-membered heterocyclyl containing one heteroatom includes, without limitation, azetidinyl, oxetanyl and thietanyl. Exemplary 5-membered heterocyclyl containing one heteroatom includes, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl containing two heteroatoms includes, without limitation, dioxolanyl, oxasulfuranyl, disulfuranyl, and oxazolidin-2-one. Exemplary 5-membered heterocyclyl containing three heteroatoms includes, without limitation, triazolinyl, oxadiazolinyl, and thiadiazolinyl. Exemplary 6-membered heterocyclyl containing one heteroatom includes, without limitation, piperidinyl, tetrahydropyranyl, dihydropyridinyl, and thianyl. Exemplary 6-membered heterocyclyl containing two heteroatoms includes, without limitation, piperazinyl, morpholinyl, dithianyl, and dioxanyl. Exemplary 6-membered heterocyclyl containing two heteroatoms includes, without limitation, triazinanyl. Exemplary groups of 5-membered heterocyclyl fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary groups of 6-membered heterocyclyl fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatom provided in the aromatic ring system ("$C_{6-14}$ aryl"). In some embodiments, an aryl group has 6 ring carbon atoms ("$C_6$ aryl"; such as phenyl). In some embodiments, an aryl group has 10 ring carbon atoms ("$C_{10}$ aryl"; e.g., naphthyl, such as 1-naphthyl and 2-naphthyl). In some embodiments, an aryl group has 14 ring carbon atoms ("$C_{14}$ aryl"; e.g., anthracenyl). "Aryl" also includes ring systems wherein the aryl ring, as defined above, is fused with one or more cycloalkyl or heterocyclyl wherein the radical or point of attachment is on the aryl ring, and in such instances, the number of carbon atoms continue to designate the number of carbon atoms in the aryl ring system. Unless otherwise indicated, each instance of aryl is independently optionally substituted, i.e. unsubstituted ("unsubstituted aryl") or substituted with one or more substituents ("substituted aryl"), the substituent(s) may, for example, be halogen atom, nitro, amino, hydroxyl, cyano, amido, and the like. In some embodiments, the aryl is an unsubstituted $C_{6-14}$ aryl. In some embodiments, the aryl is a substituted $C_{6-14}$ aryl.

"Heteroaryl" refers to a radical of a five- to eight-membered monocyclic or bicyclic 4n+2 aromatic ring system (e.g., having 6 pi electrons shared in a cyclic array) having ring carbon atoms and 1-4 ring heteroatoms provided in the aromatic ring system, wherein each heteroatom is independently selected from nitrogen, oxygen and sulfur ("five- to eight-membered heteroaryl"). In heteroaryl groups containing one or more nitrogen atoms, the point of attachment can be a carbon or nitrogen atom, as valency permits. Heteroaryl bicyclic ring system can include one or more heteroatoms in one or both rings. "Heteroaryl" includes ring systems wherein the heteroaryl ring, as defined above, is fused with one or more cycloalkyl or heterocyclyl wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Unless otherwise expressly indicated, the atoms, portions or groups described herein may be unsubstituted or substituted as long as the valency permits.

"Halo" or "halogen" refers to fluorine (fluoro, —F), chlorine (chloro, —Cl), bromine (bromo, —Br) or iodine (iodo, —I).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. Pharmaceutically acceptable salts of the compounds according to the present invention herein include those derived from suitable inorganic and organic acids and bases. Examples of pharmaceutically acceptable, nontoxic acid addition salts include those formed with inorganic acids (such as hydrochloric acid, hydrobromic acid, phosphoric acid, sulfuric acid, and perchloric acid) or with organic acids (such as acetic acid, oxalic acid, maleic acid, tartaric acid, citric acid, succinic acid, or malonic acid) or amino-salt prepared by other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cypionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate ions.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on a number of factors, including temperature, solvent, and pH. The tautomeric reaction (i.e., the reaction that provides the tautomeric pairs) may be catalyzed by an acid or a base. Exemplary tautomeric reactions include keto-enol, amide-imide, lactam-lactim, enamine-imide, and enamine-(different enamines) tautomeric reactions.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "inhibition", "inhibiting", "inhibit," or "inhibitor" refer to the ability of a compound to reduce, slow, halt or prevent activity of a particular biological process (e.g., activity of Nav1.8 in tissues).

A "subject" to which administration is contemplated refers to a human (i.e., male or female of any age group, e.g., pediatric subject (e.g., infant, child, or adolescent) or adult subject (e.g., young adult, middle-aged adult, or senior adult)). A "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refer to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be applied after one or more signs or symptoms of the disease have developed or have been observed. In other embodiments, treatment may be administered in the absence of signs or symptoms of the disease. For example, treatment may be applied to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise an active ingredient between 0.1% and 100% (w/w).

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any benign fixed oil can be employed including synthetic mono- or di-glycerides. In addition, fatty acids such as oleic acid are used in the preparation of injectables.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled in the art can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of reasonable medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and other factors well known in the medical arts.

The compounds and compositions provided herein can be administered by any common route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops). Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of the compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, or one dose every week. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, the dose (e.g., a single dose, or any dose of multiple doses) described herein includes independently and inclusively the compound described herein in a range of between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein. In certain embodiments, a dose described herein includes independently between 100 mg and 300 mg, inclusive, of a compound as described herein. In certain embodiments, a dose described herein includes independently between 300 mg and 1000 mg, inclusive, of a compound described herein.

Examples

The following examples are merely examples of embodiments of the present invention, and do not constitute any limitation of the present invention, and those skilled in the art can understand that modifications within the scope of not deviating from the substance and conception of the present invention fall within the scope of protection of the present invention. Unless otherwise specified, the reagents and instruments used in the following embodiments are commercially available products.

$^1$H NMR spectra were determined with a Bruker instrument (400 MHz) and chemical shifts are expressed in ppm. An internal standard of tetramethylsilane (0.00 ppm) was used. Representation of $^1$H NMR: s=single peak, d=double peak, t=triple peak, m=multiple peak, br-broadened, dd=double peak of double peak, dt=double peak of triple peak. When coupling constants are provided, their units are Hz.

Mass spectra were obtained by LC/MS instrument and ionisation could be performed by ESI or APCI.

Thin layer chromatography silica gel plate is Yantai Huanghai HSGF254 or Qingdao GF254 silica gel plate, the specification of silica gel plate used in thin layer chromatography (TLC) is 0.15 mm to 0.2 mm, the specification of the product of thin layer chromatography separation and purification is 0.4 mm to 0.5 mm.

Column chromatography generally adopts 200~300 mesh silica gel from Yantai Huanghai silica gel as the carrier.

In the following examples, all temperatures are Celsius unless otherwise indicated, the various starting materials and reagents are commercially available or synthesised according to known methods, and the commercially available materials and reagents are used directly without further purification unless otherwise indicated, and are purchased from commercially available manufacturers including, but not limited to, Aldrich Chemical Company, ABCR GmbH &. Co. KG, Acros Organics, Shanghai BiDe Pharmaceutical Technology Co., and Shanghai Titan Scientific Co. Ltd.

The following abbreviations shall be understood as the following meanings unless otherwise stated or the context otherwise indicates.

$CD_3OD$: deutero-methanol.
$CDCl_3$: deutero-chloroform.
DMSO-$d_6$: deutero-dimethyl sulfoxide.
$D_2O$: heavy water.
NMR: Nuclear Magnetic Resonance
ESI-MS: Electrospray mass spectrometry analysis
LCMS: Liquid Chromatography-Mass Spectrometry
TLC: Thin Layer Chromatography
HPLC: High Performance Liquid Chromatography
prep-HPLC: Preparative-HPLC
SFC: Supercritical Fluid Chromatography
g: gram
mg: milligram
L: litre
mL: millilitre
μL: microlitre
mmol: millimole
hr, h: hour
min: minute
mm: millimeter
m: micron
MHz: megahertz
Hz: Hertz
eq.: equivalent
M: mole/litre (concentration)
DCM: Dichloromethane
DMF: N,N-Dimethylformamide
DMSO: Dimethyl sulfoxide
EtOH: Ethanol
EtOAc, EA: Ethyl acetate
NMI: N-methylimidazole
TCFH: N,N,N',N'-Tetramethylchloroformamidinium Hexafluorophosphate
MeOH: Methanol
MTBE: Methyl tertiary butyl ether
THF: tetrahydrofuran
ACN: Acetonitrile
TEA: Triethylamine
TGA: mercaptoacetic acid
RT, r.t.: room temperature
MeMgBr: Methyl Magnesium Bromide
Schwartz's Reagent: Bis(cyclopentadienyl)zirconium hydrochloride (IV)

The argon atmosphere can be achieved by attaching an argon balloon to the reaction flask.

Unless otherwise specified in the Examples, the solutions in the reactions are aqueous solutions.

The purification of compounds were performed by C18 reversed-phase column preparative or semi-preparative purification, silica gel column chromatography eluent system and thin-layer chromatography, in which the eluent system was selected from: A: petroleum ether and tetrahydrofuran system; B: acetonitrile and water system; C: petroleum ether and ethyl acetate system; in which the volumetric ratios of the solvents varied according to the polarity of the compounds, and could be adjusted by adding a small amount of acidic or alkaline reagents, such as trifluoroacetic acid, acetic acid or triethylamine.

Preparative Example 1: Synthesis of the intermediate 2-(3,4-difluoro-2-methoxyphenyl)acetyl chloride (Int1)

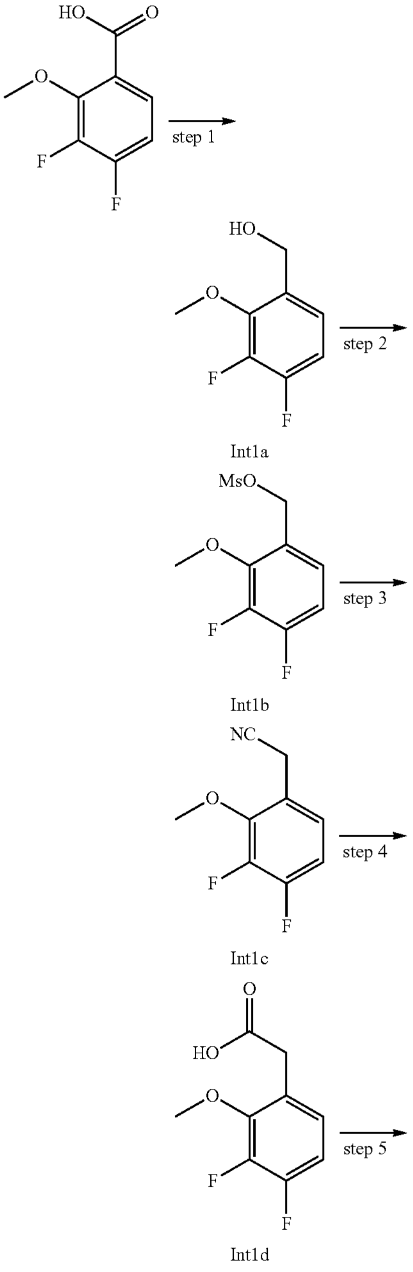

Int1a
Int1b
Int1c
Int1d

-continued

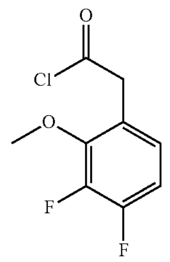

Int1

Step 1: 3,4-Difluoro-2-methoxybenzyl alcohol

To a solution of 3,4-difluoro-2-methoxybenzoic acid (20 g, 106 mmol) in anhydrous tetrahydrofuran (240 mL) was slowly added dropwise a solution of borane in tetrahydrofuran (1 M, 213 mL) in an ice bath, and after the dropwise addition, the temperature was raised to 25° C., and the mixture was stirred for 2 hr. The reaction was quenched by slowly adding dropwise methanol, and it was concentrated to obtain colorless oily compound 3,4-difluoro-2-methoxybenzyl alcohol Int1a (18 g, crude).

Step 2: 3,4-Difluoro-2-methoxybenzyl ester

In an ice bath, to a solution of 3,4-difluoro-2-methoxybenzyl alcohol Int1a (18 g, crude) and diisopropylethylamine (40 g, 310 mmol) in anhydrous dichloromethane (128 mL) was slowly added methanesulfonyl chloride (14 g, 124 mmol) dropwise, and then kept stirring in ice bath for 30 min, and then added aqueous hydrochloric acid (1M, 60 mL) and partitioned. The aqueous phase was extracted with dichloromethane (60 mL×3), the organic phases were combined, dried over anhydrous sodium sulfate, filtered and concentrated to obtain a brown oily compound 3,4-difluoro-2-methoxybenzyl methanesulfonate Int1b (20.00 g, crude).

Step 3: 2-(3,4-difluoro-2-methoxyphenyl)acetonitrile

Sodium cyanide (6.61 g, 134.80 mmol) was added into a solution of 3,4-difluoro-2-methoxybenzyl methanesulfonate Int1b (crude, 17 g, 67.40 mmol) in N,N-dimethylformamide (150 mL), stirred at 25° C. for 1 hr, then added ethyl acetate (150 mL) and water (150 mL) sequentially, and partitioned. The aqueous phase was extracted with ethyl acetate (100 mL×3), the organic phases were combined, dried over anhydrous sodium sulfate, filtered and concentrated, and purified by silica gel column chromatography (PE:THF=1:0 to 3:1) to afford a yellow oily compound 2-(3,4-difluoro-2-methoxyphenyl)acetonitrile Int1c (9.30 g, 71.57% yield).

$^1$H-NMR (400 MHz, $CDCl_3$) δ 7.25-7.03 (m, 1H), 6.90-6.83 (m, 1H), 4.07 (d, J=2.8 Hz, 3H), 3.65 (s, 2H).

Step 4: 2-(3,4-difluoro-2-methoxyphenyl)acetic acid

NaOH (15.5 g, 387 mmol) was added to a mixture of 2-(3,4-difluoro-2-methoxyphenyl)acetonitrile Int1c (9.3 g, 50.78 mmol) and water (350 mL), heated to reflux for 16 hr and cooled, and the pH was adjusted to 4 with an aqueous hydrochloric acid solution (4 M), and the mixture was extracted with ethyl acetate (200 mL×3), the organic phases were combined, dried over anhydrous sodium sulfate, filtered and concentrated to afford a light yellow solid compound 2-(3,4-difluoro-2-methoxyphenyl)acetic acid Int1d (10.20 g, 94.4% yield).

$^1$H-NMR (400 MHz, DMSO-d6) δ 12.41 (s, 1H), 7.13-7.05 (m, 2H), 3.86 (d, J=2.0 Hz, 3H), 3.56 (s, 2H).

Step 5: 2-(3,4-difluoro-2-methoxyphenyl)acetyl chloride 2-(3,4-difluoro-2-methoxyphenyl)acetic acid Int1d (500 mg, 2.47 mmol, 1 eq.) was dissolved in dichlorosulfoxide (5.0 mL) and stirred at room temperature for 16 h. The reaction was complete as detected by LCMS (the reaction solution was concentrated to dryness, and a tetrahydrofuran solution of dimethylamine was added). The reaction solution was concentrated to dryness under vacuum and anhydrous dichloromethane (5.0 mL) was added to the residue, which was again evaporated to dryness under vacuum to give a yellow oily compound 2-(3,4-difluoro-2-methoxyphenyl)acetyl chloride Int1 (540 mg, crude), which was used directly in the next step of the reaction.

Preparative Example 2: Synthesis of the intermediate methyl 2-((tert-butoxycarbonyl)amino)-3,3,3-trifluoro-2-methylpropionate (Int2)

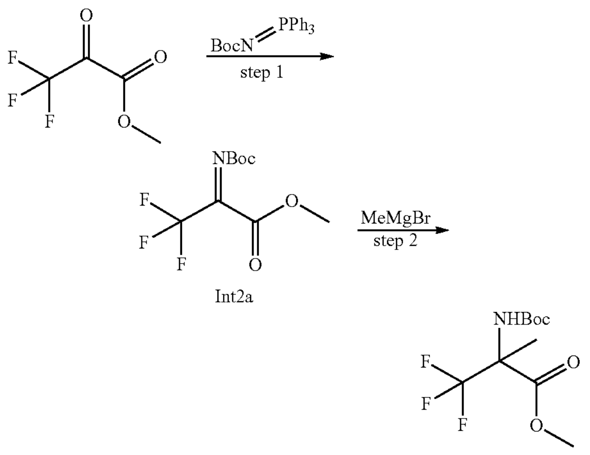

Step 1: Methyl 2-((tert-butoxycarbonyl)imino)-3,3,3-trifluoropropionate

To a solution of tert-butyl (triphenylphosphoranylideneimino)carbamate (23.1 g, 61.19 mmol, 1 eq.) in tetrahydrofuran (200 mL) was added methyl trifluoropyruvate (10.0 g, 64.08 mmol, 1.05 eq.), and the reaction system was protected with nitrogen and stirred at 50° C. for 10 min, then cooled down to 20° C. and continued stirring for 2 h. And it was detected by TLC (petroleum ether:ethyl acetate=5:1, $R_f$=0.6) that the raw material disappeared. The reaction solution was concentrated to dryness and pulped by adding mixed solvents (petroleum ether:ethyl ether=1:1), filtered, and the filtrate was concentrated under vacuum to give a colorless oily compound methyl 2-((tert-butoxycarbonyl)imino)-3,3,3-trifluoropropionate Int2a (16.8 g, crude, 100% yield).

$^1H$ NMR (400 MHz, $CDCl_3$), δ: 3.95 (s, 3H), 1.58 (s, 9H).

Step 2: Methyl rac-2-((tert-butoxycarbonyl)amino)-3,3,3-trifluoro-2-methylpropionate Compound methyl 2-((tert-butoxycarbonyl)imino)-3,3,3-trifluoropropionate Int2a (6.0 g, 23.51 mmol, 1 eq.) was dissolved in tetrahydrofuran (60.0 mL), cooled down to −70° C., methylmagnesium bromide was added thereto slowly and dropwise (7.84 mL, 23.51 mmol, 3 mol/L of 2-methyltetrahydrofuran solution, 1 eq.).). After dropwise addition, stirring was continued at −70° C. for 1 h. It was then raised to 20° C. and stirred for 30 min. It was detected by TLC (petroleum ether:ethyl acetate=5:1, $R_f$=0.5) that the raw material disappeared. The reaction was quenched by adding saturated ammonium chloride solution (200.0 mL) in ice bath, then extracted with ethyl acetate (200 mL) three times. The organic phases were combined, washed with saturated saline, dried, concentrated, and purified by normal-phase silica gel column chromatography (petroleum ether: ethyl acetate=10:1) to afford a compound methyl rac-2-((tert-butoxycarbonyl)amino)-3,3,3-trifluoro-2-methylpropionate Int2 as a white solid (5.2 g, crude, 81.54% yield).

$^1H$ NMR (400 MHz, $CDCl_3$), δ: 5.13 (s, 1H), 3.83 (s, 3H), 1.74 (s, 3H), 1.44 (s, 9H).

Example 1: Synthesis of 4-((2R,3S,4S,5R)-3-(3,4-difluoro-2-methoxyphenyl)-4,5-dimethyl-5-(trifluoromethyl)pyrrolidine-2-carboxamido)pyridinamide (1) and 4-((2S,3R,4R,5S)-3-(3,4-difluoro-2-methoxyphenyl)-4,5-dimethyl-5-(trifluoromethyl) pyrrolidine-2-carboxamido) pyridinamide (2)

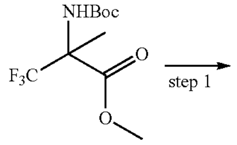

Int2

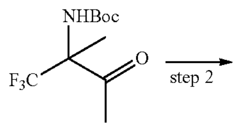

1a

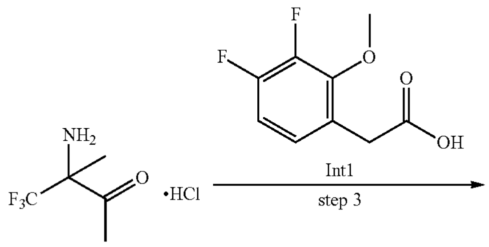

1b

-continued

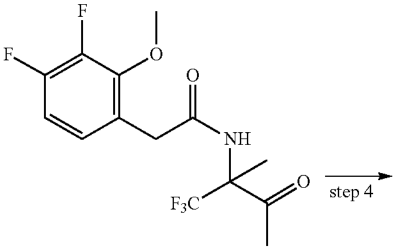

1c

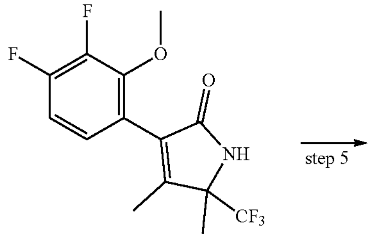

1d

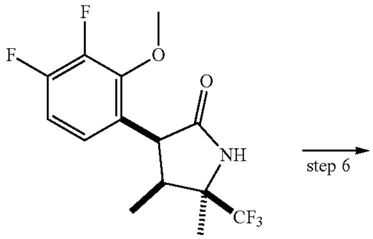

1e (rac)

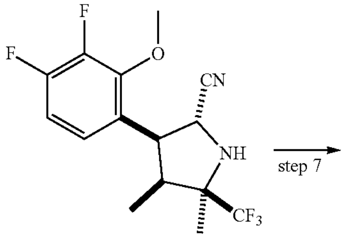

1f (rac)

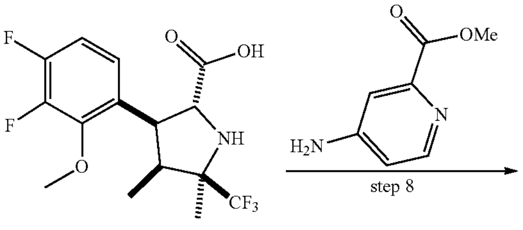

1g (rac)

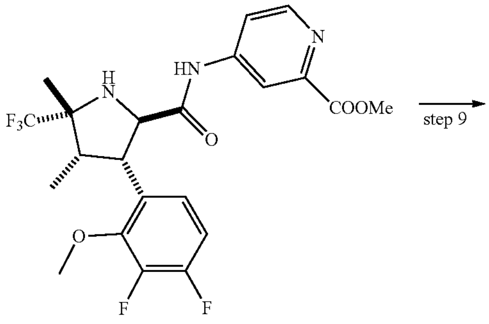

1h (rac)

-continued

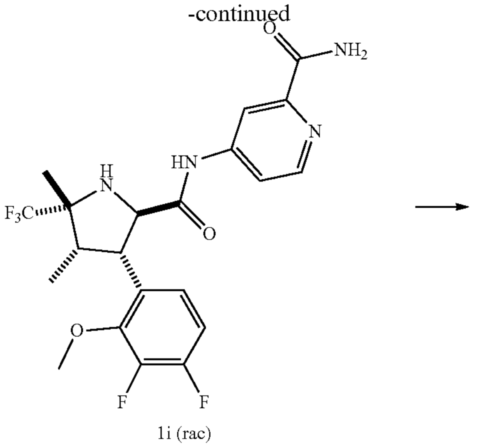

1i (rac)

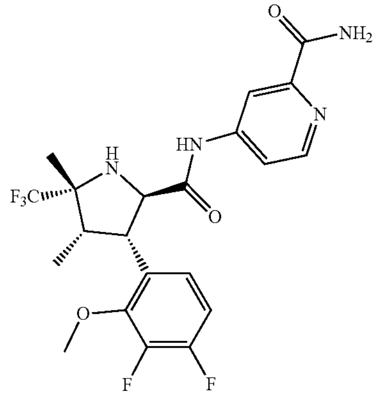

1

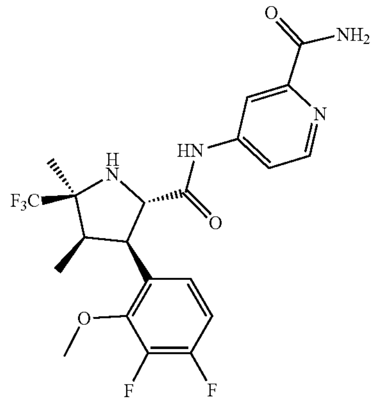

2

Step 1: tert-butyl rac-(1,1,1-trifluoro-2-methyl-3-oxobutan-2-yl)aminemethyl carbonate At −70° C., to a solution of methyl rac-2-((tert-butoxycarbonyl)amino)-3,3,3-trifluoro-2-methylpropionate Int2 (20.0 g, 73.747 mmol, 1.0 eq.) in tetrahydrofuran (400 mL) was slowly added dropwise trimethylsilylmethyl lithium (408.2 mL, 228.6 mmol, 0.56 mol/L hexane solution, 3.1 eq.). After dropwise addition, the mixture was stirred at −70° C. for 40 min, and it was detected by TLC (petroleum ether:ethyl acetate=5:1, $R_f$=0.3) that most of the raw material disappeared. The reaction solution was warmed to 0° C., quenched with anhydrous methanol (20.0 mL) and stirred for 30 min, then added with saturated ammonium chloride solution (1000 mL) and extracted three times with ethyl acetate (400 mL). The organic phases were combined, washed with saturated brine, dried over anhydrous sodium sulfate, and concentrated under vacuum to give a pale yellow oily compound tert-butyl rac-(1,1,1-trifluoro-2-methyl-3-oxobutan-2-yl)aminemethyl carbonate 1a (20.1 g crude).

$^1$H NMR (400 MHz, $CDCl_3$), δ: 5.15 (m, 1H), 2.21 (s, 3H), 1.53 (s, 3H), 1.35 (s, 9H).

Step 2: rac-3-amino-4,4,4-trifluoro-3-methylbutan-2-one

Compound tert-butyl rac-(1,1,1-trifluoro-2-methyl-3-oxobutan-2-yl)aminemethyl carbonate 1a (19.1 g crude, 74.83 mmol, 1.0 eq.) was dissolved in 4M hydrochloric acid/hexahydroxane solution (191.0 mL) and stirred at room temperature for 2 h. It was detected by TLC that the raw material disappeared. The reaction solution was concentrated to dryness, pulped by adding ethyl ether, filtered, and the filter cake was dried under vacuum to obtain a white solid compound rac-3-amino-4,4,4-trifluoro-3-methylbutan-2-one 1b (9.64 g crude).

$^1$H NMR (400 MHz, DMSO-d6), δ: 2.45 (s, 3H), 1.70 (s, 3H).

Step 3: rac-2-(3,4-difluoro-2-methoxyphenyl)-N-(1,1,1-trifluoro-2-methyl-3-oxobutan-2-yl)acetamide To a suspension of compound rac-3-amino-4,4,4-trifluoro-3-methylbutan-2-one 1b (9.52 g crude, 49.69 mmol, 1.0 eq.) in dichloromethane (90.0 mL) was added pyridine (39.3 g, 496.86 mmol, 10.0 eq.) at −10° C., followed by a slow dropwise addition of a solution of 2-(3,4-difluoro-2-methoxyphenyl)acetyl chloride Intl (12.06 g, 54.65 mmol, 1.1 eq.) in dichloromethane (40.0 mL) to the reaction solution. The reaction solution was allowed to naturally warm to room temperature and stirred for 16 h. LC/MS detection showed that the reaction was complete. 1 mol/L hydrochloric acid (1000.0 mL) was added to the reaction solution which was then extracted three times with dichloromethane (300.0 mL). The organic phases were combined, washed with saturated brine, dried over anhydrous sodium sulfate, and concentrated under vacuum to afford a yellow solid compound rac-2-(3,4-difluoro-2-methoxyphenyl)-N-(1,1,1-trifluoro-2-methyl-3-oxobutan-2-yl)acetamide 1c (11.7 g, 69.4% yield).

MS (ESI): m/z calculated [M+H$^+$]: 340.09, measured: 340.2

$^1$H NMR (400 MHz, DMSO-d6), δ: 9.15 (s, 1H), 7.13-7.04 (m, 2H), 3.86-3.84 (m, 3H), 3.62-3.53 (m, 2H), 2.05 (s, 3H), 1.49 (s, 3H).

Step 4: rac-3-(3,4-difluoro-2-methoxyphenyl)-4,5-dimethyl-5-(trifluoromethyl)-1,5-dihydro-2H-pyrrol-2-one Compound rac-2-(3,4-difluoro-2-methoxyphenyl)-N-(1,1,1-trifluoro-2-methyl-3-oxobutan-2-yl)acetamide 1c (11.7 g, 4.72 mmol, 1.0 eq.) was dissolved in hot ethanol (120.0 mL) followed by adding potassium hydroxide (1.94 g, 34.49 mmol, 1.0 eq.). The reaction solution was warmed to 80° C. and stirred for 20 min, and LC/MS detection showed that the reaction was complete. The reaction solution was cooled to room temperature, poured into water (1000.0 mL) and extracted three times with dichloromethane (400.0 mL). The organic phases were combined, washed with saturated brine, dried over anhydrous sodium sulfate, and concentrated under vacuum to give a light yellow solid compound rac-3-(3,4-difluoro-2-methoxyphenyl)-4,5-dimethyl-5-(trifluoromethyl)-1,5-dihydro-2H-pyrrol-2-one 1d (8.8 g, 79.4% yield).

MS (ESI): m/z Calculated [M+H$^+$]: 322.08, measured: 322.2

$^1$H NMR (400 MHz, DMSO-d6), δ: 9.13 (s, 1H), 7.27-7.21 (m, 1H), 7.04-6.99 (m, 1H), 3.75 (d, J=1.2 Hz, 3H), 1.88 (s, 3H), 1.56 (s, 3H).

Step 5: rac-(3S,4S,5R)-3-(3,4-difluoro-2-methoxyphenyl)-4,5-dimethyl-5-(trifluoromethyl) pyrrolidin-2-one Compound rac-3-(3,4-difluoro-2-methoxyphenyl)-4,5-dimethyl-5-(trifluoromethyl)-1,5-dihydro-2H-pyrrol-2-one 1d (14.63 g, 45.54 mmol, 1.0 eq.) was dissolved in a mixed solvent (tetrahydrofuran:methanol=1:5, 540.0 mL), cooled down to −40° C., and nickel chloride hexahydrate (10.82 g, 45.54 mmol, 1.0 eq.) and sodium borohydride (5.17 g, 136.62 mmol, 3.0 eq.) were added sequentially. The reaction mixture was stirred for 1 h. The reaction was continued at −40° C. by adding equal amounts of nickel chloride hexahydrate and sodium borohydride as described above until the raw material was consumed as indicated by LC/MS. The reaction solution was filtered, the filtrate was concentrated, added with saturated ammonium chloride solution (1000.0 mL), and extracted three times with dichloromethane (300.0 mL). The organic phases were combined, washed with saturated saline water, dried over anhydrous sodium sulfate, and concentrated under vacuum, and the residue was pulped by adding a mixture of solvents (100.0 mL, petroleum ether:ethyl acetate=20:1) for 1 h, then filtered, and the cake was dried to obtain compound rac-(3S,4S,5R)-3-(3,4-difluoro-2-methoxyphenyl)-4,5-dimethyl-5-(trifluoromethyl) pyrrolidin-2-one 1e as a white solid (11.17 g, 75.9% yield).

MS (ESI): m/z calculated [M+H$^+$]: 324.09, measured: 324.2.

$^1$H NMR (400 MHz, DMSO-d6), δ: 8.90 (s, 1H), 7.16-7.09 (m, 1H), 6.85-6.83 (m, 1H), 4.22 (d, J=10.4 Hz, 1H), 3.92 (d, J=1.6 Hz, 3H), 2.85 (m, 1H), 1.48 (s, 3H), 0.68 (d, J=6.0 Hz, 3H). 0.68 (d, J=6.0 Hz, 3H).

Step 6: rac-(2R,3S,4S,5R)-3-(3,4-difluoro-2-methoxyphenyl)-4,5-dimethyl-5-(trifluoromethyl) pyrrolidine-2-carbonitrile To a nitrogen-protected suspension of bis(cyclopentadienyl)zirconium chloride hydride (Schwartz reagent) (3.52 g, 13.64 mmol, 5.0 eq.) in tetrahydrofuran (20.0 mL) was added a solution of compound rac-(3S,4S,5R)-3-(3,4-difluoro-2-methoxyphenyl)-4,5-dimethyl-5-(trifluoromethyl) pyrrolidin-2-one 1e (882.0 mg, 2.73 mmol, 1.0 eq.) in tetrahydrofuran (8.0 mL). After stirring for 0.25 h, the reaction mixture was naturally warmed to 20° C. and stirring was continued for 16 h. LC/MS detection showed that all of the raw material was converted to imine. The mixture was filtered and the filtrate was concentrated under vacuum to obtain the crude imine intermediate. The prepared crude imine was dissolved in dichloromethane (10.0 mL) and cooled down to 5° C., added with TMSCN (5.41 g, 54.57 mmol, 20.0 eq.), and then naturally warmed to 20° C. and stirred for 4 days. LC/MS detection showed that the imine was completely converted, and then a saturated solution of sodium bicarbonate (100.0 mL) was added, and then it was extracted three times by dichloromethane (50 mL), and the organic phases were combined, washed with saturated saline, dried over anhydrous sodium sulfate, and concentrated under vacuum, and the residue was purified by normal-phase silica gel chromatography column (petroleum ether:ethyl acetate=20:1) to obtain a colorless oily compound rac-(2R,3S,4S,5R)-3-(3,4-difluoro-2-methoxyphenyl)-4,5-dimethyl-5-(trifluoromethyl)pyrrolidine-2-carbonitrile if (516.0 mg, 56.6% yield).

MS (ESI): m/z calculated [M+H$^+$]: 335.11, measured: 335.2.

$^1$H NMR (400 MHz, DMSO-d6), δ: 7.21-7.14 (m, 2H), 4.55-4.52 (m, 1H), 4.12 (d, J=4.4 Hz, 1H), 3.96 (d, J=2.4 Hz, 3H), 2.71-2.64 (m, 1H), 1.48 (s, 3H), 0.70-0.68 (m, 3H).

Step 7: rac-(2R,3S,4S,5R)-3-(3,4-difluoro-2-methoxyphenyl)-4,5-dimethyl-5-(trifluoromethyl) pyrrolidine-2-carboxylic acid To a solution of compound rac-(2R,3S,4S,5R)-3-(3,4-difluoro-2-methoxyphenyl)-4,5-dimethyl-5-(trifluoromethyl)pyrrolidine-2-cyanonitrile if (516.0 mg, 1.54 mmol, 1.0 eq.) in 1,4-dioxane (3.0 mL) was added concentrated hydrochloric acid (15.0 mL) and the reaction mixture was stirred at 55° C. for 6 h. LCMS detection showed that the reaction was complete. The reaction mixture was concentrated to dryness under vacuum, and the residue was dissolved in a mixture of water (20.0 mL) and ethyl acetate (10.0 mL), and the pH was adjusted to 5 with sodium bicarbonate, and then it was extracted with ethyl acetate (5.0 mL) for three times, and the organic phases were combined, washed with saturated saline, dried over anhydrous sodium sulfate, and concentrated under vacuum to give a pale yellow oily compound rac-(2R,3S, 4S,5R)-3-(3,4-difluoro-2-methoxyphenyl)-4,5-dimethyl-5-(trifluoromethyl)pyrrolidine-2-carboxylic acid 1g (540.0 mg, 99.0% yield).

MS (ESI): m/z calculated [M+H$^+$]: 354.11, measured: 354.2;

$^1$H NMR (400 MHz, $CDCl_3$), δ: 7.06-7.00 (m, 1H), 6.89-6.82 (m, 1H), 4.28 (d, J=9.6 Hz, 1H), 4.00-3.92 (m, 4H), 2.58-2.50 (m, 1H), 1.53 (s, 3H), 0.75-0.73 (m, 3H).

Step 8: rac-methyl-4-((2R,3S,4S,5R)-3-(3,4-difluoro-2-methoxyphenyl)-4,5-dimethyl-5-(trifluoromethyl)pyrrolidin-2-amide)pyridine carboxylate To a solution of methyl 4-aminopyridine-2-carboxylate (2.45 g, 16.13 mmol, 30.0 eq.), compound rac-(2R,3S,4S,5R)-3-(3,4-difluoro-2-methoxyphenyl)-4,5-dimethyl-5-(trifluoromethyl) pyrrolidine-2-carboxylic acid 1g (190.0 mg, 537.8 μmol, 1.0 eq.) and N-methylimidazole (441.54 mg, 5.38 mmol, 10.0 eq.) in acetonitrile (40 mL) was added N,N,N',N'-tetramethylchloroformamidinium hexafluorophosphate (301.79 mg, 1.08 mmol, 2.0 eq.) in batches, and the reaction mixture was stirred at 20° C. for 16 h. The LCMS detection showed that the raw material was consumed, 200.0 mL of water was added to the reaction solution, the pH was adjusted to 7-8 with diluted hydrochloric acid, and then it was extracted three times with ethyl acetate (100 mL). The organic phases were combined, washed with saturated saline, dried over anhydrous sodium sulfate, and concentrated under vacuum, and the residue was purified by prep-HPLC (column model: Welch Xtimate C18 250*30 mm*10 um; mobile phase: water (0.05% HCl)-ACN; gradient: 30%-60%, 15 min; flow rate: 40 mL/min) to obtain a white solid compound rac-methyl-4-((2R,3S,4S,5R)-3-(3,4-difluoro-2-methoxyphenyl)-4,5-dimethyl-5-(trifluoromethyl)pyrrolidin-2-amide)pyridine carboxylate 1h (30.0 mg, 11.4% yield).

MS (ESI): m/z calculated [M+H+]: 487.15, measured: 488.3.

Step 9: Synthesis of 4-((2R,3S,4S,5R)-3-(3,4-difluoro-2-methoxyphenyl)-4,5-dimethyl-5-(trifluoromethyl)pyrrolidine-2-carboxamido)pyridine amide (1) and 4-((2S,3R,4R,5S)-3-(3,4-difluoro-2-methoxyphenyl)-4,5-dimethyl-5-(trifluoromethyl)pyrrolidine-2-carboxamido) pyridinamide (2)

The compound rac-methyl-4-((2R,3S,4S,5R)-3-(3,4-difluoro-2-methoxyphenyl)-4,5-dimethyl-5-(trifluoromethyl) pyrrolidin-2-amide)pyridine carboxylate 1 h (30.0 mg, 61.55 μmol, 1.0 eq.) was dissolved in 7 M $NH_3$/MeOH solution (3.0 mL) and stirred at 20° C. for 16 hr. The LCMS detection showed that the raw material was consumed, the reaction solution was concentrated under vacuum to dryness, and the residue was chirally separated by SFC (column model: ChiralPak Whelk-O1(S,S) column from Daicel Chemical Industries, particle size of 5 m, 250×30 mm in size; mobile phase: solvent A was supercritical carbon dioxide, solvent B was HPLC-grade ethanol containing 0.1% ammonia, A:B=70:30; flow rate: 50 mL/min; column temperature: 38° C.; detection wavelength: 220 nm), to obtain two single isomers with unknown absolute configuration:

4-((2R,3S,4S,5R)-3-(3,4-difluoro-2-methoxyphenyl)-4,5-dimethyl-5-(trifluoromethyl) pyrrolidine-2-carboxamido) pyridine amide (1) (first eluting isomer, 7.12 mg, 24.5% yield).

MS (ESI): m/z calculated [M+H+]: 473.15, measured: 473.1.

$^1$H NMR (400 MHz, $CDCl_3$), δ: 9.60 (s, 1H), 8.42 (d, J=5.2 Hz, 1H), 8.15 (d, J=4.0 Hz, 1H), 7.93 (s, 1H), 7.88 (s, 1H), 7.16-7.13 (m, 1H), 6.93-6.87 (m, 1H), 5.71 (s, 1H), 4.47 (d, J=9.6 Hz, 1H), 4.06 (t, J=9.2 Hz, 1H), 3.95 (d, J=2.4 Hz, 3H), 2.61 (q, J=7.6 Hz, 1H), 1.62 (s, 3H), 0.75-0.74 (m, 3H)

and 4-((2S,3R,4R,5S)-3-(3,4-difluoro-2-methoxyphenyl)-4,5-dimethyl-5-(trifluoromethyl) pyrrolidine-2-carboxamido)pyridine amide (2) (second eluting isomer, 6.03 mg, 20.7% yield).

MS (ESI): m/z calculated [M+H+]: 473.15, measured: 473.2.

1H NMR (400 MHz, $CDCl_3$), δ: 9.53 (s, 1H), 8.43 (d, J=5.2 Hz, 1H), 8.18 (d, J=3.6 Hz, 1H), 7.92 (d, J=1.6 Hz, 1H), 7.86 (s, 1H), 7.13-7.10 (m, 1H), 6.92-6.86 (m, 1H), 5.69 (s, 1H), 4.42 (d, J=10.4 Hz, 1H), 4.04 (t, J=9.2 Hz, 1H), 3.95 (d, J=2.4 Hz, 3H), 2.60 (q, J=7.6 Hz, 1H), 1.60 (s, 3H), 0.75-0.73 (d, J=1.6 Hz, 1H), 7.13-7.10 (m, 1H), 7.13-7.10 (m, 1H), 7.13-7.10 (m, 1H) 0.75-0.73 (m, 3H)

Example 2: Synthesis of 4-((2R,3S,4S,5R)-3-(3,4-difluoro-2-methoxyphenyl)-1,4,5-trimethyl-5-(trifluoromethyl)pyrrolidine-2-carboxamido)pyridine amide (3) and 4-((2S,3R,4R,5S)-3-(3,4-difluoro-2-methoxyphenyl)-1,4,5-trimethyl-5-(trifluoromethyl) pyrrolidine-2-carboxamido)pyridinamide (4)

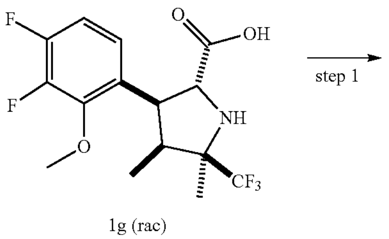

1g (rac)

-continued

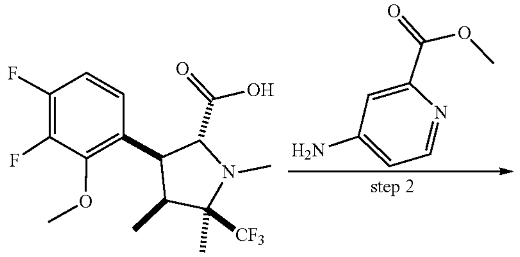

3a (rac)

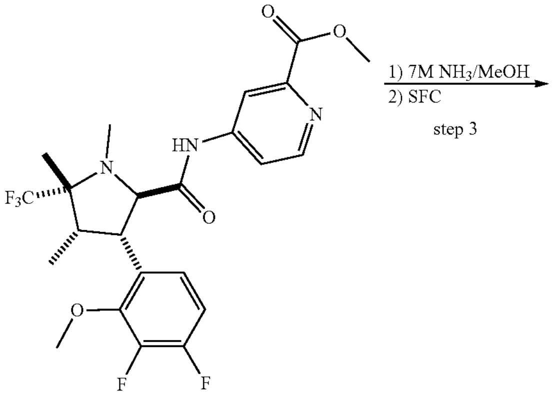

3b (rac)

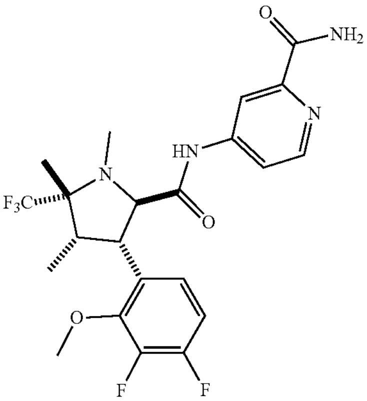

and

3

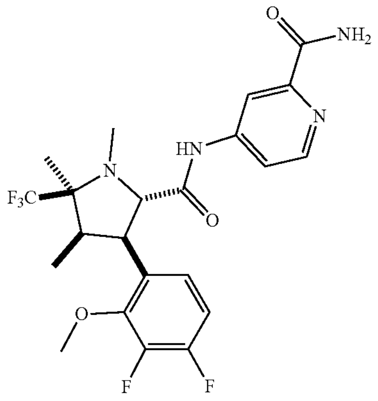

4

Step 1: rac-(2R,3S,4S,5R)-3-(3,4-difluoro-2-methoxyphenyl)-1,4,5-trimethyl-5-(trifluoromethyl)pyrrolidine-2-carboxylic acid Compound 1 g of rac-(2R,3S,4S,5R)-3-(3,4-difluoro-2-methoxyphenyl)-4,5-dimethyl-5-(trifluoromethyl)pyrrolidine-2-carboxylic acid (100.0 mg, 283.05 μmol, 1.0 eq.) was dissolved in methanol (5.0 mL), and then added sequentially with 18% aqueous formaldehyde (944.46 mg, 5.66 mmol, 20.0 eq.) and palladium-carbon (60.25 mg, 28.31 μmol, 0.1 eq., 10% of loaded Pd, 50% water in catalyst), and the reaction mixture was stirred at room temperature under an atmosphere of hydrogen (5.0 MPa) for 16 h. The LCMS detection showed that the raw materials were consumed, and the reaction solution was filtered, and the filtrate was concentrated to dryness under vacuum to give a light yellow solid compound rac-(2R,3S,4S,5R)-3-(3,4-difluoro-2-methoxyphenyl)-1,4,5-trimethyl-5-(trifluoromethyl)pyrrolidine-2-carboxylic acid 3a (102.0 mg, 98.1% yield).

MS (ESI): m/z calculated [M+H$^+$]: 368.12, measured: 368.3.

Step 2: rac-methyl 4-((2R,3S,4S,5R)-3-(3,4-difluoro-2-methoxyphenyl)-1,4,5-trimethyl-5-(trifluoromethyl)pyrrolidin-2-amide)pyridinecarboxylate To a suspension dissolved with compound rac-(2R,3S,4S,5R)-3-(3,4-difluoro-2-methoxyphenyl)-1,4,5-trimethyl-5-(trifluoromethyl)pyrrolidine-2-carboxylic acid 3a (1.66 g, 10.89 mmol, 40.0 eq.), compound 12 (100.0 mg, 272.24 μmol, 1.0 eq.) and N-methylimidazole (335.27 mg, 4.08 mmol, 15 eq.) in acetonitrile (10.0 mL) was added N,N,N',N'-tetramethylchloroformamidium hexafluorophosphate (152.77 mg, 544.48 μmol, 2.0 eq.) in batches, and the reaction mixture was sonicated and shaken for 24 h at 20° C. LCMS detection showed the formation of product. Then 200.0 mL of water was added to the reaction solution, the pH was adjusted to 7 to 8 with dilute hydrochloric acid and it was extracted three times with ethyl acetate (100 mL). The organic phases were combined, washed with saturated saline, dried over anhydrous sodium sulfate, and concentrated under vacuum, and the residue was purified by prep-HPLC (column: Phenomenex Luna C18, 150*25 mm*10 um; mobile phase: water (0.1% TFA)-ACN; gradient: 30%-60%, 15 min; flow rate: 40 mL/min) to obtain a white solid compound rac-methyl 4-((2R,3S,4S,5R)-3-(3,4-difluoro-2-methoxyphenyl)-1,4,5-trimethyl-5-(trifluoromethyl)pyrrolidin-2-amide)pyridine carboxylate 3b (59.0 mg, 43.2% yield).

MS (ESI): m/z calculated [M+H$^+$]: 502.17, measured: 502.5.

Step 3: 4-((2R,3S,4S,5R)-3-(3,4-difluoro-2-methoxyphenyl)-1,4,5-trimethyl-5-(trifluoromethyl)pyrrolidine-2-carboxamido)pyridine amide (3) and rel-4-((2S,3R,4R,5S)-3-(3,4-difluoro-2-methoxyphenyl)-1,4,5-trimethyl-5-(trifluoromethyl)pyrrolidine-2-carboxamido) pyridinamide (4)

Compound rac-methyl 4-((2R,3S,4S,5R)-3-(3,4-difluoro-2-methoxyphenyl)-1,4,5-trimethyl-5-(trifluoromethyl)pyrrolidin-2-amide)pyridine carboxylate 3b (59.0 mg, 117.66 μmol, 1.0 eq.) was dissolved in a solution of 7 M $NH_3$/MeOH (3.0 mL) and stirred at 20° C. for 16 h. The LCMS detection showed that the raw materials were consumed, the reaction solution was concentrated under vacuum and dried, and the residue was chirally separated by SFC (column model: ChiralPak Whelk-O1(S,S) column from Daicel Chemical Industries, 5 m particle size, 250×30 mm; mobile phase: supercritical carbon dioxide as solvent A and HPLC-grade ethanol containing 0.1% ammonia as solvent B, A:B=80:20; flow rate: 50 mL/min; column temperature: 38° C.; detection wavelength: 220 nm), to obtain two single isomers with unknown absolute configuration:

4-((2R,3S,4S,5R)-3-(3,4-difluoro-2-methoxyphenyl)-1,4,5-trimethyl-5-(trifluoromethyl)pyrrolidine-2-carboxamido) pyridine amide (3) (first eluting isomer, 14.81 mg, 25.9% yield)

MS (ESI): m/z calculated [M+H$^+$]: 487.17, measured: 487.2.

$^1$H NMR (400 MHz, $CDCl_3$) δ 8.99 (s, 1H), 8.47 (d, J=5.6 Hz, 1H), 8.29 (dd, J=5.6, 2.1 Hz, 1H), 7.92 (m, 2H), 7.17 (t, J=7.4 Hz, 1H), 6.89 (td, J=9.3, 7.5 Hz, 1H), 5.55 (s, 1H), 4.03 (d, J=8.3 Hz, 1H), 3.99-3.90 (m, 1H), 3.87 (d, J=2.7 Hz, 3H), 2.74 (q, J=7.9 Hz, 1H), 2.59 (m, 3H), 1.57 (s, 3H), 0.83-0.69 (m, 3H).

and 4-((2S,3R,4R,5S)-3-(3,4-difluoro-2-methoxyphenyl)-1,4,5-trimethyl-5-(trifluoromethyl)pyrrolidine-2-carboxamido)pyridine amide (4) (second eluting isomer, 11.84 mg, 20.7% yield)

MS (ESI): m/z calculated [M+H$^+$]: 487.17, measured: 487.2.

$^1$H NMR (400 MHz, $CDCl_3$) δ 8.98 (s, 1H), 8.46 (d, J=5.6 Hz, 1H), 8.29 (dd, J=5.6, 2.1 Hz, 1H), 7.91 (d, J=2.2 Hz, 1H), 7.88 (s, 1H), 7.18 (t, J=7.2 Hz, 1H), 6.96-6.86 (m, 1H), 5.49 (s, 1H), 4.02 (d, J=8.1 Hz, 1H), 3.98-3.89 (s, 1H) 6.96-6.86 (m, 1H), 5.49 (s, 1H), 4.02 (d, J=8.1 Hz, 1H), 3.98-3.89 (m, 1H), 3.87 (d, J=2.6 Hz, 3H), 2.75 (q, J=8.0 Hz, 1H), 2.59 (m, 3H), 1.56 (s, 3H), 0.83-0.64 (m, 3H).

Example 3: Synthesis of (2R,3S,4S,5R)-3-(3,4-difluoro-2-methoxyphenyl)-aza-(6-((S)-1,2-dihydroxyethyl)pyridin-3-yl)-4,5-dimethyl-5-(trifluoromethyl)pyrrolidine-2-carboxamide (5)

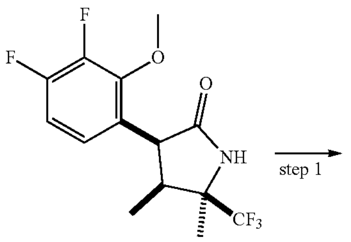

1e (rac)

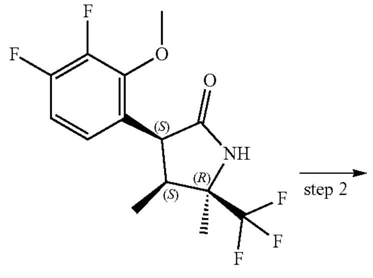

5a

-continued

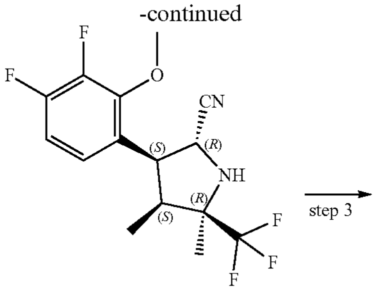

5b

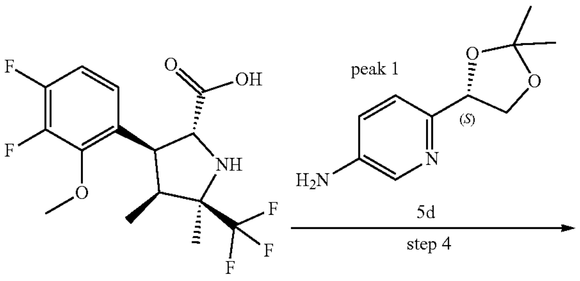

5c

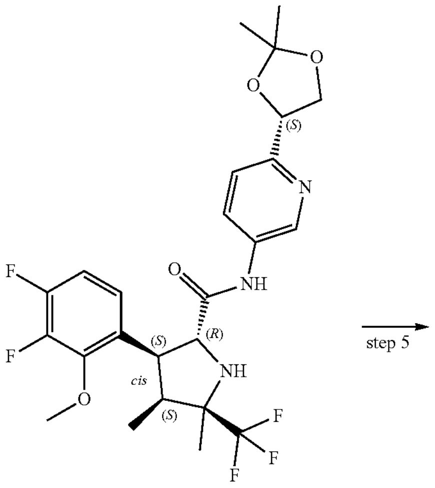

5e

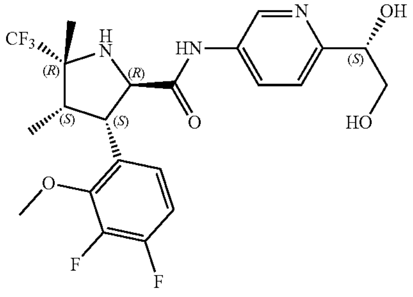

5

Step 1: 2.0 g of racemic compound 1e was separated by SFC chiral separation (column: ChiralPak AD-H column from Daicel Chemical Industries, 5 m particle size, 250×30 mm; mobile phase: supercritical carbon dioxide as solvent A, HPLC-grade ethanol containing 0.1% ammonia as solvent B, A:B=90:10; flow rate: 60 mL/min; injection pressure: 100 bar; column temperature: 38° C.; detection wavelength: 220 nm) so as to obtain compound 5a (first eluting isomer, 940 mg) with a single configuration, and its absolute configuration was charactered by single-crystal X-ray diffraction. The preparation procedure and SC-XRD test data of the single crystals were as follows: 50 mg of compound 2 was dissolved in 0.5 mL of ether and the solution was slowly evaporated naturally over 7 days, the precipitation of several single crystals of compound 2 could be observed. The single crystals without defects were taken for SC-XRD testing and the data were analyzed to give the absolute configuration of compound 5a as shown in FIG. 1 and the cellular parameters are listed in Table 1 below.

MS (ESI): m/z calculated [M+H$^+$]: 324.09, measured: 324.2.

$^1$H NMR (400 MHz, DMSO-d4) δ 8.90 (s, 1H), 7.13 (ddd, J=10.3, 8.9, 7.8 Hz, 1H), 6.91-6.74 (m, 1H), 4.22 (d, J=10.5 Hz, 1H), 3.92 (d, J=2.4 Hz, 3H), 2.84 (q, J=8.4 Hz, 1H), 1.48 (s, 3H), 0.70-0.67 (m, 3H). 3H), 2.84 (q, J=8.4 Hz, 1H), 1.48 (s, 3H), 0.70-0.67 (m, 3H).

TABLE 1

| Crystal system. | trigonal crystal system |
|---|---|
| Space group | $P3_2(145)$ |
| a [Å] | 12.1855(3) |
| b [Å] | 12.1855(3) |
| c [Å] | 8.5247(4) |
| α [°] | 90 |
| β [°] | 90 |
| γ [°] | 120 |
| Volume [Å$^3$] | 1096.22(7) |
| Z | 3 |
| temperature | 150 K |

Step 2: To a suspension of bis(cyclopentadienyl)zirconium chloride hydride (Schwartz reagent) reagent (3.15 g, 12.22 mmol, 5.0 eq.) in THF (15.0 mL) was added a solution of compound 5a (790 mg, 2.44 mmol, 1.0 eq.) in THF (5.0 mL) at −30° C. under nitrogen protection. After stirring for 0.25 h, the reaction mixture was naturally warmed to 20° C. and continued to stir for 16 h. LCMS detection showed that all of the raw material was converted to imine. Then it was filtered and the filtrate was concentrated under vacuum to obtain the crude imine intermediate. The prepared crude imine was dissolved in dichloromethane (10.0 mL) and cooled down to 5° C., and then TMSCN (3.64 g, 36.66 mmol, 15.0 eq.) was added, and then the mixture was naturally warmed up to 20° C. and stirred for 4 days. The LCMS detection showed that the imine was converted, and then saturated sodium bicarbonate solution (100.0 mL) was added, and then it was extracted three times by dichloromethane (50 mL), and the organic phases were combined, washed with saturated saline, dried over anhydrous sodium sulfate and concentrated under vacuum, and the residue was purified by normal-phase silica gel column (petroleum ether: ethyl acetate=20:1) to obtain a colorless oily compound 5b (430.0 mg, 52.63% yield).

MS (ESI): m/z calculated [M+H$^+$]: 335.11, measured: 335.1.

1H NMR (400 MHz, DMSO-d6) δ 7.28-7.09 (m, 2H), 4.53 (dd, J=7.0, 4.6 Hz, 1H), 4.12 (d, J=4.7 Hz, 1H), 3.96 (d, J=2.4 Hz, 3H), 3.95-3.88 (m, 1H), 2.67 (q, J=7.6 Hz, 1H), 1.48 (s, 3H), 0.70-0.68 (m, 3H), 0.70-0.68 (m, 3H) 3.88 (m, 1H), 2.67 (q, J=7.6 Hz, 1H), 1.48 (s, 3H), 0.70-0.68 (m, 3H).

Step 3: To a solution of compound 5b (430.0 mg, 1.29 mmol, 1.0 eq.) in 1,4-dioxane (2.0 mL) was added concentrated hydrochloric acid (10.0 mL), and the reaction mixture was stirred at 55° C. for 16 h. LCMS detection showed that the reaction was complete. The reaction mixture was concentrated to dryness under vacuum and the residue was dissolved in a mixture of water (20.0 mL) and ethyl acetate (10.0 mL), the pH was adjusted to 5 with sodium bicarbonate and then it was extracted with ethyl acetate (5.0 mL) three times. The organic phases were combined, washed with saturated saline, dried over anhydrous sodium sulfate, and concentrated under vacuum to give a light yellow solid compound 5c (410.0 mg. 90.22% yield).

MS (ESI): m/z calculated [M+H$^+$]: 354.11, measured: 354.1.

$^1$HNMR (400 MHz, DMSO-$d_6$) δ 12.81 (s, 1H), 7.23 (ddd, J=8.3, 6.0, 2.0 Hz, 1H), 7.13 (td, J=9.6, 7.6 Hz, 1H), 4.12 (d, J=8.9 Hz, 1H), 3.90 (d, J=2.0 Hz, 3H), 3.88-3.82 (m, 1H), 2.80 (s, 1H), 2.46 (d, J=7.6 Hz, 1H), 1.47 (s, 3H) 3.88-3.82 (m, 1H), 2.80 (s, 1H), 2.46 (d, J=7.6 Hz, 1H), 1.47 (s, 3H), 0.68-0.65 (m, 3H).

Step 4: To a solution of compound 5d (109.96 mg, 566.11 μmol, 10.0 eq; the preparation of compound 5d may be referred to WO2022256842A1, pp. 110-113), compound 5c (20.0 mg, 56.61 μmol, 1.0 eq), and N-methylimidazole (46.48 mg, 566.11 μmol, 10.0 eq) in acetonitrile (4.0 mL) was added N,N,N',N'-tetramethylchloroformamidinium hexafluorophosphate (31.77 mg, 113.22 μmol, 2.0 eq.) in batches, and the reaction mixture was stirred for 16 h at 20° C. The LCMS detection showed that the product was formed, and then 50.0 mL of water was added to the reaction solution, and the pH was adjusted to 7 to 8 with dilute hydrochloric acid and it was extracted three times with ethyl acetate (100 mL). The organic phases were combined, washed with saturated saline, dried over anhydrous sodium sulfate, filtered, and the filtrate was concentrated under vacuum, and the residue was purified by prep-HPLC (column: Welch Xtimate C18 250*30 mm*10 um; mobile phase: water (0.05% HCl)-ACN; gradient: 50%-80%, 15 min; flow rate: 40 mL/min) to give a white solid compound 5e (20.0 mg, 66.7% yield).

MS (ESI): m/z calculated [M+H$^+$]: 530.20, measured: 530.2.

Step 5: To a solution of compound 5d (20 mg, 37.02 μmol, 1.0 eq.) in dichloromethane (1.0 mL) was added TFA (84.41 mg, 740.31 μmol, 20 eq.) at 20° C. The reaction mixture was stirred at 20° C. for 16 h. LCMS detection showed that the reaction was complete, and the reaction solution was concentrated to dryness under vacuum. A small amount of methanol was added to the residue to dissolve it and the pH was adjusted to 8 with saturated sodium bicarbonate solution. The resulting solution was purified by RP-TLC (C18, ACN: $H_2O$=3:1) to give a white solid compound 5 (5.00 mg, 27.6% yield).

MS (ESI): m/z calculated [M+H$^+$]: 490.17, measured: 490.2.

$^1$H NMR (400 MHz, chloroform-d) δ 9.06 (s, 1H), 8.55 (d, J=2.4 Hz, 1H), 8.11 (dd, J=8.5, 2.4 Hz, 1H), 7.31 (d, J=8.5 Hz, 1H), 7.11 (t, J=7.3 Hz, 1H), 6.90 (q, J=8.8 Hz, 1H), 4.79 (t, J=4.8 Hz, 1H), 4.41 (d, J=10.5 Hz, 1H), 4.07-3.99 (m, 1H), 3.95 (d, J=2.6 Hz, 3H), 3.89 (dd, J=11.4, 3.8 Hz, 1H), 3.73 (dd, J=11.3, 5.6 Hz, 1H), 2.60 (d, J=7.8 Hz, 1H), 1.59 (s, 3H), 0.79-0.68 (m, 3H).

Example 4: Synthesis of (2R,3S,4S,5R)-3-(3,4-difluoro-2-methoxyphenyl)-aza-(6-((R)-1,2-dihydroxyethyl)pyridin-3-yl)-4,5-dimethyl-5-(trifluoromethyl) pyrrolidine-2-carboxamide (6)

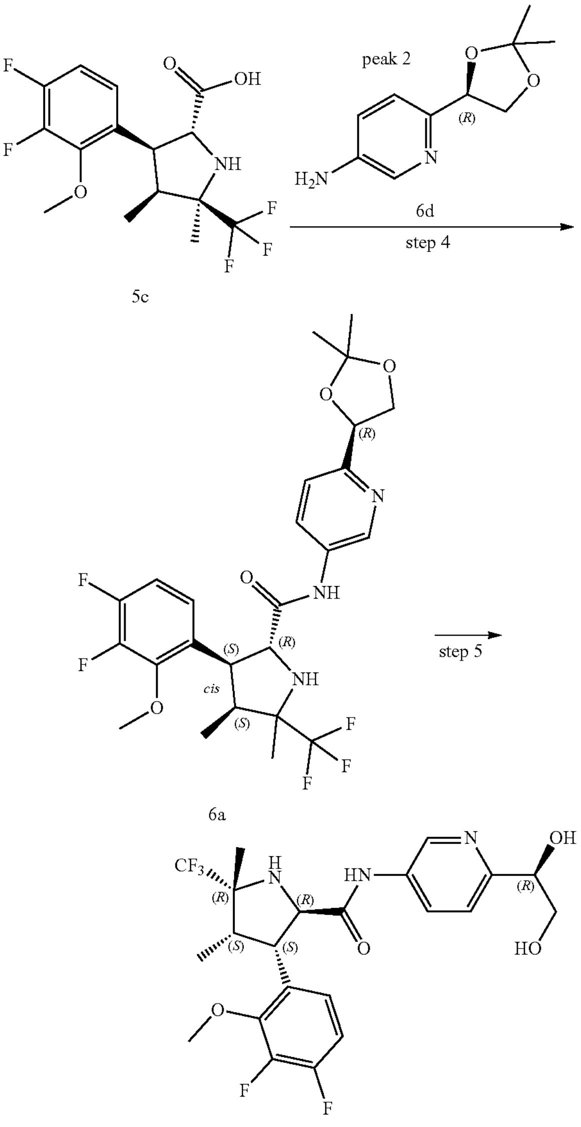

5c 6a 6

Step 1: To a solution of compound 6d (109.96 mg, 566.11 μmol, 10.0 eq.; the preparation of compound 6d may be referred to WO2022256842A1, pp. 110-113), compound 5c (20.0 mg, 56.61 μmol, 1.0 eq.) and N-methylimidazole (46.48 mg, 566.11 μmol, 10.0 eq.) in acetonitrile (4.0 mL) was added N,N,N',N'-tetramethylchloroformamidinium hexafluorophosphate (31.77 mg, 113.22 μmol, 2.0 eq.) in batches, and the reaction mixture was stirred for 16 h at 20° C. The LCMS detection showed that the product was formed, and then 50.0 mL of water was added to the reaction solution, and the pH was adjusted to 7 to 8 with dilute hydrochloric acid and it was extracted three times with ethyl acetate (100 mL). The organic phases were combined, washed with saturated saline, dried over anhydrous sodium sulfate, filtered, and the filtrate was concentrated under vacuum, and the residue was purified by prep-HPLC (column: Welch Xtimate C18 250*30 mm*10 um; mobile phase: water (0.05% HCl)-ACN; gradient: 50%-80%, 15 min; flow rate: 40 mL/min) to give a white solid compound 6a (14.2 mg, 47.3% yield).

MS (ESI): m/z calculated [M+H$^+$]: 530.20, measured: 530.2.

Step 2: To a solution of compound 6a (14.2 mg, 26.82 μmol, 1.0 eq.) in dichloromethane (0.7 mL) was added TFA (61.15 mg, 536.34 μmol, 20 eq.) at 20° C. and the reaction mixture was stirred at 20° C. for 16 h. LCMS detection showed that the reaction was complete, and the reaction solution was concentrated to dryness under vacuum. A small amount of methanol was added to the residue to dissolve it and the pH was adjusted to 8 with saturated sodium bicarbonate solution and the resulte solution was purified by RP-TLC (C18, ACN: $H_2O$=3:1) to give a white solid compound 6 (3.50 mg, 26.7% yield).

MS (ESI): m/z calculated [M+H$^+$]: 490.17, measured: 490.2.

$^1$H NMR (400 MHz, chloroform-d) δ9.03 (s, 1H), 8.55 (d, J=2.5 Hz, 1H), 8.12 (dd, J=8.6, 2.5 Hz, 1H), 7.31 (d, J=8.6 Hz, 1H), 7.11 (t, J=7.3 Hz, 1H), 6.91 (q, J=8.8 Hz, 1H), 4.79 (t, J=4.7 Hz, 1H), 4.41 (d, J=10.5 Hz, 1H), 4.02 (t, J=9.5 Hz, 1H), 3.95 (d, J=2.6 Hz, 3H), 3.90 (dd, J=11.3, 3.8 Hz, 1H), 3.74 (dd, J=11.3, 5.6 Hz, 1H), 2.59 (t, J=7.9 Hz, 1H), 1.59 (s, 3H), 0.74 (d, J=6.7 Hz, 3H).

Example 5: Synthesis of 3-((2R,3S,4S,5R)-3-(3,4-difluoro-2-methoxyphenyl)-4,5-dimethyl-5-(trifluoromethyl)pyrrolidine-2-carboxamido)pyridine 1-oxide (7)

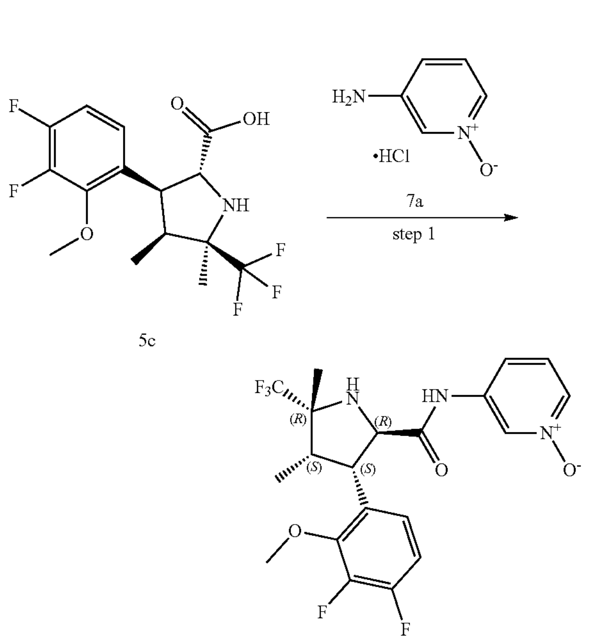

5c

7

Step 1: To a solution of 3-aminopyridine 1-oxide hydrochloride 7a (165.95 mg, 1.13 mmol, 20.0 eq.), compound 5c (20.0 mg, 56.61 μmol, 1.0 eq.), and N-methylimidazole (139.43 mg, 1.70 mmol, 30.0 eq.) in acetonitrile (4.0 mL) was added N,N,N',N'-tetramethylformamidinum hexafluorophosphate (31.77 mg, 113.22 μmol, 2.0 eq.) in batches, and the reaction mixture was stirred at 20° C. for 16 h. LCMS detection showed that a product was generated, and then 50.0 mL of water was added to the reaction solution, the pH was adjusted to 7 to 8 with dilute hydrochloric acid, and the reaction solution was extracted with ethyl acetate (100 mL) three times. The organic phases were combined, washed with saturated brine, dried over anhydrous sodium sulfate, filtered, and the filtrate was concentrated under vacuum, and the residue was purified by prep-HPLC (column: Welch Xtimate C18 250*30 mm*10 um; mobile phase: water (0.05% HCl)-ACN; gradient: 30%-60%, 15 min; flow rate: 40 mL/min) to give a white solid compound 7 (11.0 mg, 43.63% yield).

MS (ESI): m/z calculated [M+H$^+$]: 446.14, measured: 446.1.

$^1$H NMR (400 MHz, DMSO-$d_6$) δ 10.72 (s, 1H), 8.74 (t, J=1.8 Hz, 1H), 8.04 (dd, J=6.4, 1.8, 0.9 Hz, 1H), 7.53 (dd, J=8.6, 1.9, 0.9 Hz, 1H), 7.41 (dd, J=8.5, 6.3 Hz, 1H), 7.26-7.10 (m, 2H), 4.25 (d, J=8.3 Hz, 1H), 3.96 (d, J=8.3 Hz, 1H), 3.96 (d, J=8.3, 6.3 Hz, 1H) 6.3 Hz, 1H), 7.26-7.10 (m, 2H), 4.25 (d, J=8.3 Hz, 1H), 3.96 (d, J=8.2 Hz, 1H), 3.91 (d, J=1.9 Hz, 3H), 2.58 (q, J=7.5 Hz, 1H), 1.52 (s, 3H), 0.72-0.61 (m, 3H).

Example 6: Synthesis of (2R,3S,4S,5R)-3-(3,4-difluoro-2-methoxyphenyl)-4,5-dimethyl-aza-(3-aminosulfonylphenyl)-5-(trifluoromethyl)pyrrolidine-2-carboxamide (8)

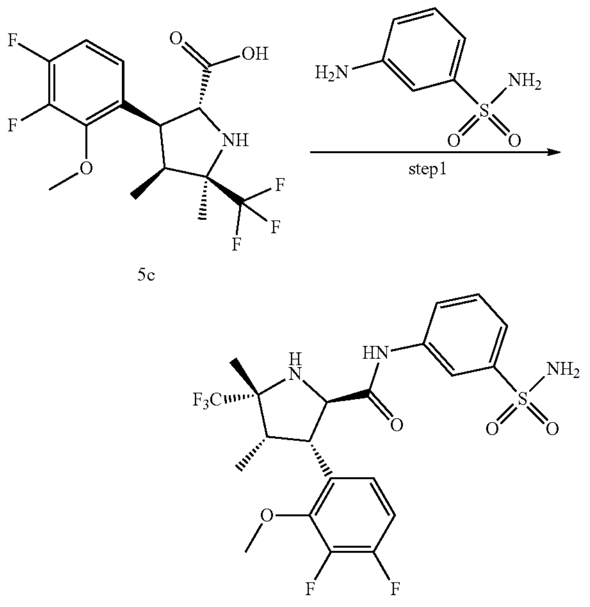

5c

8

Step 1: To a solution of 3-aminobenzenesulfonamide (97.48 mg, 566.11 μmol, 10.0 eq.), compound 5c (20.0 mg, 56.61 μmol, 1.0 eq.) and N-methylimidazole (46.48 mg, 566.11 mol, 10.0 eq.) in acetonitrile (5.0 mL) was added N,N,N',N'-tetramethylchloroformamidinium hexafluorophosphate (31.77 mg, 113.22 μmol, 2.0 eq.) in batches, and the reaction mixture was stirred at 20° C. for 16 h. LCMS detection showed that a product was generated, and then 50.0 mL of water was added to the reaction solution, the pH was adjusted to 7 to 8 with dilute hydrochloric acid, and the solution was extracted with ethyl acetate (100 mL) three times. The organic phases were combined, washed with saturated saline, dried over anhydrous sodium sulfate, filtered, and the filtrate was concentrated under vacuum, and the residue was purified by prep-HPLC (column: Welch Xtimate C18 250*30 mm*10 um; mobile phase: water (0.05% HCl)-ACN; gradient: 30%-60%, 15 min; flow rate: 40 mL/min) to give a white solid compound 8 (4.50 mg, 15.66% yield).

MS (ESI): m/z calculated [M+H$^+$]: 508.13, measured: 508.3.

$^1$H NMR (400 MHz, DMSO-d6) δ 10.52 (s, 1H), 8.17 (s, 1H), 7.72 (dt, J=6.8, 2.3 Hz, 1H), 7.55-7.44 (m, 2H), 7.36 (s, 2H), 7.29-7.10 (m, 2H), 4.26 (d, J=8.8 Hz, 1H), 3.96 (t, J=8.4 Hz, 1H), 3.91 (d, J=2.1 Hz, 3H), 2.58 (q, J=7.4 Hz, 1H), 1.53 (s, 3H), 0.75-0.63 (m, 3H).

Example 7: Synthesis of (2R,3S,4S,5R)-3-(3,4-difluoro-2-methoxyphenyl)-4,5-dimethyl-aza-(2-aminosulfonylpyridin-4-yl)-5-(trifluoromethyl)pyrrolidine-2-carboxamide (9)

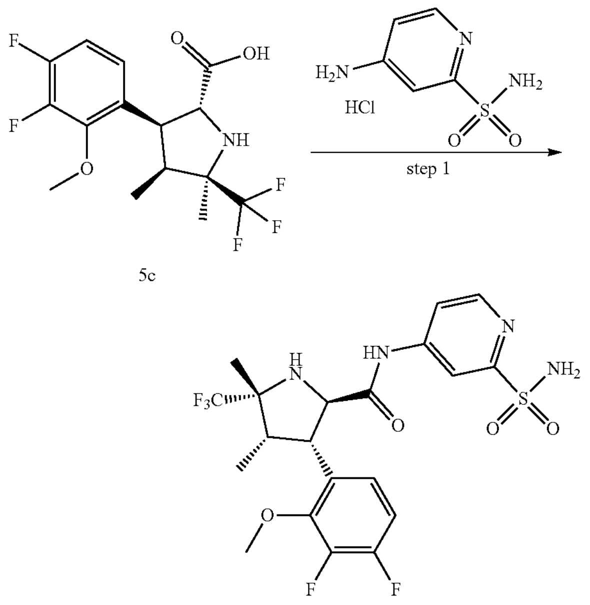

5c

9

Step 1: To a solution of 4-amino-2-pyridinesulfonamide hydrochloride (118.68 mg, 566.11 μmol, 10.0 eq. 1.0 eq.; the preparation of 4-amino-2-pyridinesulfonamide hydrochloride may be referred to *J. Med. Chem.* 1980, 23, 12, 1376-1380), compound 5c (20.0 mg, 56.61 mol, 1.0 eq.) and N-methylimidazole (92.95 mg, 1.13 mmol, 20.0 eq.) in N,N-dimethylformamide (3.0 mL) was added acetonitrile (1.0 mL), then N,N,N',N'-tetramethylchloroformamidinium hexafluorophosphate (31.77 mg, 113.22 μmol, 2.0 eq.) was added in batches, and the reaction mixture was stirred at 20° C. for 16 h. LCMS detection showed the formation of product, then 50.0 mL of water was added to the reaction solution, the pH was adjusted to 7 to 8 with dilute hydrochloric acid, and the solution was extracted with ethyl acetate (100 mL) three times. The organic phases were combined, washed with saturated saline, dried over anhydrous sodium sulfate, filtered, and the filtrate was concentrated under vacuum, and the residue was purified by prep-HPLC (column model: Welch Xtimate C18 250*30 mm*10 um; mobile phase: water (0.05% HCl)-ACN; gradient: 20-50%, 15 min; flow rate: 40 mL/min) to give a white solid compound 9 (9.30 mg, 32.31% yield).

MS (ESI): m/z calculated [M+H$^+$]: 509.12, measured: 509.2.

$^1$H NMR (400 MHz, DMSO-$d_6$+drop $D_2O$) δ 7.97 (d, J=6.8 Hz, 1H), 7.23-7.14 (m, 2H), 7.13 (d, J=2.5 Hz, 1H), 6.77 (dd, J=6.8, 2.5 Hz, 1H), 4.34 (d, J=9.7 Hz, 1H), 4.02 (dd, J=9.8, 7.6 Hz, 1H), 3.90 (d, J=1.8 Hz, 3H), 2.59 (q, J=7.4 Hz, 1H), 1.58 (s, 3H), 0.71-0.57 (m, 3H).

Example 8: Synthesis of (2R,3S,4S,5R)-3-(3,4-difluoro-2-methoxyphenyl)-aza-(4-fluoro-3-(aza-hydroxycarbamimidoyl)phenyl)-4,5-dimethyl-5-(trifluoromethyl)pyrrolidine-2-carboxamide hydrochloride (10)

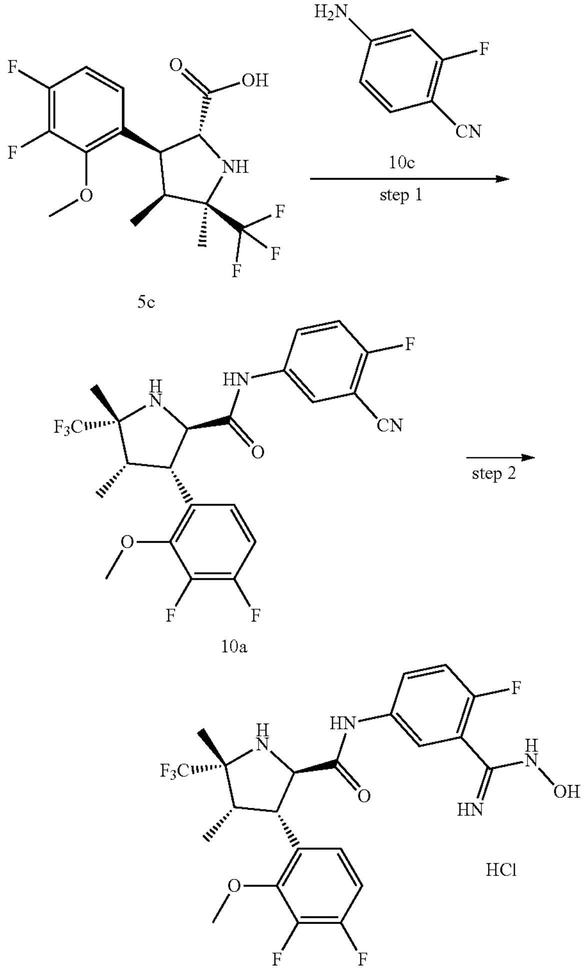

5c

10a

10

Step 1: To a solution of 4-amino-2-fluorobenzonitrile 10c (963.3 mg, 7.8 mmol, 50.0 eq.), compound 5c (50.0 mg, 141.53 μmol, 1.0 eq.), and N-methylimidazole (116.19 mg, 1.42 mmol, 10.0 eq.) in acetonitrile (5.0 mL) was added N,N,N',N'-tetramethylchloroformamidinium hexafluorophosphate (79.42 mg, 283.05 μmol, 2.0 eq.) in batches, and the reaction mixture was stirred at 20° C. for 16 h. The LCMS detection showed the formation of a product, and then 50.0 mL of water was added to the reaction solution, and the pH was adjusted to 6 to 7 with dilute hydrochloric acid, and the reaction solution was extracted with ethyl acetate (100 mL) three times. The organic phases were combined, washed with saturated saline, dried over anhydrous sodium sulfate, filtered, and the filtrate was concentrated under vacuum, and the residue was purified by prep-HPLC (column: Welch Xtimate C18 250*30 mm*10 um; mobile phase: water (0.05% HCl)-ACN; gradient: 50%-80%, 15 min; flow rate: 40 mL/min) to give a white solid compound 10a (35.0 mg, 52.46% yield).

MS (ESI): m/z calculated [M+H$^+$]: 472.14, measured: 472.2.

Step 2: Compound 10a (35.0 mg, 74.25 μmol, 1.0 eq.), hydroxylamine hydrochloride (15.48 mg, 222.74 μmol, 3.0 eq.) and triethylamine (67.62 mg, 668.22 μmol, 9.0 eq.) were added to ethanol (0.5 mL) and heat to reflux for 2 h. LCMS detection showed that the reaction was complete. The reaction solution was concentrated to dryness under vacuum. A small amount of methanol was added to the residue to dissolve it, and the pH was adjusted to 3 with dilute hydrochloric acid, and the resulting solution was purified by prep-HPLC (column model: YMC-Triart Prep C18 150*30 mm*10 um; mobile phase: water (0.05% HCl)-ACN; gradient: 30%-60%, 15 min; flow rate: 40 mL/min) to give a white solid compound 10 (19.7 mg, 52.60% yield).

MS (ESI): m/z calculated [M+H$^+$]: 505.16, measured: 505.3.

$^1$H NMR (400 MHz, DMSO-$d_6$) δ 13.03 (s, 1H), 11.44 (s, 1H), 10.90 (s, 1H), 9.29 (s, H), 7.96 (dd, J=6.1, 2.7 Hz, 1H), 7.87 (ddd, J=9.1, 4.6, 2.7 Hz, 1H), 7.44 (t, J=9.3 z, 1H), 7.37-7.29 (m, 1H), 7.14 (td, J=9.4, 7.8 Hz, 1H), 4.37 (d, J=9.1 Hz, 1H), 3.97 (t, J=8.5 Hz, 1H), 3.91 (d, J=2.0 Hz, 3H), 2.58 (q, J=7.6 Hz, 1H), 1.55 (s, 3H) 1.55 (s, 3H), 0.77-0.57 (m, 3H).

Example 9: Synthesis of 4-((2R,3S,4S,5R)-3-(3,4-difluoro-2-(methoxy-d3)phenyl)-4,5-dimethyl-5-(trifluoromethyl)pyrrolidine-2-carboxamido)pyridinamide (11)

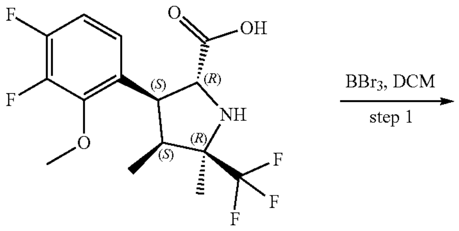

5c

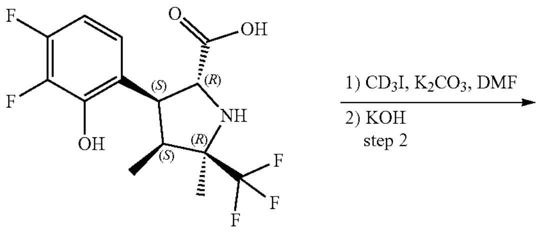

11a

-continued

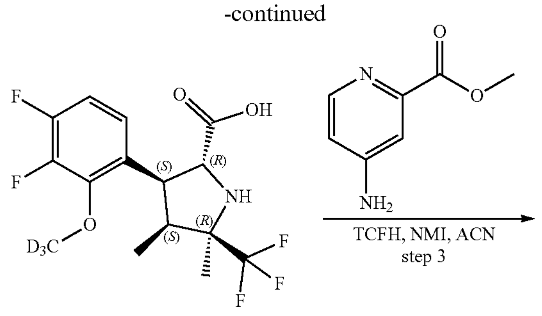

11b

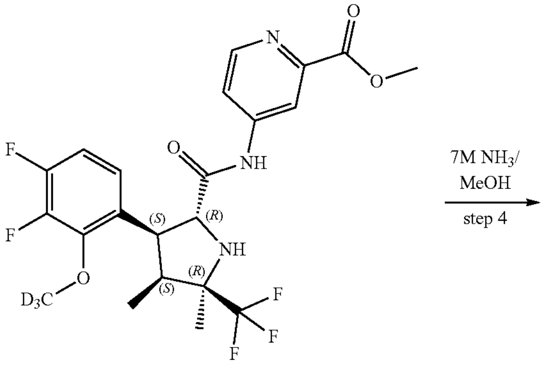

11c

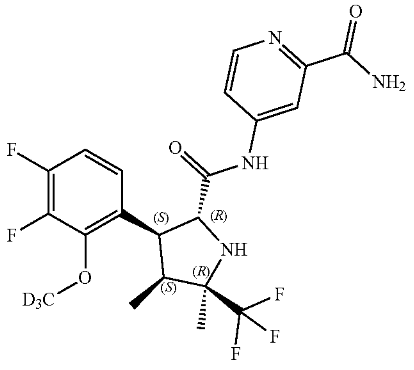

11

Step 1: To a solution of compound 5c (50.0 mg, 141.53 μmol, 1.0 eq.) in dichloromethane (0.2 mL) was added boron tribromide (0.42 mL, 424.58 μmol, 3.0 eq., 1 mol/L solution in dichloromethane) dropwise at 0° C., the reaction mixture was naturally heated up to 20° C. and stirred for 16 h. LCMS detection showed that a product was formed. The reaction solution was concentrated to dryness under vacuum and the residue was purified by prep-HPLC (column: Synergi Max-RP 250*40 mm*10 um; mobile phase: water (0.05% HCl)-ACN; gradient: 30%-60%, 15 min; flow rate: 60 mL/min) to give a white solid compound 11a (25.0 mg, 52.07% yield). 52.07% yield).

MS (ESI): m/z calculated [M+H$^+$]: 340.09, measured: 340.2.

Step 2: Compound 11a (25.0 mg, 73.69 μmol, 1.0 eq.) and potassium carbonate (30.55 mg, 221.07 μmol, 3.0 eq.) in N,N-dimethylformamide (0.3 mL) were stirred at room temperature for 30 min. Then deutero-iodomethane (26.71 mg, 184.22 μmol, 2.5 eq.) was added. Stirring was then continued at room temperature for 3 h. LCMS detection showed that the raw material was consumed, potassium hydroxide (0.37 mL, 1.11 mmol, 15.0 eq., 3 mol/L aqueous solution) was added to the reaction mixture, and then the temperature was raised to 50° C. and stirred for 2 h. LCMS detection showed that the hydrolysis was complete. The reaction solution was cooled down to 5° C., and the pH was adjusted to 2 with dilute hydrochloric acid, then it was extracted with ethyl acetate (5.0 mL) three times. The organic phases were combined, washed with saturated saline, dried over anhydrous sodium sulfate, and concentrated under vacuum, and the residue was purified by prep-HPLC (column model: Welch Xtimate C18 250*30 mm*Oum; mobile phase: water (0.05%)-ACN). HCl-ACN; mobile phase: water (0.05% HCl)-ACN; gradient: 30%-60%, 15 min; flow rate: 40 mL/min) to give a white solid compound 11b (15.0 mg, 57.13% yield).

MS (ESI): m/z calculated [M+H$^+$]: 357.12, measured: 357.2.

$^1$H NMR (400 MHz, DMSO-d$_6$) δ 7.26-7.21 (m, 1H), 7.19-7.08 (m, 1H), 4.26 (d, J=9.3 Hz, 1H), 3.93 (t, J=8.6 Hz, 1H), 2.55-2.51 (m, 1H), 1.51 (s, 3H), 0.79-0.57 (m, 3H). 0.57 (m, 3H).

Step 3: To a solution of methyl 4-aminopyridine-2-carboxylate (222.05 mg, 1.46 mmol, 40.0 eq.), compound 11b (13.0 mg, 36.49 μmol, 1.0 eq.), and N-methylimidazole (29.95 mg, 364.85 μmol, 10.0 eq.) in acetonitrile (2.0 mL) was added N,N,N',N'-tetramethylchloroformamidinium hexafluorophosphate (20.47 mg, 72.97 μmol, 2.0 eq.) in batches, and the reaction mixture was stirred at 20° C. for 16 h. The LCMS detection showed that the raw material was consumed, 100.0 mL of water was added to the reaction solution, and the pH was adjusted to 7 to 8 with dilute hydrochloric acid, and the reaction solution was then extracted with ethyl acetate (50 mL) three times. The organic phases were combined, washed with saturated saline, dried over anhydrous sodium sulfate, and concentrated under vacuum, and the residue was purified by prep-HPLC (column model: Welch Xtimate C18 250*30 mm*10 um; mobile phase: water (0.05% HCl)-ACN; gradient: 30%-60%, 15 min; flow rate: 40 mL/min) to give white solid compound 11c (2.8 mg, 15.65% yield).

MS (ESI): m/z calculated [M+H$^+$]: 491.17, measured: 491.2.

Step 4: Compound 11c (2.80 mg, 5.71 μmol, 1.0 eq.) was dissolved in 7 M $NH_3$/MeOH solution (2.0 mL) and stirred at 20° C. for 16 h. The LCMS detection showed that the raw material was consumed, and the reaction solution was concentrated to dryness under vacuum, and the residue was purified by RP-TLC (C18, ACN: 0.5% HCl=3:1, $R_f$=0.5) to give a white solid compound 11 (0.82 mg, 30.21% yield).

MS (ESI): m/z calculated [M+H$^+$]: 476.17, measured: 476.2.

$^1$H NMR (400 MHz, methanol-d$_4$) δ 8.40 (d, J=5.5 Hz, 1H), 8.12 (d, J=2.1 Hz, 1H), 7.78 (dd, J=5.5, 2.1 Hz, 1H), 7.18-7.09 (m, 1H), 6.96-6.85 (m, 1H), 4.24 (d, J=9.8 Hz, 1H), 4.03 (t, J=9.1 Hz, 1H), 2.56 (p, J=8.1 Hz, 1H), 1.52 (s, 3H), 0.70 (dt, J=7.4, 2.5 Hz, 3H).

Example 10: Synthesis of (2R,3S,4S,5R)-3-(3,4-difluoro-2-methoxyphenyl)-4,5-dimethyl-N-(2-(methylsulfonyl)pyridin-4-yl)-5-(trifluoromethyl)pyrrolidine-2-carboxamide (12)

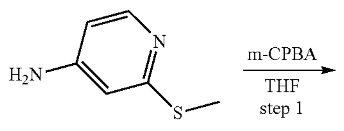

12a

-continued

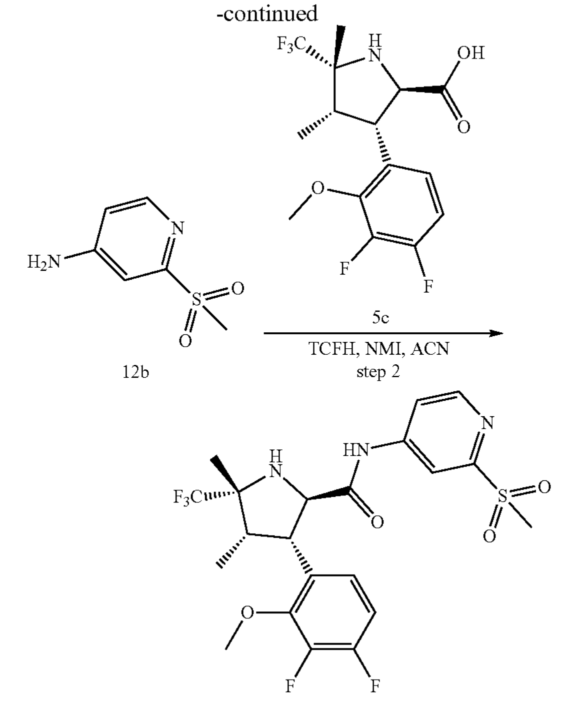

12b

12

Step 1: To a solution of 2-(methylthio)-4-aminopyridine 12a (450.0 mg, 3.05 mmol, 1.0 eq.) in tetrahydrofuran (10.0 mL) was added m-chloroperoxybenzoic acid (1.86 mg, 9.15 mmol, 3.0 eq.) in batches at room temperature, and the reaction mixture was stirred for 3 h at 20° C. LCMS detection showed that the reaction was complete. The reaction solution was directly wet-sampled and purified by silica gel column purification (100% ethyl acetate, $R_f$=0.5) to give a yellow solid compound 12b (380.0 mg, 72.37% yield).

MS (ESI): m/z calculated [M+H$^+$]: 173.03, measured: 172.9.

$^1$H NMR (400 MHz, DMSO-d$_6$) δ 8.10 (d, J=5.6 Hz, 1H), 7.14 (d, J=2.3 Hz, 1H), 6.72 (s, 2H), 6.66 (dd, J=5.6, 2.3 Hz, 1H), 3.15 (s, 3H).

Step 2: To a solution of compound 12b (341.19 mg, 1.98 mmol, 20.0 eq.), compound 5c (35.0 mg, 99.07 μmol, 1.0 eq.) and N-methylimidazole (162.67 mg, 1.98 mmol, 2.0 eq.) in acetonitrile (2.0 mL) was added N,N,N',N'-tetramethylchloroformamidinium hexafluorophosphate (55.59 mg, 198.14 μmol, 2.0 eq.) in batches, and the reaction mixture was stirred at 20° C. for 16 h. LCMS detection showed that the product was generated, and then 50.0 mL of water was added to the reaction solution, and the pH was adjusted to 7 to 8 with dilute hydrochloric acid, then it was extracted with ethyl acetate (30.0 mL) for three extractions. The organic phases were combined, washed with saturated saline, dried over anhydrous sodium sulfate, filtered, and the filtrate was concentrated under vacuum, and the residue was purified by prep-HPLC (column: Welch Xtimate C18 250*30 mm*10 um; mobile phase: water (0.05% HCl)-ACN; gradient: 50%-80%, 15 min; flow rate: 40 mL/min) to give a white solid compound 12 (2.14 mg, 4.26% yield).

MS (ESI): m/z calculated [M+H$^+$]: 508.13, measured: 508.1.

$^1$H NMR (400 MHz, DMSO-d$_6$) δ 11.09 (s, 1H), 8.62 (d, J=5.5 Hz, 1H), 8.36 (s, 1H), 7.84 (d, J=6.8 Hz, 1H), 7.24-7.14 (m, 2H), 4.30 (d, J=7.5 Hz, 1H), 3.99 (t, J=8.2 Hz, 1H), 3.91 (s, 3H), 3.24 (s, 3H), 2.62-2.55 (m, 1H), 1.53 (s, 3H), 0.82-0.57 (m, 3H).

Example 11: Synthesis of 4-((2R,3S,4S,5R)-3-(2-(difluoromethoxy)-3,4-difluorophenyl)-4,5-dimethyl-5-(trifluoromethyl)pyrrolidine-2-carboxamido)pyridinamide (13)

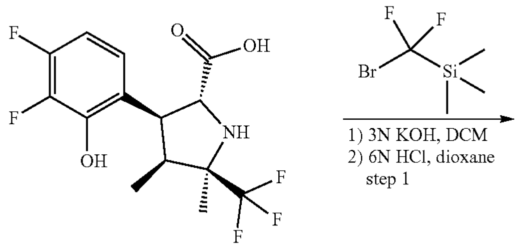

11a

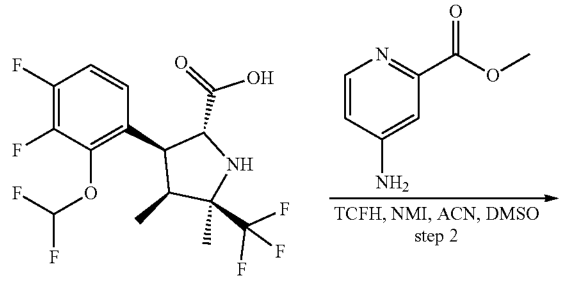

13a

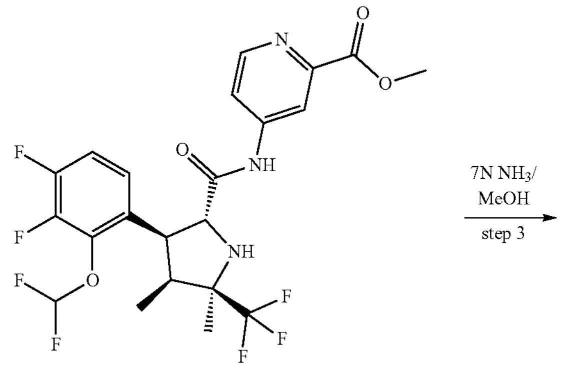

13b

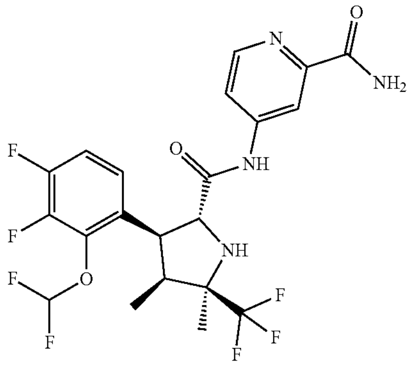

13

Step 1: To a solution of compound 11a (26.0 mg, 76.64 mmol, 1.0 eq.) in dichloromethane (2.0 mL) was added 3 mol/L KOH aqueous solution (0.072 mL, 1.15 mmol, 15.0 eq.), after cooling down to 0° C., difluorobromomethyltrimethylsilane (63.53 mg, 98% purity. 306.55 μmol, 4.0 eq.) was added, and the reaction mixture was naturally warmed to 20° C. and stirred for 16 hours. The dichloromethane was then evaporated under reduced pressure and 1,4-dioxane (1.0 mL) and 6 mol/L aqueous hydrochloric acid (1.0 mL) were added to the residue, and the resulting mixture was warmed to 60° C. and stirred for 16 h. LCMS detection showed that most of the starting materials were transformed to product. The reaction mixture was concentrated to dryness under vacuum and the residue was purified by prep-HPLC (column model: Welch Xtimate C18 150*30 mm*10 um; mobile phase: water (0.05% HCl)-ACN; gradient: 30%-60% for 15 min; flow rate: 40 mL/min) to give a white solid compound 13a (12.0 mg, 40.22% yield).

MS (ESI): m/z calculated [$M+H^+$]: 390.09, measured: 390.1.

$^1H$ NMR (400 MHz, DMSO-d6) δ 12.77 (s, 1H), 7.48-7.33 (m, 2H), 7.26 (s, 0.6H), 7.08 (s, 0.4H), 4.22 (d, J=9.3 Hz, 1H), 3.90 (t, J=8.6 Hz, 1H), 2.48 (d, J=7.5 Hz, 1H), 1.47 (s, 3H), 0.81-0.61 (m, 3H). 2.48 (d, J=7.5 Hz, 1H), 1.47 (s, 3H), 0.81-0.61 (m, 3H).

Step 2: To a solution of methyl 4-aminopyridine-2-carboxylate (143.58 mg, 924.81 mol, 30.0 eq.), compound 13a (12.0 mg, 30.83 μmol, 1.0 eq.) and N-methylimidazole (51.13 mg, 616.54 μmol, 20.0 eq.) in acetonitrile (1.0 mL) was added N,N,N',N'-tetramethylchloroformamidinium hexafluorophosphate (17.65 mg, 61.65 μmol, 2.0 eq.) in batches, and the reaction mixture was stirred at 20° C. for 16 h. LCMS detection showed the product was produced, and then 50.0 mL of water was added to the reaction solution, and the pH was adjusted to 7 to 8 with dilute hydrochloric acid, then it was extracted with ethyl acetate (30.0 mL) three times. The organic phases were combined, washed with saturated saline, dried over anhydrous sodium sulfate, filtered, and the filtrate was concentrated under vacuum, and the residue was purified by prep-HPLC (column: Welch Xtimate C18 250*30 mm*10 um; mobile phase: water (0.05% HCl)-ACN; gradient: 30%-60%, 15 min; flow rate: 40 mL/min) to give a white solid compound 13b (8.0 mg, 49.58% yield).

MS (ESI): m/z calculated [$M+H^+$]: 524.13, measured: 524.1.

Step 3: Compound 13b (8.0 mg, 15.28 μmol, 1.0 eq.) was dissolved in 7 M $NH_3$/MeOH solution (1.0 mL) and stirred at 20° C. for 16 h. The LCMS detection showed that the raw material was consumed, the reaction solution was concentrated to dryness under vacuum and the residue was purified by RP-TLC (C18, ACN: 0.5% HCl=3:1, $R_f$=0.5) to give a white solid compound 13 (1.80 mg, 23% yield).

MS (ESI): m/z calculated [$M+H^+$]: 509.13, measured: 509.2.

$^1H$ NMR (400 MHz, methanol-$d_4$) δ 8.71-8.54 (m, 2H), 8.21 (dd, J=6.4, 2.4 Hz, 1H), 7.47-7.22 (m, 2H), 6.91 (t, J=72.8 Hz, 1H), 4.51 (d, J=9.1 Hz, 1H), 4.24 (t, J=8.9 Hz, 1H), 2.71 (q, J=7.6 Hz, 1H), 1.63 (s, 3H), 0.93-0.77 (m, 3H).

Example 12: Synthesis of (2R,3S,4S,5R)-3-(3,4-difluoro-2-(methoxy-d3)phenyl)-N-(4-fluoro-3-(N-hydroxycarbamimidoyl)phenyl)-4,5-dimethyl-5-(trifluoromethyl)pyrrolidine-2-carboxamide (14)

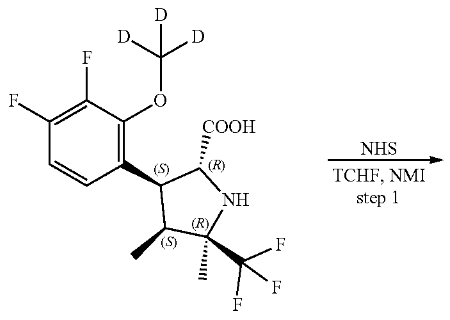

11b

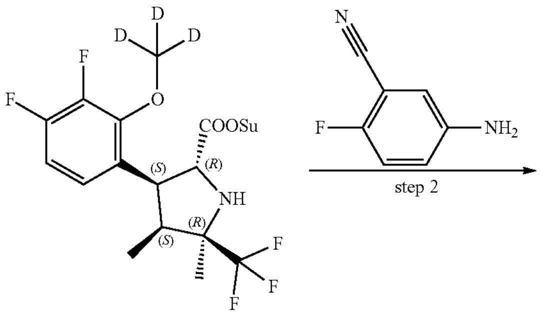

14a

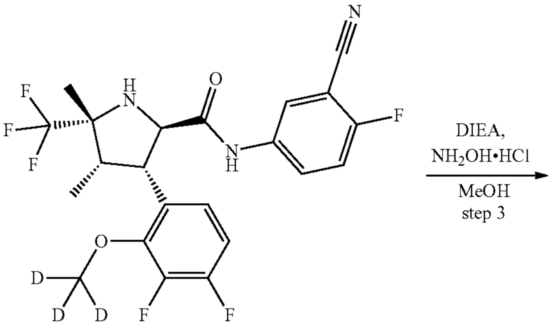

14b

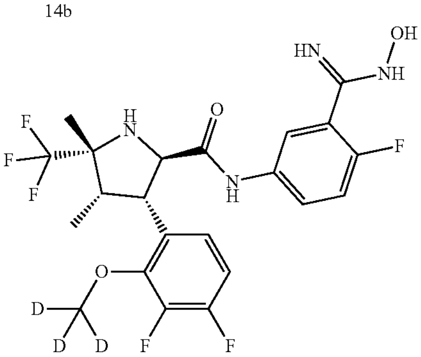

14

Step 1: To a solution of N-hydroxybutanediimide (3.96 g, 98% purity, 33.68 mmol, 1.5 eq., Bidet's Reagent), compound 11b (8.0 g, 22.45 mmol, 1.0 eq.) and N-methylimidazole (5.64 g, 98% purity, 67.36 mmol, 3.0 eq.) in acetonitrile (120.0 mL) solution was added N,N,N',N'-tetramethylchloroformamidinium hexafluorophosphate (9.64 g, 98% purity, 33.68 mmol, 1.5 eq.) in batches in ice bath and the addition process was exothermic. After addition the system was automatically warmed to room temperature and the reaction mixture was stirred at room temperature for 2 h. LCMS detection showed that the raw material was consumed. 500.0 mL of water was added to the reaction solution and the solution was extracted three times with ethyl acetate (150.0 mL). The organic phases were combined, washed with saturated saline, dried over anhydrous sodium sulfate, filtered, concentrated to dryness under vacuum, and the residue was purified by normal-phase silica gel column (petroleum ether:ethyl acetate=5:1) to give a white solid compound 14a (8.6 g, 84.48% yield).

MS (ESI): m/z Calcd. for [M+H$^+$]: 454.14, found: 454.2.

Step 2: Compound 14a (50.0 mg, 0.11 mmol, 1.0 eq.) was dissolved in tetrahydrofuran (1.0 mL) and 2-fluoro-5-aminobenzonitrile (74.87 mg, 0.55 mmol, 5.0 eq.) was added. The reaction mixture was heated to 70° C. and stirred for 16 h. LC-MS detection showed that most of the materials were consumed, and the reaction solution was concentrated under vacuum, then the residue was purified by normal-phase silica gel column (petroleum ether:ethyl acetate=2:1) to give a white solid compound 14b (20.0 mg, 38.23% yield).

MS (ESI): m/z Calcd. for [M+H$^+$]: 475.16, found: 474.7.

Step 3: To a solution of hydroxylamine hydrochloride (14.59 mg, 210.00 μmol, 5.0 eq.), N,N-diisopropylethylamine (27.14 mg, 210.00 μmol, 5.0 eq.) in methanol (1.0 mL) was added compound 14b (20.0 mg, 42.16 μmol, 1.0 eq.), and the reaction mixture was stirred for 16 hours at 25° C. The reaction solution was concentrated under vacuum and the residue was purified by prep-HPLC (column: Welch Xtimate C18, 21.2*150 mm, 5 um; mobile phase: Water (0.1% FA)-ACN; gradient: 45%-65%, 13 min; flow rate: 15 mL/min) to give a white solid compound 14 (17.6 mg, 82.3% yield).

MS (ESI): m/z Calcd. for [M+H$^+$]: 508.18, found: 508.44.

$^1$H NMR (400 MHz, DMSO-$d_6$) δ 10.26 (s, 1H), 9.61 (s, 1H), 7.71 (dd, J=6.5, 2.8 Hz, 1H), 7.61 (dd, J=8.9, 4.4, 2.8 Hz, 1H), 7.29-7.08 (m, 3H), 5.77 (s, 2H), 4.20 (dd, J=8.9, 6.3 Hz, 1H), 3.93 (t, J=8.5 Hz, 1H), 4.20 (t, J=8.5 Hz, 3.93) 5.77 (s, 2H), 4.20 (dd, J=8.9, 6.3 Hz, 1H), 3.93 (t, J=8.5 Hz, 1H), 3.01 (d, J=6.3 Hz, 1H), 2.57 (q, J=7.6 Hz, 1H), 1.52 (s, 3H), 0.80-0.60 (m, 3H).

Example 13: Synthesis of (2R,3S,4S,5R)-3-(3,4-difluoro-2-(methoxy-$d_3$)phenyl)-N-(2-(N-methoxycarbamimidoyl)pyridin-4-yl)-4,5-dimethyl-5-(trifluoromethyl)pyrrolidine-2-carboxamide (15)

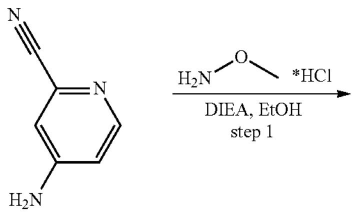

15a

-continued

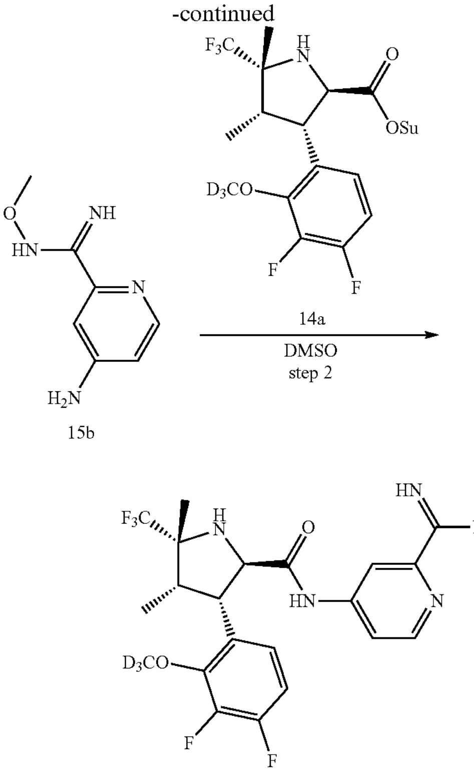

Step 1: To a solution of methylhydroxylamine hydrochloride 15a (70.16 mg, 840.04 mol, 2.0 eq.), triethylamine (127.50 mg, 1.26 mmol, 3.0 eq.) in ethanol (1.0 mL) were added compound 1 (50 mg, 419.74 μmol, 1.0 eq.) and mercaptoacetic acid (38.69 mg. 419.74 μmol, 1.0 eq.), and the reaction mixture was stirred at 65° C. for 16 h. LCMS detection showed that most of the raw materials were consumed and products were generated, and the reaction solution was concentrated under vacuum, then the residue was purified by a normal-phase silica gel column (petroleum ether:ethyl acetate=1:1, 0.5% of 7 M ammonia in methanol) to give a white solid compound 15b (55.0 mg, 78.85% yield).

MS (ESI): m/z Calcd. for $[M+H^+]$: 167.09, found: 167.1.

Step 2: Compound 15b (45.70 mg, 275.00 μmol, 5.0 eq.) and compound 14a (25 mg, 55.14 μmol, 1.0 eq.) were dissolved in dimethylsulfoxide (1.0 mL), and the reaction mixture was stirred at 100° C. for 16 h. Compound 14a was essentially consumed completely as monitored by LC-MS, and products were generated. 5 mL of water was added to the reaction system, the solution was extracted with ethyl acetate (8 mL*5), then the organic phases were combined and dried over saturated saline. The solvent was removed under reduced pressure, and the residue was purified by prep-HPLC (column model: Welch Xtimate C18, 21.2*150 mm, 5 um; mobile phase: Water (0.1% FA)-ACN; gradient: 55%-80%, 13 min; flow rate: 15 mL/min) to give a white solid compound 15 (0.75 mg, 2.70% yield).

MS (ESI): m/z Calcd. for $[M+H^+]$: 505.20, found: 505.49.

$^1$H NMR (400 MHz, DMSO-$d_6$) δ 10.62 (s, 1H), 8.42 (d, J=5.6 Hz, 1H), 8.06 (d, J=2.1 Hz, 1H), 7.67 (dd, J=5.6, 2.1 Hz, 1H), 7.25-7.08 (m, 2H), 6.05 (s, 2H), 4.23 (dd, J=8.2, 5.5 Hz, 1H), 3.96 (t, J=8.2 Hz, 1H), 3.96 (t, J=8.2 Hz, 1H) 6.05 (s, 2H), 4.23 (dd, J=8.2, 5.5 Hz, 1H), 3.96 (t, J=8.2 Hz, 1H), 3.78 (s, 3H), 3.22 (d, J=5.5 Hz, 1H), 2.59 (q, J=7.7 Hz, 1H), 1.53 (s, 3H), 0.78-0.61 (m, 3H).

Example 14: Synthesis of (2R,3S,4S,5R)-3-(3,4-difluoro-2-(methoxy-$d_3$)phenyl)-N-(2-(N-hydroxy-carbamimidoyl)pyridin-4-yl)-4,5-dimethyl-5-(trifluoromethyl)pyrrolidine-2-carboxamide (16)

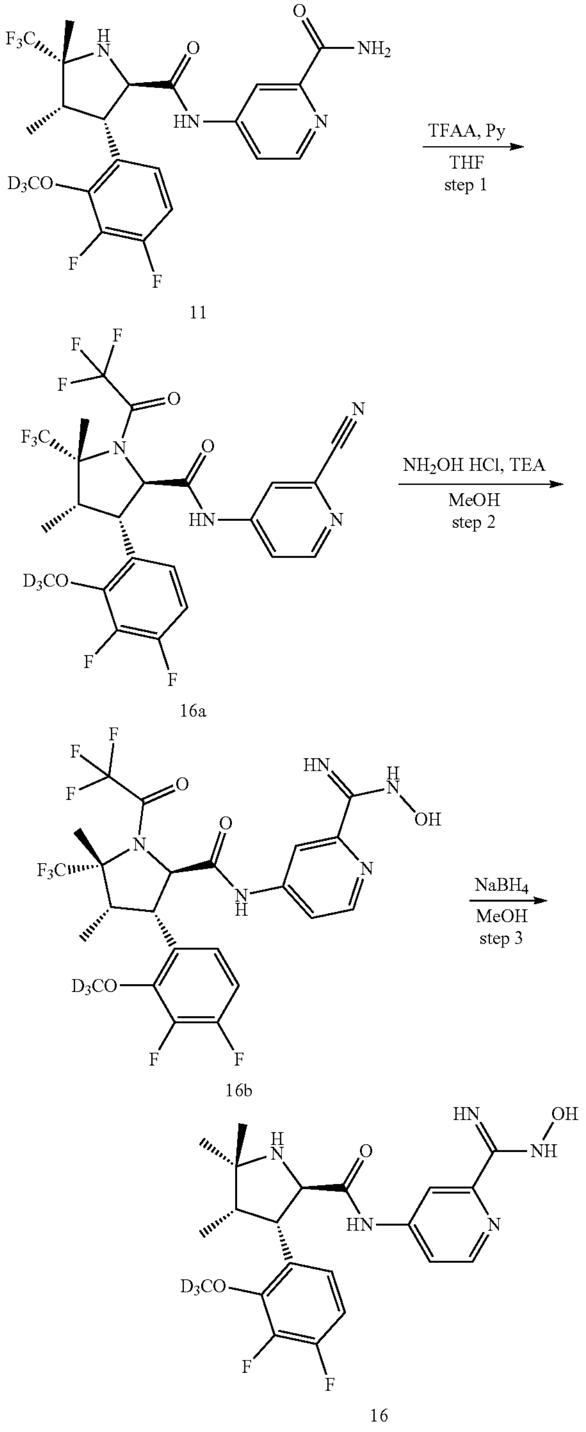

Step 1: Compound 11 (100.0 mg, 0.21 mmol, 1.0 eq.) was dissolved in tetrahydrofuran (2.0 mL), and the reaction atmosphere was purged with nitrogen gas three times, pyridine (156.14 mg, 1.97 mmol, 9.4 eq.), trifluoroacetic anhydride (207.30 mg, 0.99 mmol, 4.7 eq.) were added sequentially at 0° C. and the reaction mixture was stirred at 25° C. for 3 hours. LC-MS detection showed that the raw materials were consumed, then water (5.0 mL) was added, and the solution was extracted with ethyl acetate (10.0 mL*2), and washed with saturated saline (10.0 mL). The organic phases were combined, dried over sodium sulfate, concentrated under reduced pressure, and the residue was purified by a normal-phase silica gel column (petroleum ether:ethyl acetate=3:1) to give a yellow solid compound 16a (85.0 mg, 88.35% yield).

MS (ESI): m/z Calcd. for $[M+H^+]$: 554.14, found: 554.3.

Step 2: To a solution of hydroxylamine hydrochloride (62.54 mg, 900.00 μmol, 10.0 eq.), N,N-diisopropylethylamine (109.29 mg, 1.08 mmol, 12.0 eq.) in methanol (1.0 mL) was added compound 16a (50.0 mg, 90.35 μmol, 1.0 eq.), and the reaction mixture was stirred at 25° C. for 16 h. LCMS detection showed that most of the raw materials were consumed and products were generated. The reaction solution was concentrated under vacuum and the residue was purified by normal-phase silica gel column (petroleum ether: ethyl acetate=2:1) to give a white solid compound 16b (45 mg, 84.93% yield).

MS (ESI): m/z Calcd. for $[M+H^+]$: 587.17, found: 587.1.

Step 3: Compound 16b (30.0 mg, 51.16 μmol, 1.0 eq.) was dissolved in methanol (1.0 mL), then sodium borohydride (17.36 mg, 459.00 μmol, 9 eq.) was added in batches, and the reaction mixture was stirred at 25° C. for 22 h. The LC-MS detection showed that the product was generated, and the reaction solution was concentrated under vacuum, and the residue was purified by prep-HPLC (column: Welch Xtimate C18, 21.2*150 mm, 5 um; mobile phase: Water (0.1% FA)-ACN; gradient: 45%-65%, 13 min; flow rate: 15 mL/min) to give a white solid compound 16 (7.48 mg, 29.81% yield).

MS (ESI): m/z Calcd. for $[M+H^+]$: 491.18, found: 491.37.

$^1$H NMR (400 MHz, DMSO-$d_6$) δ 10.59 (s, 1H), 9.84 (s, 1H), 8.40 (d, J=5.6 Hz, 1H), 8.11 (d, J=2.1 Hz, 1H), 7.59 (dd, J=5.6, 2.2 Hz, 1H), 7.26-7.13 (m, 2H), 5.78 (s, 2H), 4.23 (dd, J=8.1, 5.4 Hz, 1H), 3.95 (t, J=8.1 Hz, 1H), 3.22 (d, J=5.4 Hz, 1H), 2.64-2.54 (m, 1H), 1.52 (s, 3H), 0.69 (d, J=7.5 Hz, 2.2 Hz, 1H), 0.69 (d, J=5.6, 2.2 Hz, 1H) J=7.5 Hz, 3H).

Example 15: Synthesis of 4-((2R,3S,4S,5R)-3-(3,4-difluoro-2-(methoxy-$d_3$)phenyl)-4,5-dimethyl-1-(2,2,2-trifluoroacetyl)-5-(trifluoromethyl)pyrrolidine-2-carboxamido)pyridinamide (17)

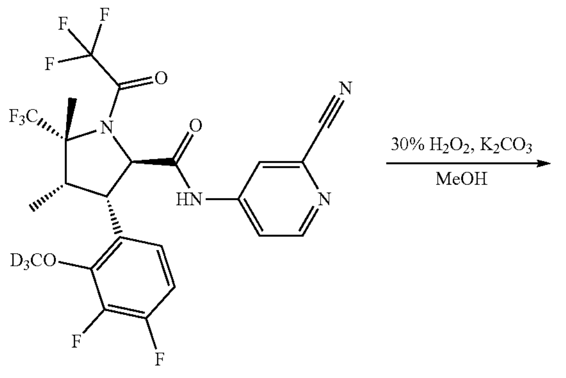

16a

-continued

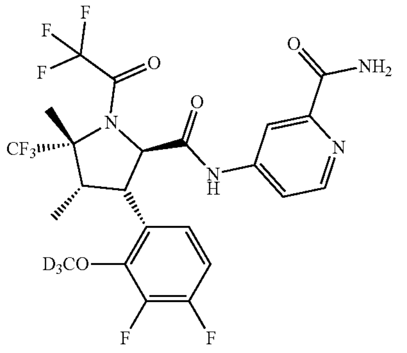

17

Step 1: Compound 16a (50.0 mg, 90.35 μmol, 1.0 eq.) was dissolved in methanol (2 mL), potassium carbonate (37.32 mg, 270 μmol, 3.0 eq.), and 30% hydrogen peroxide solution (290 mg, 2.60 mmol, 28.9 eq.) were added sequentially, and then the mixture was stirred at 25° C. for 16 h. After the raw material was consumed, ice water (5.0 mL) was added to the reaction system, the methanol was spun dry, and the system was extracted with ethyl acetate (15.0 mL*4). Then the organic phases were combined, dried over sodium sulfate, and concentrated under reduced pressure to obtain 45 mg of the crude product, and the residue was purified by prep-HPLC (Column model: Welch Xtimate C18, 21.2*150 mm, 5 um; mobile phase: Water (0.1% FA)-ACN; gradient: 60%-75%, 13 min; flow rate: 15 mL/min) to give a white solid compound 17 (24.76 mg, 47.96% yield).

MS (ESI): m/z Calcd. for $[M+H^+]$: 572.15, found: 572.41.

$^1$H NMR (400 MHz, DMSO-$d_6$) δ 11.11 (s, 1H), 8.51 (d, J=5.5 Hz, 1H), 8.20 (d, J=2.2 Hz, 1H), 8.08 (d, J=2.8 Hz, 1H), 7.73-7.55 (m, 2H), 7.35-7.20 (m, 1H), 7.02 (s, 1H), 5.24 (s, 1H), 4.08 (dd, J=7.9, 2.3 Hz, 1H), 2.82 (t, J=7.6 Hz, 1H), 1.97 (s, 3H), 1.03-0.83 (m, 3H).

Example 16: Synthesis of 2-carbamoyl-4-((2R,3S,4S,5R)-3-(3,4-difluoro-2-(methoxy-$d_3$)phenyl)-4,5-dimethyl-5-(trifluoromethyl)pyrrolidine-2-carboxamido)pyridine 1-oxide (18)

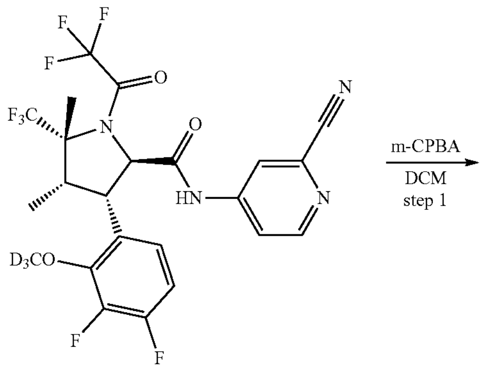

16a

-continued

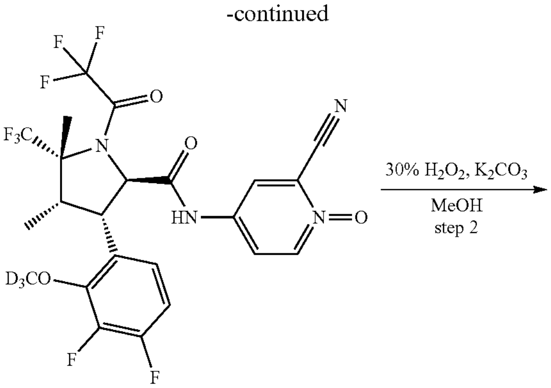

18a

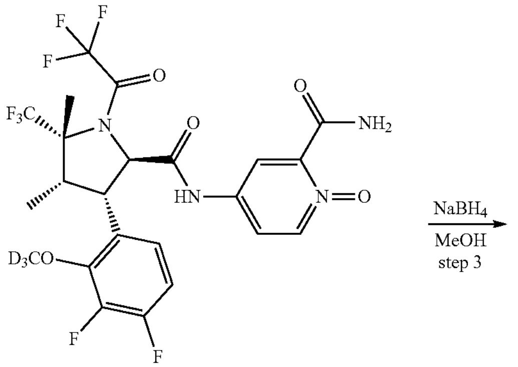

18b

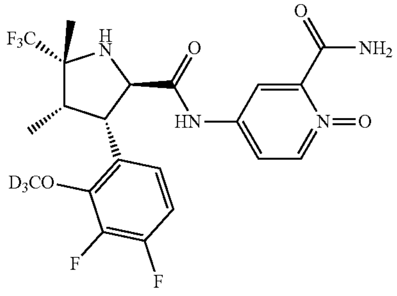

18

Step 1: Compound 16a (200 mg, 361.39 μmol, 1.0 eq.) was dissolved in dichloromethane (4 mL) and m-chloroperoxybenzoic acid (497.01 mg, 2.88 mmol, 8.0 eq.) was added in two batches. The reaction mixture was stirred at 25° C. for 3 days. LC-MS detection showed that the raw material was consumed, then 10.0 mL of water was added to the reaction solution, and the reaction solution was extracted with ethyl acetate (20.0 mL) for three times. The organic phases were combined, washed with saturated saline, dried over anhydrous sodium sulfate, and concentrated under vacuum, and the residue was purified by a normal-phase silica gel column (petroleum ether:ethyl acetate=1:2) to give a yellow solid compound 18a (110.0 mg, 53.5% yield).

MS (ESI): m/z Calcd. for $[M+H^+]$: 470.14, found: 570.0.

Step 2: Compound 18a (45 mg, 79.03 μmol, 1.0 eq.) was dissolved in methanol (2 mL) and potassium carbonate (32.76 mg, 237.00 μmol, 3.0 eq.) and 30% hydrogen peroxide solution (230 μL, 2.28 mmol, 28.9 eq.) were sequentially added in an ice bath and the reaction mixture was stirred at 25° C. for 1 h. The LC-MS detection showed that the raw materials were consumed and 5.0 mL of water was added to the reaction solution, then it was extracted with ethyl acetate (10.0 mL) three times. The organic phases were combined, washed with saturated saline, dried over anhydrous sodium sulfate, and concentrated under vacuum, and the residue was purified by normal-phase silica gel column (petroleum ether:ethyl acetate=1:4) to give a white-like solid compound 18b (35.0 mg, 75.4% yield).

MS (ESI): m/z Calcd. for $[M+H^+]$: 588.15, found: 588.2.

Step 3: Compound 18b (27.00 mg, 45.96 μmol, 1.0 eq.) was dissolved in methanol (1 mL) and sodium borohydride (29.00 mg, 766.59 μmol, 16.7 eq.) was added in three batches. The reaction mixture was stirred at 25° C. for 16 h. The LC-MS detection showed the product was generated, and the reaction solution was concentrated under vacuum, and the residue was purified by prep-HPLC (column model: Welch Xtimate C18, 21.2*150 mm, 5 um; mobile phase: Water (0.1% FA)-ACN; gradient: 45%-60%, 13 (mobile phase: Water (0.1% FA)-ACN; gradient: 45%-60%, 13 min; flow rate: 15 mL/min) to give a white solid compound 18 (2.31 mg, 10.23% yield).

MS (ESI): m/z Calcd. for $[M+H^+]$: 492.17, found: 492.38.

$^1H$ NMR (400 MHz, DMSO-d6) δ 10.90 (s, 1H), 10.64 (d, J=4.6 Hz, 1H), 8.48 (d, J=3.2 Hz, 1H), 8.30 (d, J=7.2 Hz, 1H), 8.23 (d, J=4.7 Hz, 1H), 7.83 (dd, J=7.1, 3.3 Hz, 1H), 7.24-7.10 (m, 2H), 4.23 (dd, J=8.1, 5.1 Hz, 1H), 3.97 (t, 5.1 Hz, 2H), 3.97 (t, 5.1 Hz, 1H) Hz, 1H), 7.24-7.10 (m, 2H), 4.23 (dd, J=8.1, 5.1 Hz, 1H), 3.97 (t, J=8.1 Hz, 1H), 2.59 (q, J=7.6 Hz, 1H), 1.52 (s, 3H), 0.76-0.62 (m, 3H).

Example 17: Synthesis of 4-((2R,3S,4S,5R)-3-(2-(difluoromethoxy)-3,4-difluorophenyl)-4,5-dimethyl-5-(trifluoromethyl)pyrrolidine-2-carboxamido) pyridinamide (19)

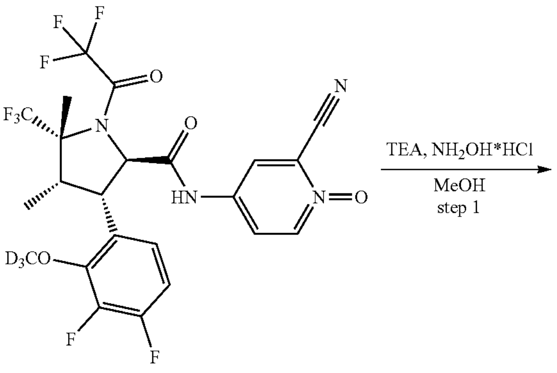

18a

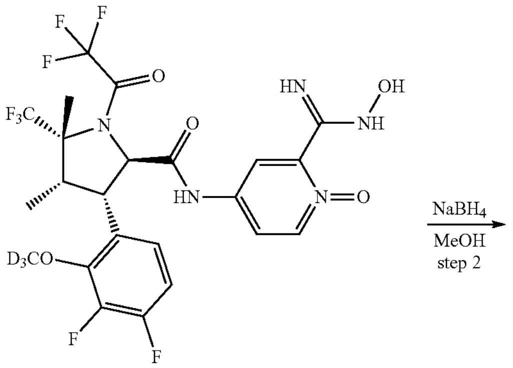

19a

-continued

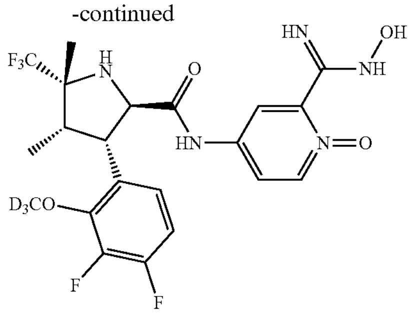

19

Step 1: To a solution of hydroxylamine hydrochloride (76.44 mg, 1.10 mmol, 10.0 eq.), triethylamine (133.57 mg, 1.32 mmol, 12.0 eq.) in methanol (1.0 mL) was added compound 18a (60 mg, 105.37 µmol, 1.0 eq.), the reaction mixture was stirred at 25° C. for 2 h. LCMS detection showed that most of the raw materials were consumed and product was generated, the reaction solution was concentrated under vacuum and the residue was purified by a normal-phase silica gel column (dichloromethane:methanol=20:1) to give a white solid compound 19a (250 mg, crude).

MS (ESI): m/z Calcd. for $[M+H^+]$: 603.16, found: 603.2.

Step 2: Compound 19a (220.00 mg, crude, 1.0 eq.) was dissolved in methanol (5 mL) and sodium borohydride (839.83 mg, 22.20 mmol, 60.0 eq.) was added in eight batches. The reaction mixture was stirred at 25° C. for 16 h. The LC-MS detection showed the product was generated, and the reaction solution was concentrated under vacuum, then 5.0 mL of water was added and the solution was extracted with ethyl acetate (10.0 mL) three times, and the organic phases were combined, washed with saturated saline, dried over anhydrous sodium sulfate, and concentrated under vacuum, and the residue was purified by prep-HPLC (Column model: Welch The residue was purified by prep-HPLC (column model: Welch Xtimate C18, 21.2*150 mm, 5 um; mobile phase: Water (0.1% FA)-ACN; gradient: 40%-65%, 13 min; flow rate: 15 mL/min) to give a white solid compound 19 (12.21 mg, 6.60% yield).

MS (ESI): m/z Calcd. for $[M+H^+]$: 507.19, found: 507.40.

$^1$H NMR (400 MHz, DMSO-$d_6$) δ 10.71 (s, 1H), 10.16 (s, 1H), 8.21-8.07 (m, 2H), 7.63 (dd, J=7.2, 3.2 Hz, 1H), 7.16 (dd, J=9.0, 6.3 Hz, 2H), 6.80 (s, 2H), 4.19 (dd, J=7.9, 5.2 Hz, 1H), 3.95 (t, J=8.1 Hz, 1H), 3.27 (d, J=5.2 Hz, 1H), 2.59 (q, J=7.7 Hz, 1H), 1.51 (s, 3H), 0.79-0.59 (m, 3H).

Test Examples

1. NaV1.8 Blocking Activity of the Compounds to be Tested

The NaV1.8 blocking activity was determined by using a manual patch clamp technique to detect the effect of the subject on the channel currents of stably overexpressed Nav1.8.

1.1 Cell Culture

CHO cell line stably expressing the Nav1.8 sodium channel was used for the experiments, gene information: sodium channel, voltage-gated, type 8, alpha (SCN10A), cDNA strictly similar to GenBank accession number: NM_006514.

Cells were cultured in HAM'S/F-12 medium containing 10% foetal bovine serum and g/mL Blasticidin, 200 g/mL Hygromycin B, and 100 g/mL Zeocin at 37° C., 5% $CO_2$. For expansion or maintenance cultures, cells were treated with 0.25%-Trypsin-EDTA, washed and centrifuged, and then inoculated in 6-cm cell culture dishes with $2.5\times10^5$ cells per cell culture dish (final volume: 5 mL). To maintain the electrophysiological activity of the cells, the cell density did not exceed 80%.

Prior to the patch clamp detection, cells were separated with 0.25%-Trypsin-EDTA and $6.5\times10^3$ cells were spread onto coverslips and incubated (final volume: 500 µL) in 24-well plates for 18 hours, then the test was performed.

1.2 Electrophysiological Recordings

Extracellular Fluid: K-007-1

140 mM NaCl, 3.5 mM KCl, 1 mM $MgCl_{(2)}\cdot6H_2O$, 2 mM $CaCl_{(2)}\cdot2H_2O$, 10 mM D-Glucose, 10 mM HEPES, 1.25 mM $NaH_2PO_4\cdot2H_2O$, and pH was adjusted to 7.4 with NaOH.

Intracellular Fluid: Nav-001-2

50 mM CsCl, 10 mM NaCl, 10 mM HEPES, 60 mM CsF, 20 mM EGTA, and pH was adjusted to 7.2 with CsOH.

Instrument Information is Provided in Table 2 Below:

TABLE 2

Instrument information

| name | vendor | model number |
|---|---|---|
| Patch clamp Amplifier | HEKA (Germany) | EPC10 |
| Data Acquisition Software | HEKA (Germany) | Patchmaster |
| micromanipulator | Sutter Instrument (USA) | MP285 |
| Electrode Drawing Instrument | Sutter Instrument (USA) | P97 |
| Capillary Glass Tubes | Sutter Instrument (USA) | BF150-86-10 |
| microscopy | Olympus (Japan) | IX71 |
| Data analysis software | Wave Metrics (USA) & GraphPad (USA) | IGOR Pro & GraphPad Prism |

Patch Clamp Inspection

Prior to Nav1.8 channel current testing, a blank control solution (DMSO) was diluted into 10 ml of extracellular fluid as the working solution. Positive controls and subjects were first diluted with different doses of DMSO depending on the final concentration before being diluted as working solution using extracellular fluid. 100 nM TTX was added to each working solution to block the TTX-S current. The working solution was sonicated for 20 min before performing the patch clamp test detection.

Patch clamp manipulation: firstly, the capillary glass tube was drawn into a recording electrode using a microelectrode puller, then the electrode filled with intracellular fluid was loaded into the microelectrode holder, and the microelectrode manipulator was maneuvered under an inverted microscope to immerse the electrode into the extracellular fluid and record the electrode resistance (Rpip). The electrode was then slowly contacted to the cell surface and negative pressure suction was given to form a GQ seal. At this time, fast capacitance compensation was performed and negative pressure was continually applied to suction through the cell membrane to form a whole-cell recording pattern. Finally, slow capacitance compensation was performed and experimental parameters such as series resistance (Rs) were recorded. No leakage compensation was given.

Drug administration was initiated when the Nav1.8 current was stabilized for whole-cell recordings, and the next concentration was detected after each drug concentration had acted for approximately 5 min (or until the current was stable). Cell-lined coverslips were placed in the recording bath under an inverted microscope, and the blank control external solution as well as the working solution of the compound to be tested flowed sequentially from low to high concentrations through the recording bath by using gravitational perfusion and thus acted on the cells, and a peristaltic pump was used to exchange fluids during the recording. The current detected by each cell in the compound-free external fluid served as its own control. Each concentration was repeated independently 2-3 times. All electrophysiological experiments were performed at room temperature.

The voltage stimulation scheme for whole-cell patch-clamp recording of Nav1.8 currents was as follows: when a whole-cell seal was formed, the voltage was clamped at −120 mV. The resting state recording of sodium currents was performed by maintaining the voltage for 5 s and then depolarizing it to 0 mV, and then administering a depolarizing pulse (TP1) to 0 mV for 50 ms for detecting the resting state sodium currents. For half-inactivated state recording, the voltage was first stepped at different voltages and maintained for 5 s and then a depolarizing pulse was given to 0 mV to detect the Vhalf. The voltage was then maintained at Vhalf for 5 s, then restored to −120 mV for 20 ms, and then a depolarizing pulse (TP2) was given to 0 mV for 50 ms for detecting the sodium current in the half-inactivated state. Experimental data were acquired by an EPC 10 amplifier (HEKA) and stored in the PatchMaster (HEKA) software.

1.3 Data Analysis

The currents after the action of each drug concentration were first normalized to the blank control currents $$\left(\frac{\text{peak current}-\text{compound}}{\text{peak current}-\text{control}}\right)$$

and then the inhibition corresponding to each drug concentration was calculated $$\left(1-\frac{\text{peak current}-\text{compound}}{\text{peak current}-\text{control}}\right),$$

and the mean, standard deviation (SD) and standard error (SE) for each concentration inhibition were calculated and the data were expressed as mean±SE.

$$Y=\text{Bottom}+(\text{Top}-\text{Bottom})/(1+10\hat{}((\text{Log IC}_{50}-X)*\text{HillSlope}))$$

The above equation was used to calculate the $IC_{50}$ value for each compound and the concentration effect curve was nonlinearly fitted, where $IC_{50}$ was the semi-inhibitory concentration. Calculation of $IC_{50}$ as well as curve fitting was done by using GraphPad Prism software.

The NaV1.8 blocking rates of the compounds of the present invention at concentration of 10 nM are shown in Table 3 below:

TABLE 3

| Compound No. | Blocking rate(%) @10 nM | Blocking rate (%) @3 nM | $IC_{50}$ (nM) |
|---|---|---|---|
| 1 | 97.98% | | 1.297 |
| 2 | 9.30% | | |
| 3 | 84.03% | | |
| 4 | 6.05% | | |
| 5 | 79.03% | 72.73% | |
| 6 | 45.92% | 20.06% | |
| 7 | 91.89% | 67.34% | |
| 8 | 100.00% | 93.13% | |

TABLE 3-continued

| Compound No. | Blocking rate(%) @10 nM | Blocking rate (%) @3 nM | $IC_{50}$ (nM) |
|---|---|---|---|
| 9 | 84.91% | 58.06% | |
| 10 | 99.13% | 95.18% | |
| 11 | 97.84% | 90.26% | 0.7295 |
| 12 | 88.65% | 77.43% | |
| 13 | 92.01% | 75.71% | |
| 14 | 99.51% | 91.40% | |
| 15 | 79.44% | 35.55% | |
| 16 | 25.19% | 6.68% | |
| 17 | 77.24% | 28.89% | |
| 18 | 63.01% | 40.29% | |
| 19 | 55.68% | 26.22% | |

2. Stability of the Compound in Liver Microsomes:

2.1 Preparation of intermediate stock solution for test compounds.

2.1.1. working solution: 5 μL of test or control compound stock solution (10 mM DMSO solution) was diluted with 495 μL of acetonitrile (ACN) to obtain an intermediate stock solution (100 μM, 99% ACN).

2.2 Preparation of NADPH coenzyme working solution.

2.2.1. Material: reduced coenzyme II tetrasodium salt (NADPH-4Na, supplier: BONTAC, Cat. No. BT04);

2.2.2 Preparation procedure: An appropriate amount of NADPH powder was weighed and diluted with 10 mM $MgCl_2$ buffer (working solution concentration: 10 mM; final reaction system concentration: 1 mM).

2.3 Preparation of liver microsomal working solution:

2.3.1 Materials.

TABLE 4

| Liver Microsomal Information | | | |
|---|---|---|---|
| Genus | Product code | Supplier | Abbr |
| Human | Cat No. 452117<br>Lot No. 38298 | Corning | HLM |
| SD rat | Cat No. R1000<br>Lot No. 2110178 | Xenotech | RLM |
| CD-1 mouse | Cat No. 0121E1.01<br>Lot No. 23D035 | IPHASE | MLM |
| Beagle | Cat No. D1000<br>Lot No. 2110225 | Xenotech | DLM |
| Cynomolgus monkey | Cat No. 452413<br>Lot No. 0226001CNC | Corning | CLM |

2.3.2 Preparation procedure: The appropriate concentration of liver microsomal working solution was prepared in 100 mM potassium phosphate buffer;

2.4 Terminating solution.

Acetonitrile (ACN) solution at 4° C. containing 200 ng/mL of Tolbutamide and 200 ng/mL of labetalol as internal standards 2.5. Operation steps:

2.5.1. Preheating empty incubation plates T60 and NCF60 for 10 minutes in advance.

2.5.2. Diluting liver microsomes with 100 mM potassium phosphate buffer to a concentration of 0.56 mg/mL.

2.5.3. Transferring 445 μL of liver microsomal working solution (0.56 mg/mL) to pre-heated incubation plates T60 and NCF60, and then pre-heating the incubation plates T60 and NCF60 for 10 minutes at 37° C. with shaking. Transferring 54 μL of liver microsomes to each well of the blank plate, adding 6 μL of NAPDH coenzyme solution to the blank plate, and finally transferring 180 μL of termination solution to the blank plate.

2.5.4 Adding 5 μL of compound working solution (100 μM) to the incubation plates T60 and NCF60 containing liver microsomes and mixing three times.

2.5.5. Adding 50 μL of buffer to the NCF60 plate and mixing three times, starting the timer and incubating at 37° C. for 60 min with the plate shaking.

2.5.6. Adding 180 μL of quenching solution and 6 μL of NAPDH coenzyme working solution sequentially to quenching plate TO, making sure that the plate was cold to prevent volatilization of the incubation solution.

2.5.7. For plate T60, mixing well three times and immediately transferring 54 μL of mixing solution (0-min time point) to quenching plate TO, then adding 44 μL of NAPDH coenzyme working solution to incubation plate T60. Starting the timer:

TABLE 5

| Final concentrations of components in the reaction solution | |
|---|---|
| Ingredient | Concentration |
| Liver microsomes | 0.5 mg protein/mL |
| Compounds to be tested | 1 μM |
| Control compound | 1 μM |
| Acetonitrile | 0.99% |
| DMSO | 0.01% |

2.5.8. At the 5, 15, 30, 45 and 60 minute time points, adding 180 μL of quenching solution to the quenching plate and transferring 60 μL of reaction solution from the T60 plate to the quenching plate at each time point.

TABLE 6

| Incubation times for reaction solutions | | |
|---|---|---|
| Time point | Starting time | Ending time |
| Blank test | 1:00:00 | 0:00:00 |
| T60 | 1:00:00 | 0:00:00 |
| T45 | 0:45:00 | 0:00:00 |
| T30 | 0:30:00 | 0:00:00 |
| T15 | 0:15:00 | 0:00:00 |
| T5 | 0:05:00 | 0:00:00 |
| T0 | mixing three times and transferring to quenching plate | |

2.5.9. For NCF60 plates, mixing well and transferring 60 μL of reaction solution from the NCF60 incubating solution to a quenching plate containing 180 μL of quenching solution at $60^{th}$ minute.

TABLE 7

| NCF60 incubation | | |
|---|---|---|
| Time point | Starting time | Ending time |
| NCF60 | 1:00:00 | 0:00:00 |

2.5.10. All plates were mixed on a shaker for 10 min and then centrifuged at 4000 rpm at 4° C. for 20 min.

2.5.11. Transferring 80 μL of supernatant to 240 μL of HPLC water and mixing on a shaker for 10 minutes.

2.5.12. Each sample to be analyzed was sealed and mixed on a shaker for 10 minutes before injection into the LC-MS/MS for analysis.

2.6 Data analysis:

2.6.1. Calculating $t_{1/2}$ and Clint(mic) values based on first-order elimination kinetics:

The first-order elimination kinetic equation was:

$$C_t = C_0 \cdot e^{-k_e \cdot t}$$

$$\text{When } C_t = \frac{1}{2} C_0.$$

$$T_{1/2} = \frac{\text{Ln}}{k_e} = \frac{0.693}{k_e}$$

$$CL_{int(mic)} = \frac{0.693}{(\text{in vitro})T_{1/2}} \cdot \frac{1}{\text{mg/mL(the amount of microsomal protein in the reaction system)}}$$

$$CL_{int(liver)} = CL_{int(mic)} \cdot \frac{\text{mg(the mass of liver microsomes)}}{\text{g(the mass of liver)}} \cdot \frac{\text{g(the mass of liver)}}{\text{kg(body weight)}}$$

TABLE 8

Hepatic microsomal stability of some compounds:

| Compound No. | Human liver microsomes T½ (min) | Human liver microsomes Residual (T = 60 min) | Mouse liver microsomes T½ (min) | Mouse liver microsomes Residual (T = 60 min) | Rat liver microsomes T½ (min) | Rat liver microsomes Residual (T = 60 min) |
|---|---|---|---|---|---|---|
| 1 | 80.6 | 58.4% | 41.9 | 37.1% | 18.9 | 11.1% |
| 7 | >145 | 74.8% | >145 | 75.4% | | |
| 8 | >145 | 80.3% | 90.7 | 62.9% | | |
| 11 | 95.4 | 60.1% | 74.2 | 52.9% | | |
| VX-548 | 132.1 | 70.9% | 72.2 | 56.3% | 16.7 | 8.5% |

The structural formula of the control compound VX-548 (synthesized by referring to WO2021113627A1 Example 7) was as follows:

VX-548

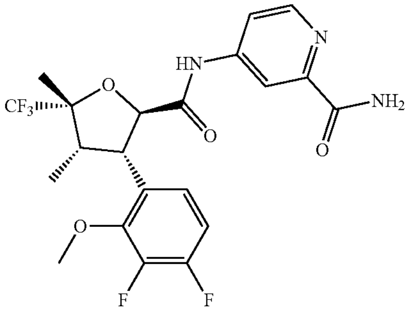

3. Human Liver Microsomal CYP Inhibition Test:

3.1 Buffer solutions: (1) potassium phosphate 100 mM; (2) magnesium chloride, 33 mM;

3.2. compounds:

3.2.1 Substrate reservoirs:

| Substrate | Concentration (mM) | Solvent |
|---|---|---|
| Phenacetin | 20 | MeOH |
| Diclofenac | 10 | MeOH |
| S-mephenytoin | 20 | MeOH |
| Dextromethorphan | 20 | MeOH |
| Midazolam | 10 | MeOH |

3.2.2 Standard inhibitor reservoirs:

| Compound | Concentration (mM) | Solvent |
|---|---|---|
| α-Naphthoflavone | 3 | DMSO |
| Sulfaphenazole | 3 | DMSO |
| (+)-N-3-benzylnirvanol | 1 | DMSO |
| Quinidine | 3 | DMSO |
| Ketoconazole | 3 | DMSO |

3.2.3 Reservoir for compounds to be tested: Dissolving the compounds to be tested in DMSO to form a 10 mM DMSO solution.

3.3 the solution preparation of compound to be tested and positive control compound:

3.3.1. the preparation of working solution of the compound to be tested (100×final concentration);

| Concentration of the compound to be tested | Solution volume (μL) | 1:1 DMSO:MeOH (μL) | Working concen-tration (mM) | Final Concen-tration for test (μM) |
|---|---|---|---|---|
| 10 mM | 30.0 | 30.0 (MeOH) | 5.00 | 50.0 |
| 5.0 mM | 30.0 | 70.0 | 1.50 | 15.0 |
| 1.5 mM | 30.0 | 60.0 | 0.500 | 5.000 |
| 0.5 mM | 30.0 | 70.0 | 0.150 | 1.500 |
| 0.15 mM | 30.0 | 60.0 | 0.0500 | 0.500 |
| 0.05 mM | 30.0 | 70.0 | 0.01500 | 0.1500 |
| 0.015 mM | 30.0 | 60.0 | 0.00500 | 0.0500 |

3.3.2 Preparation of the positive control compound working solution (100×final concentration)

| Compound | Reservoir concen-tration (mM) | Solution Volume (μL) | Methanol volume (μL) | Working concen-tration. (μM) | Final concen-tration for test (μM) |
|---|---|---|---|---|---|
| α-Naphthoflavone | 3 | 10 | 90 | 300 | 3 |
| Sulfaphenazole | 3 | 10 | 90 | 300 | 3 |
| (+)-N-3-benzylnirvanol | 1 | 10 | 90 | 100 | 1 |
| Quinidine | 3 | 10 | 90 | 300 | 3 |
| Ketoconazole | 3 | 10 | 90 | 300 | 3 |

3.3.3 Preparation of substrate solution (10×final concentration)

| CYP | Substrate | Reser-voir concen-tration (mM) | Working concen-tration (μM) | Final concen-tration for test (μM) | Volume (μL) |
|---|---|---|---|---|---|
| 1A2 | Phenacetin | 20 | 100 | 10 | 60 |
| 2C9 | Diclofenac | 10 | 50 | 5 | 60 |
| 2C19 | S-mephenytoin | 20 | 300 | 30 | 180 |
| 2D6 | Dextromethorphan | 20 | 50 | 5 | 30 |
| 3A | Midazolam | 10 | 20 | 2 | 24 |
| | Potassium phosphate buffer | 100 mM | | | 11646 |
| | | | | Total volume. | 12.0 mL |

3.4 Preparation of human liver microsomal mixtures:

3.4.1 Preparation of human liver microsomal working solution (1.27×) (final concentration: 0.2 mg/mL)

| Micro-some | Product Information | Fac-tory | Micro-somal volume (mL) | Buffer volume (mL) | Working concen-tration |
|---|---|---|---|---|---|
| Human liver microsomes | Cat No. 452117 Lot No. 38298 | Corning | 1.012 | 78.988 | 0.253 mg/mL |

3.5 Test Methods:

3.5.1 the working solution preparation of the compound to be tested and the positive control (100×);

3.5.2 Taking the liver microsomes from the −80° C. cryogenic freezer and melting on ice;

3.5.3 Adding 20 μL of substrate solution to the appropriate wells and 20 μL of potassium phosphate buffer to the blank wells;

3.5.4 Adding 2 μL of different concentrations of target compounds (final concentrations from 0.05 μM to 50 μM, 7 concentrations in total) or standard inhibitors to each well, with 2 μL of methanol solution in the non-inhibitor and blank wells;

3.5.5 Adding 1.012 mL of liver microsomes to 78.988 mL of potassium phosphate buffer, then adding 158 μL of liver microsomes solution to all wells; preheating the well plate for 10 minutes in a 37° C. water bath;

3.5.6 Weighing 129.1 mg NADPH (purchased from SyncoZymes Co. Ltd.) and adding to 15.0 mL of 33 Mm $MgCl_2$ solution to give a 10 mM concentration, adding 20 μL to each well;

3.5.7 Mixing and incubating the well plate in a 37° C. water bath for 10 minutes, then adding 400 μL of cold termination solution at the appropriate time point;

3.5.8 Centrifuging the sample at 4000 rpm for 20 minutes to precipitate the protein. Transferring 200 μL of supernatant to 100 μL of HPLC water and shaking for 10 minutes. The samples were analyzed by LC/MS/MS;

3.6 Data analysis:

Percentage inhibition was plotted for blank control and different concentrations of target compounds by using XL fitting or SigmaPlot and the data were analyzed by non-linear regression. $IC_{50}$ values were determined by using either 3-parameter or 4-parameter logistic equations. $IC_{50}$ values were reported as ">50 μM" when the percentage inhibition at the highest concentration (50 μM) was less than 50%;

Equation for four parameters logistic sigmoidal curve:

$$y = \frac{\max}{1 + \left(\frac{x}{IC_{50}}\right)^{-hillslope}}$$

Equations for the 4-parameter logistic S-curve:

$$y = \min + \frac{\max - \min}{1 + \left(\frac{x}{IC_{50}}\right)^{-hillslope}}$$

TABLE 9

Experimental data of CYP inhibition in human liver microsomes for some compounds

| Compound | $IC_{50}$ (μM) | | | | |
|---|---|---|---|---|---|
| No. | CYP1A2 | CYP2C9 | CYP2C19 | CYP2D6 | CYP3A-M |
| 7 | >50 | >50 | 2.13 | >50 | 30.9 |
| 8 | >50 | 22.9 | 29.0 | 41.6 | 26.2 |
| 10 | >50 | >50 | 3.05 | >50 | 39.3 |
| 11 | >50 | 41.4 | 12.5 | >50 | >50 |
| VX-548 | >50 | 17.4 | 3.74 | >50 | >50 |

Conclusion: From the data in Table 9, it can be seen that the compounds of the present invention have weak CYP inhibition, and some exemplary compounds such as Examples 8 and 11 have weaker inhibition on CYP2C19 than VX-548, indicating that these compounds have better drug-drug interaction safety.

4. Pharmacokinetic Experiments:

4.1 Rat test:

4.1.1 Abstract: SD rats were used as test animals, the LC/MS/MS method was applied to determine the drug concentration of the compounds of the Examples in plasma at different points after gavage administration to rats, to study the pharmacokinetic behavior of the compounds of the present invention in rats, and to evaluate their pharmacokinetic characteristics.

4.1.2 Pilot program:

4.1.2.1 Test drug: compound 11 and control VX-548

4.1.2.2 Test animals: 6 male SD rats and 6 female rats, all provided by Shanghai Jihui Laboratory Animal Breeding Co. The animals were fasted for at least 12 hours before administration and food supply was resumed 4 hours after administration.

4.1.2.3 Drug Preparation: Weighed an amount of the test compound separately and prepared a completely clear solution with a final concentration of 1 mg/mL using a mixed solvent of DMSO:Solutol:Saline (5%:5%:90%).

4.1.2.4 Administration: a dose of 10 mg/kg, a volume of 10 mL/kg.

4.1.3 Test operation: 0.1 mL blood samples were collected from the orbit before and 15 min, 30 min, 1 h, 2 h, 4 h, 6 h, 8 h, 10 h, 24 h after the administration of the drug to male rats and placed in EDTA-K2 anticoagulant tubes. 0.03 mL blood samples were collected from the orbit before and 0.5 h, 1 h, 2 h, 3 h, 6 h, 10 h and 24 h after administration to female rats. After blood samples were collected, they were placed in labelled centrifuge tubes in ice-water bath and rapidly centrifuged to separate the plasma at 4000 rpm for 10 min at 4° C. The plasma was stored at −70° C. or below for measurement.

The plasma samples were thawed at room temperature and 50 μL was added to 400 μL of acetonitrile containing the internal standard (40 ng/mL, terfenadine), vortexed for 1 min and centrifuged for 10 min at 4° C. and 15,400 g. 1 μL of the supernatant was injected for analysis.

4.1.4 Pharmacokinetic results:

TABLE 10

Pharmacokinetic parameters of compounds in SD rats:

| Compound No. | Sex of rats | Administering dose (mg/kg) | blood concentration Cmax (ng/mL) | Area under the curve AUC0-t (ng*h/mL) |
|---|---|---|---|---|
| 11 | male | 10 | 1006 | 4656 |
| VX-548 | male | 10 | 385 | 1211 |
| 11 | female | 10 | 1850 | 23809 |
| VX-548 | female | 10 | 719 | 10876 |

4.2 Dog test:

4.2.1 Abstract: Beagle was used as the test animal, the LC/MS/MS method was applied to determine the drug concentration in the plasma of Beagle at different points after intravenous injection of the compounds of the examples, to study the pharmacokinetic behavior of the compounds of the present invention in the Beagle, and to evaluate their pharmacokinetic characteristics.

4.2.2 Pilot program:

4.2.2.1 Test drug: compound 11 and control VX-548

4.2.2.2 Test animals: 4 male Beagles, provided by Jiangsu LingfuZhaoshengyuan Biotechnology Co. Fasting started at 5 p.m. on the day before drug administration, and the duration of fasting was no less than 12 hours, and food was resumed 4 hours after drug administration.

4.2.2.3 Drug Preparation: Weighed an amount of the test compound and prepared a completely clear solution with a final concentration of 1 mg/mL using a mixed solvent of DMSO: Solutol: Saline (5%: 5%: 90%).

4.2.2.4 Administration: a dose of 0.5 mg/kg, a volume of 0.5 mL/kg.

4.2.3 Test operation: 0.4 mL of blood samples were collected from the forelimb vein of male Beagles before and 5 min, 15 min, 30 min, 1 h, 2 h, 4 h, 6 h, 8 h, 10 h and 24 h after intravenous administration and placed in EDTA-K2 anticoagulant tubes. After blood samples were collected, they were placed in labelled centrifuge tubes in ice water bath and rapidly centrifuged to separate the plasma. Centrifugation conditions: 4000 rpm, 10 min, 4° C., and the plasma was placed at −70° C. or below for measurement.

Plasma samples were thawed at room temperature and 50 μL was added to 400 μL of acetonitrile containing the internal standard (40 ng/mL, terfenadine), vortexed for 1 min and then centrifuged at 15400 g for 10 min at 4° C. The supernatant was diluted 10-fold with 80% acetonitrile in water and 1 μL sample was injected for analysis.

4.1.4 Pharmacokinetic results:

TABLE 11

| Pharmacokinetic parameters of compound in Beagle: | | | | | |
|---|---|---|---|---|---|
| Compound No. | Mode of adminis-tration | Adminis-tering dose (mg/kg) | Area under the curve AUC0-t (ng*h/mL) | half-life t½ (h) | Clearance CL mL/h/kg |
| 11 | iv | 0.5 | 15644 | 57.4 | 8.05 |
| VX-548 | iv | 0.5 | 11106 | 19.7 | 26.3 |

5. Testing of the Proportion of Free Drug in Human Plasma:

On the day of the experiment, human plasma samples (purchased from Biomex) were thawed under running tap water and centrifuged at 3220 g for 5 min to remove blood clots. The pH of the resulting plasma was measured and adjusted to pH 7.4±0.1 by using 1% phosphoric acid or 1 N sodium hydroxide as required.

Pretreating the dialysis membranes according to the manufacturer's instructions: The dialysis membrane strips were soaked in ultrapure water at room temperature for approximately 1 hour. Afterwards, each membrane strip containing 2 layers of membrane was separated and soaked in ethanol:water (20:80 v:v) for approximately 20 minutes, then it was ready for use or stored at 2-8° C. (stored for up to 1 month). The membranes were rinsed and soaked in ultrapure water for 20 min before experiments.

A 10 mM DMSO solution of test compound or control warfarin was taken and diluted to 400 μM with DMSO, then 3 μl was taken and added to 597 μl of blank plasma matrix solution to obtain 2 μM of compound solution respectively. 50 μl of test compound solution or control solution was transferred to a sample collection plate with 3 replicate wells per sample. 50 μl of blank PBS buffer solution was added to each well, followed by adding 500 μl of termination solution (acetonitrile containing 250 nmol/L of mephentermine, 250 nmol/L of labetalol). 100 μl of each well was transferred to the donor end of the dialyser's dialysis wells and 100 μl of dialysate was added to the receiver end. The well plates were then shaken at approximately 100 rpm for 4 h in a humidified incubator at 37±1° C., 5% CO2. After the dialysis, 50 μL of sample was each taken from the buffer side and the plasma matrix side of the dialysis device and put into a new 96-well sample collection plate. An equal volume of the opposite blank matrix (buffer or plasma matrix) was added to each sample so that the volume ratio of plasma matrix to dialysis buffer in each well was 1:1 (v:v), resulting in a final volume of 100 μL. All the samples were subjected to protein precipitation and then used for LC-MS/MS analysis.

Unbonded %, bonded % and recovered % were calculated using the following formulae.

$$\text{Unbonded }\% = 100\times F/T$$

$$\text{Bonded }\% = 100 - \text{unbonded }\%$$

-continued $$\text{Recovery }\% = 100\times(F+T)/T0$$

F=peak area ratio of test compound to internal reference compound on the buffer side after 4 h of incubation T=peak area ratio of test compound to internal reference compound on the plasma matrix side after 4 h of incubation T0=peak area ratio of test compound to internal reference compound at zero point

TABLE 12

| free drug proportions of compound 11 and VX-548 in human plasma: | |
|---|---|
| Compound No. | free drug proportion of in human plasma |
| 11 | 1.6% |
| VX-548 | 1.0% |

EMBODIMENTS

Embodiment 1. A compound represented by formula (I), or a stereoisomer, tautomer, deutero-derivative, or pharmaceutically acceptable salt thereof:

formula (I)

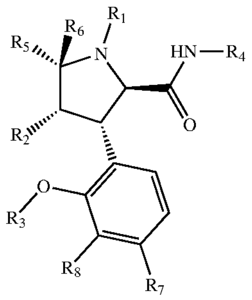

wherein $R_1$ is selected from the group consisting of hydrogen atom, $C_{1-15}$ alkyl, $C_{1-15}$ alkoxy, $C_{1-15}$ alkyl carbonyl, $C_{3-15}$ cycloalkyl, and four- to eight-membered heterocyclyl containing 1 to 3 heteroatoms selected from N, O and S, wherein the $C_{1-15}$ alkyl, $C_{1-15}$ alkoxy, $C_{1-15}$ alkylcarbonyl, $C_{3-15}$ cycloalkyl, four- to eight-membered heterocyclyl containing 1 to 3 heteroatoms selected from N, O and S may be substituted with one or more $R_a$ substituents, the $R_a$ is selected from the group consisting of hydrogen atom, $C_{1-6}$ alkyl, $C_{1-6}$ alkoxy, $C_{3-6}$ cycloalkyl, halogen atom, amino, hydroxyl, and amide;

$R_2$ is selected from the group consisting of hydrogen atom, $C_{1-8}$ alkyl, $C_{1-8}$ alkoxy, deutero-$C_{1-8}$ alkyl, halo-$C_{1-8}$ alkyl, halo-$C_{1-8}$ alkoxy, and $C_{3-6}$ cycloalkyl;

$R_3$ is selected from the group consisting of hydrogen atom, $C_{1-8}$ alkyl, deutero-$C_{1-8}$ alkyl, halo-$C_{1-8}$ alkyl, $C_{3-6}$ cycloalkyl, and three- to eight-membered heterocyclyl containing 1 to 3 heteroatoms selected from N, O and S;

$R_4$ is selected from the group consisting of $C_{6-14}$ aryl, five- to eight-membered heteroaryl containing 1 to 3 heteroatoms selected from N, O and S, and five- to eight-membered heteroaryl oxide containing 1 to 3 heteroatoms selected from N, O and S, wherein the $C_{6-14}$ aryl, five- to eight-membered heteroaryl containing 1 to 3 heteroatoms selected from N, O and S may be substituted with one or more $R_b$ substituents, wherein the $R_b$ is selected from the group consisting of hydrogen atom, $C_{1-6}$ alkyl, $C_{3-6}$ cycloalkyl, halogen atom, nitro, amino, hydroxyl, carbonyl, cyano, formamido, oxyl, sulfonamide, aza-hydroxyformamidinyl, aza-hydroxyamidino, $C_{1-6}$ alkyl substituted by 1 to 3 halogen atoms, $C_{3-6}$ cycloalkyl substituted by 1 to 3 halogen atoms, $C_1$. 6 alkyl substituted by 1 to 3 hydroxyl, $C_{3-6}$ cycloalkyl substituted by 1 to 3 hydroxyl, and four- to six-membered heterocyclyl containing 1 to 3 heteroatoms selected from N, O and S and unsubstituted or substituted by 1 to 3 $C_{1-6}$ alkyl;

$R_5$ is selected from the group consisting of $C_{1-6}$ alkyl, halo-$C_{1-6}$ alkyl, and $C_{3-6}$ cycloalkyl;

$R_6$ is selected from the group consisting of hydrogen atom, $C_{1-6}$ alkyl, halo-$C_{1-6}$ alkyl, and $C_{3-6}$ cycloalkyl;

$R_7$ is selected from the group consisting of hydrogen atom, $C_{1-6}$ alkyl, halo-$C_{1-6}$ alkyl, $C_{1-6}$ alkoxy, halo-$C_{1-6}$ alkoxy, $C_{3-6}$ cycloalkyl, halogen atom, cyano, and amide;

$R_8$ is selected from the group consisting of hydrogen atom, $C_{1-6}$ alkyl, halo-$C_{1-6}$ alkyl, halogen atom, and cyano.

Embodiment 2. A compound represented by formula (I), or a stereoisomer, tautomer, deutero-derivative, or pharmaceutically acceptable salt thereof according to Embodiment 1, wherein, preferably, $R_1$ is selected from the group consisting of hydrogen atom, $C_{1-6}$ alkyl, $C_{1-6}$ alkoxy, $C_{1-6}$ alkylcarbonyl, $C_{3-8}$ cycloalkyl, and four- to six-membered heterocyclyl containing 1 to 3 heteroatoms selected from N, O, and S, wherein the $C_{1-6}$ alkyl, $C_{1-6}$ alkoxy, $C_{1-6}$ alkylcarbonyl, $C_{3-8}$ cycloalkyl, four- to six-membered heterocyclyl containing 1 to 3 heteroatoms selected from N, O and S may be substituted with 1 to 3 $R_a$ substituents, the $R_a$ is selected from the group consisting of hydrogen atom, $C_{1-4}$ alkyl, $C_{1-4}$ alkoxy, $C_{3-6}$ cycloalkyl, halogen atom, amino, hydroxyl, and amide;

preferably, $R_i$ is selected from the group consisting of hydrogen atom, $C_{1-4}$ alkyl, $C_{1-4}$ alkoxy, $C_{1-4}$ alkylcarbonyl, $C_{3-6}$ cycloalkyl, and four- to six-membered heterocyclyl containing 1 or 2 heteroatoms selected from N, O and S, wherein the $C_{1-4}$ alkyl, $C_{1-4}$ alkoxy, $C_{1-4}$ alkylcarbonyl, $C_{3-6}$ cycloalkyl, four- to six-membered heterocyclyl containing 1 or 2 heteroatoms selected from N, O and S may be substituted with 1 to 3 $R_a$ substituents, the $R_a$ is selected from the group consisting of hydrogen atom, $C_{1-4}$ alkyl, $C_{1-4}$ alkoxy, $C_{3-6}$ cycloalkyl, halogen atom, amino, hydroxyl, and amide;

preferably, $R_1$ is selected from the group consisting of hydrogen atom, methyl, trifluoroacetyl, ethyl, n-propyl, isopropyl, n-butyl, sec-butyl, tert-butyl, cyclopropyl, cyclobutyl, cyclopentyl, and cyclohexyl, wherein the above substituents may be substituted with 1 or 2 $R_a$ substituents, the $R_a$ is selected from the group consisting of hydrogen atom, methyl, ethyl, propyl, isopropyl, n-butyl, sec-butyl, tert-butyl, methoxy, ethoxy, propoxy, isopropoxy, n-butoxy, sec-butoxy, tert-butoxy, cyclopropyl, cyclobutyl, cyclopentyl, cyclohexyl, fluorine atom, chlorine atom, bromine atom, amino, hydroxy, and amide;

preferably, $R_1$ is selected from the group consisting of hydrogen atom, methyl, trifluoroacetyl, ethyl, n-propyl, isopropyl, n-butyl, and cyclopropyl, wherein the above substituents may be substituted with 1 or 2 $R_a$ substituents, the $R_a$ is selected from the group consisting of hydrogen atom, methyl, methoxy, fluorine atom, chlorine atom, bromine atom, amino, hydroxy, cyano, and amide;

preferably, $R_2$ is selected from the group consisting of hydrogen atom, $C_{1-6}$ alkyl, $C_{1-6}$ alkoxy, deutero-$C_{1-6}$ alkyl, halo-$C_{1-6}$ alkyl, halo-$C_{1-6}$ alkoxy, and $C_{3-6}$ cycloalkyl;

preferably, $R_2$ is selected from the group consisting of hydrogen atom, $C_{1-4}$ alkyl, $C_{1-4}$ alkoxy, deutero-$C_{1-4}$ alkyl, halo-$C_{1-4}$ alkyl, halo-$C_{1-4}$ alkoxy, and $C_{3-6}$ cycloalkyl;

preferably, $R_2$ is selected from the group consisting of hydrogen atom, methyl, ethyl, n-propyl, isopropyl, n-butyl, sec-butyl, tert-butyl, methoxy, ethoxy, n-propoxy, isopropoxy, n-butoxy, sec-butoxy, tert-butoxy, deuteromethyl, mono-fluoromethyl, difluoromethyl, trifluoromethyl, mono-fluoroethyl, difluoroethyl, trifluoroethyl, tetrafluoroethyl, pentafluoroethyl, difluoropropyl, trifluoropropyl, tetrafluoropropyl, pentafluoropropyl, hexafluoropropyl, perfluoropropyl, cyclopropyl, cyclobutyl, cyclopentyl, and cyclohexyl;

preferably, $R_3$ is selected from the group consisting of hydrogen atom, $C_{1-6}$ alkyl, deutero-$C_{1-6}$ alkyl, halo-$C_{1-6}$ alkyl, $C_{3-6}$ cycloalkyl, and three- to six-membered heterocyclyl group containing 1 to 3 heteroatoms selected from N, O and S;

preferably, $R_3$ is selected from the group consisting of hydrogen atom, $C_{1-4}$ alkyl, deutero-$C_{1-4}$ alkyl, halo-$C_{1-4}$ alkyl, $C_{3-6}$ cycloalkyl, and three- to six-membered heterocyclyl containing 1 or 2 heteroatoms selected from N and O;

preferably, $R_3$ is selected from the group consisting of hydrogen atom, methyl, ethyl, n-propyl, isopropyl, n-butyl, sec-butyl, tert-butyl, deuteromethyl, monofluoromethyl, difluoromethyl, trifluoromethyl, monofluoroethyl, difluoroethyl, trifluoroethyl, tetrafluoroethyl, pentafluoroethyl, difluoropropyl, trifluoropropyl, tetrafluoropropyl, pentafluoropropyl, hexafluoropropyl, perfluoropropyl, cyclopropyl, cyclobutyl, cyclopentyl, and cyclohexyl;

preferably, $R_4$ is selected from the group consisting of $C_{6-10}$ aryl, five- to six-membered heteroaryl containing 1 to 3 heteroatoms selected from N and 0, and five- to six-membered heteroaryl oxide containing 1 to 3 heteroatoms selected from N, O and S, wherein the $C_{6-10}$ aryl, five- to six-membered heteroaryl containing 1 to 3 heteroatoms selected from N and 0, five- to six-membered heteroaryl oxide containing 1 to 3 heteroatoms selected from N, O and S may be substituted with one or more $R_b$ substituents, wherein the $R_b$ is selected from the group consisting of hydrogen atom, $C_{1-4}$ alkyl, $C_{3-6}$ cycloalkyl, halogen atom, nitro, amino, hydroxy, carbonyl, cyano, formamido, oxyl, sulfonamido, aza-hydroxyformamidino, aza-hydroxyamidinyl, $C_{1-4}$ alkyl substituted by 1 to 3 halogen atoms, $C_{3-6}$ cycloalkyl substituted by 1 to 3 halogen atoms, $C_{1-4}$ alkyl substituted by 1 to 2 hydroxyl, $C_{3-6}$ cycloalkyl substituted by 1 to 2 hydroxyl, and four- to six-membered heterocyclyl containing 1 or 2 heteroatoms selected from N or O and unsubstituted or substituted by 1 to 3 $C_{1-4}$ alkyls;

preferably, $R_4$ is selected from the group consisting of phenyl, naphthyl, anthracenyl, furanyl, thienyl, pyrrolyl, pyrazolyl, oxazolyl, isoxazolyl, isothiazolyl, imidazolyl, thiazolyl, pyridinyl, pyridazinyl, pyrimidinyl, pyrazinyl, indolyl, quinolinyl, isoquinolinyl, pyridinyl oxide, imidazolyl oxide, pyrrolyl oxide, pyrazolyl oxide, oxazolyl oxide, isoxazolyl oxide, isothiazolyl oxide, thiazolyl oxide, pyridazinyl oxide, pyrimidinyl oxide, pyrazinyl oxide, indolyl oxide, quinolinyl oxide, and isoquinolinyl oxide, wherein the above substituents may be substituted by one or more $R_b$ substituents, wherein the $R_b$ is selected from the group consisting of hydrogen atom, $C_{1-4}$ alkyl, $C_{3-6}$ cycloalkyl, halogen atom, amino, carbonyl, hydroxyl, cyano, formamido, oxyl, sulfonamido, aza-hydroxyformamidinyl, aza-hydroxyamidinyl, $C_{1-4}$ alkyl substituted with 1 to 3 halogen atoms, $C_{3-6}$ cycloalkyl substituted with 1 to 3 halogen atoms, $C_{1-4}$ alkyl substituted with 1 to 3 hydroxyl, $C_{3-6}$ cycloalkyl substituted with 1 to 3 hydroxyl, and four- to six-membered heterocyclyl containing 1 to 3 heteroatoms selected from N, O, and S and unsubstituted or substituted with 1 to 3 $C_{1-4}$ alkyl;

preferably, $R_5$ is selected from the group consisting of $C_{1-4}$ alkyl, halo-$C_{1-4}$ alkyl, and $C_{3-6}$ cycloalkyl;

preferably, $R_5$ is selected from the group consisting of methyl, ethyl, n-propyl, isopropyl, n-butyl, sec-butyl, tert-butyl, cyclopropyl, cyclobutyl, cyclopentyl, cyclohexyl, monofluoromethyl, difluoromethyl, trifluoromethyl, monofluoroethyl, difluoroethyl, trifluoroethyl, tetrafluoroethyl, pentafluoroethyl, difluoropropyl, trifluoropropyl, tetrafluoropropyl, pentafluoropropyl, hexafluoropropyl, and perfluoropropyl;

preferably, $R_5$ is selected from the group consisting of methyl, ethyl, n-propyl, isopropyl, n-butyl, sec-butyl, tert-butyl, and trifluoromethyl;

preferably, $R_6$ is selected from the group consisting of $C_{1-4}$ alkyl, halo-$C_{1-4}$ alkyl, and $C_{3-6}$ cycloalkyl;

preferably, $R_6$ is selected from the group consisting of methyl, ethyl, n-propyl, isopropyl, n-butyl, sec-butyl, tert-butyl, cyclopropyl, cyclobutyl, cyclopentyl, cyclohexyl, monofluoromethyl, difluoromethyl, trifluoromethyl, monofluoroethyl, difluoroethyl, trifluoroethyl, tetrafluoroethyl, pentafluoroethyl, difluoropropyl, trifluoropropyl, tetrafluoropropyl, pentafluoropropyl, hexafluoropropyl, and perfluoropropyl;

preferably, $R_6$ is selected from the group consisting of hydrogen atom, methyl, ethyl, n-propyl, and isopropyl;

preferably, $R_7$ is selected from the group consisting of $C_{1-4}$ alkyl, halo-$C_{1-4}$ alkyl, $C_{1-4}$ alkoxy, halo-$C_{1-4}$ alkoxy, $C_{3-6}$ cycloalkyl, halogen atom, cyano, and amido;

preferably, $R_7$ is selected from the group consisting of halogen atom, methyl, ethyl, n-propyl, isopropyl, n-butyl, sec-butyl, tert-butyl, methoxy, ethoxy, n-propoxy, isopropoxy, n-butoxy, sec-butoxy, tert-butoxy, cyclopropyl, cyclobutyl, cyclopentyl, cyclohexyl, monofluoromethyl, difluoromethyl, trifluoromethyl, monofluoroethyl, difluoroethyl, trifluoroethyl, tetrafluoroethyl, pentafluoroethyl, monofluoromethoxy, difluoromethoxy, trifluoromethoxy, monofluoroethoxy, difluoroethoxy, trifluoroethoxy, tetrafluoroethoxy, and pentafluoroethoxy;

preferably, $R_7$ is selected from the group consisting of hydrogen atom, methyl, isopropyl, cyclopropyl, cyclobutyl, fluorine atom, chlorine atom, bromine atom, methoxy, and trifluoromethoxy;

preferably, $R_8$ is selected from the group consisting of hydrogen atom, $C_{1-4}$ alkyl, halo-$C_{1-4}$ alkyl, halogen atom, and cyano;

preferably, $R_8$ is selected from the group consisting of hydrogen atom, halogen atom, methyl, ethyl, n-propyl, isopropyl, n-butyl, sec-butyl, tert-butyl, monofluoromethyl, difluoromethyl, trifluoromethyl, monofluoroethyl, difluoroethyl, trifluoroethyl, tetrafluoroethyl, and pentafluoroethyl;

preferably, $R_8$ is selected from the group consisting of hydrogen atom, fluorine atom, chlorine atom, bromine atom, and methyl.

Embodiment 3. A compound represented by formula (I), or a stereoisomer, tautomer, deutero-derivative, or pharmaceutically acceptable salt thereof according to Embodiment 1, wherein the formula (I) is represented by the following formula (II):

Formula (II)

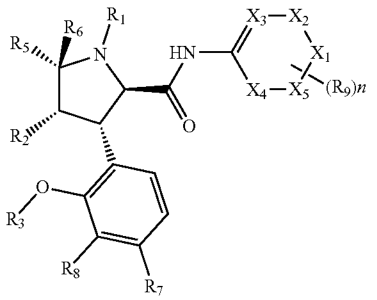

wherein the definitions of $R_1$ to $R_8$ are as same as those in any one of claim 1 or 2 respectively;

$X_1$ to $X_5$ are each independently CH, O or N or $N^+$—$O^-$, provided that at most three of $X_1$ to $X_5$ are N and the rest are C;

$R_9$ is selected from the group consisting of hydrogen atom, halogen atom, amino, hydroxyl, carbonyl, cyano, amido, oxo, sulfonamido, aza-hydroxyformamidine, aza-hydroxyamidinium, $C_{1-6}$ alkyl, $C_{3-8}$ cycloalkyl, $C_{6-14}$ aryl, four- to six-membered heterocyclyl containing 1 to 3 heteroatoms selected from N, O, and S, and five- to six-membered heteroaryl containing 1 to 3 heteroatoms selected from N, O and S, wherein the $C_{1-6}$ alkyl, $C_{3-8}$ cycloalkyl, $C_{6-14}$ aryl, four- to six-membered heterocyclyl containing 1 to 3 heteroatoms selected from N, O and S, and five- to six-membered heteroaryl containing 1 to 3 heteroatoms selected from N, O and S may be substituted with 1 to 3 $R_c$ substituents, wherein $R_c$ is selected from the group consisting of hydrogen atom, $C_{1-4}$ alkyl, $C_{3-6}$ cycloalkyl, halogen atom, nitro, amino, hydroxy, cyano, and formamido;

n is an integer selected from 0, 1, 2, 3 or 4;

preferably, $X_3$ and $X_4$ are CH or N;

preferably, $X_1$, $X_2$ or $X_5$ is each independently selected from CH or N or $N^+$—$O^-$;

preferably, $R_9$ is selected from the group consisting of hydrogen atom, halogen atom, amino, hydroxyl, carbonyl, cyano, formamido, oxyl, sulfonamido, aza-hydroxyformamidine, aza-hydroxyamidinium, $C_{1-6}$ alkyl, $C_{3-8}$ cycloalkyl, $C_{6-14}$ aryl, four- to six-membered heterocyclyl containing 1 to 3 heteroatoms selected from N, O, and S, and five- to six-membered heteroaryl containing 1 to 3 heteroatoms selected from N, O, and S atoms, wherein the $C_{1-6}$ alkyl, $C_{3-8}$ cycloalkyl, $C_{6-14}$ aryl, four- to six-membered heterocyclyl containing 1 to 3 heteroatoms selected from N, O and S, and five- to six-membered heteroaryl containing 1 to 3 heteroatoms selected from N, O and S may be substituted with 1 to 3 $R_c$ substituents, wherein $R_c$ is selected from hydrogen atom, $C_{1-4}$ alkyl, $C_{3-6}$ cycloalkyl, halogen atom, amino, hydroxy, cyano, and amido;

preferably, $R_9$ is selected from the group consisting of hydrogen atom, halogen atom, amino, hydroxyl, carbonyl, cyano, formamido, oxyl, sulfonamido, aza-hydroxyformamidinyl, aza-hydroxyformamidinyl, $C_{1-4}$ alkyl, $C_{3-6}$ cycloalkyl, $C_{6-10}$ aryl, four- to six-membered heterocyclyl containing 1 to 3 heteroatoms selected from N, O, and S, and five- to six-membered heteroaryl containing 1 to 3 heteroatoms selected from N, O and S atoms, wherein the $C_{1-4}$ alkyl, $C_{3-6}$ cycloalkyl, $C_{6-10}$ aryl, four- to six-membered heterocyclyl containing 1 to 3 heteroatoms selected from N, O and S, and five- to six-membered heteroaryl containing 1 to 3 heteroatoms selected from N, O and S may be substituted with 1 to 3 $R_c$ substituents, wherein the $R_c$ is selected from the group consisting of hydrogen atom, $C_{1-3}$ alkyl, $C_{3-6}$ cycloalkyl, halogen atom, amino, hydroxy, cyano, and amido;

preferably, $R_9$ is selected from the group consisting of hydrogen atom, halogen atom, amino, hydroxyl, carbonyl, cyano, formamido, oxyl, sulfonamido, aza-hydroxyformamidinyl, aza-hydroxyformamidinyl, $C_{1-4}$ alkyl, $C_{3-6}$ cycloalkyl, $C_{6-10}$ aryl, four- to six-membered heterocyclyl containing 1 or 2 heteroatoms selected from N and O, five- to six-membered heteroaryl containing 1 or 2 heteroatoms selected from N, O and S, wherein $C_{1-4}$ alkyl, $C_{3-6}$ cycloalkyl, $C_{6-10}$ aryl, four- to six-membered heterocyclyl containing 1 or 2 heteroatoms selected from N and O, and five- to six-membered heteroaryl containing 1 or 2 heteroatoms selected from N and O may be substituted with 1 to 3 $R_c$ substituents, wherein $R_c$ is selected from the group consisting of hydrogen atom, $C_{1-3}$ alkyl, $C_{3-6}$ cycloalkyl, halogen atom, amino, hydroxy, cyano, and formamido;

preferably, $R_9$ is selected from the group consisting of hydrogen atom, halogen atom, amino, hydroxyl, carbonyl, cyano, formamido, oxyl, sulfonamido, aza-hydroxyformamidinyl, aza-hydroxyformamidinyl, methyl, ethyl, n-propyl, isopropyl, n-butyl, sec-butyl, tert-butyl, cyclopropyl, cyclobutyl, cyclopentyl, cyclohexyl, phenyl,

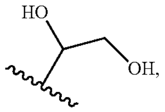
,
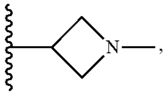
,
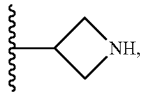
,
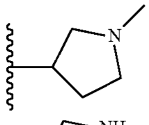
,
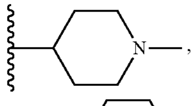
,
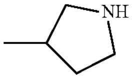
, and
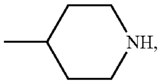
, wherein the above substituents may be substituted with 1 or 2 $R_c$ substituents, $R_c$ is selected from the group consisting of hydrogen atom, methyl, ethyl, propyl, isopropyl, cyclopropyl, cyclobutyl, cyclopentyl, cyclohexyl, fluorine atom, chlorine atom, bromine atom, amino, hydroxyl, cyano, and formamido;

preferably, n is an integer selected from 0, 1 or 2;

preferably, n is an integer selected from 0 or 1.

Embodiment 4. A compound represented by formula (I), or a stereoisomer, tautomer, deutero-derivative, or pharmaceutically acceptable salt thereof according to Embodiment 1, wherein the formula (I) is represented by the following formula (III):

Formula (III)

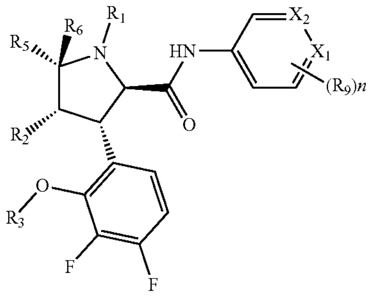

wherein the definitions of $R_1$, $R_2$, $R_3$, $R_5$, $R_6$ are as same as those in Embodiment 1 or Embodiment 2 respectively;

the definitions of $R_9$, $X_1$, $X_2$ are as same as those in Embodiment 3 respectively.

Embodiment 5. A compound represented by formula (I), or a stereoisomer, tautomer, deutero-derivative, or pharmaceutically acceptable salt thereof according to Embodiment 1, wherein the formula (I) is represented by the following formula (IVa), formula (IVb), formula (IVc) or formula (IVd):

Formula (IVa)

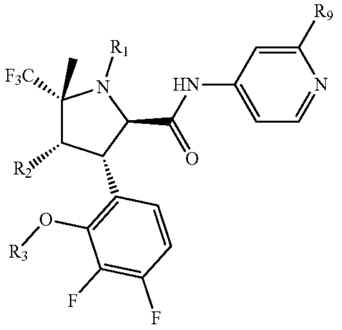

Formula (IVb)

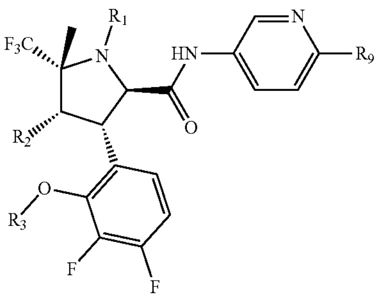

-continued

Formula (IVc)

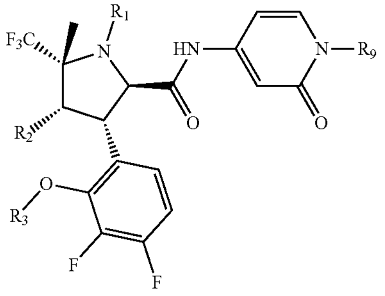

Formula (IVd)

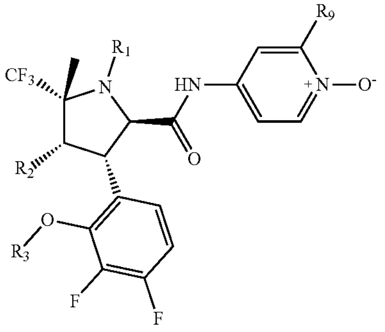

wherein the definitions of $R_1$, $R_2$, and $R_3$ are as same as those in Embodiment 1 or Embodiment 2 respectively; and the definition of $R_5$ is as same as that in Embodiment 3.

Embodiment 6. A compound represented by formula (I), or a stereoisomer, tautomer, deutero-derivative, or pharmaceutically acceptable salt thereof according to Embodiment 1, wherein it is selected from the following compounds:

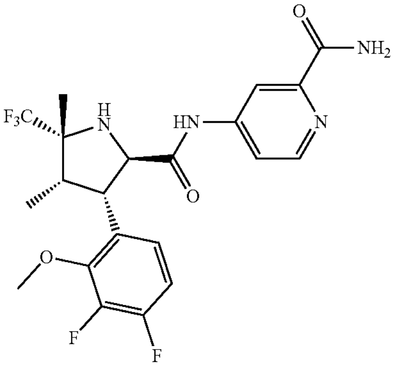

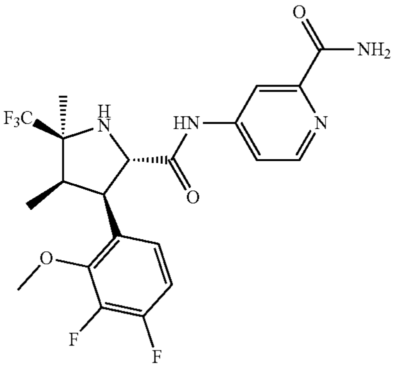

-continued

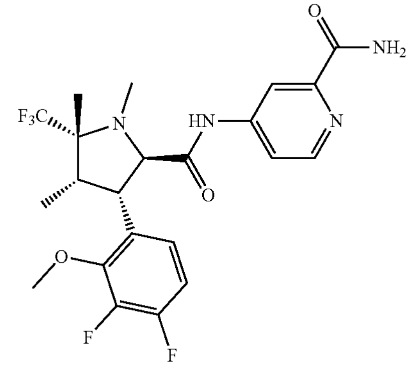

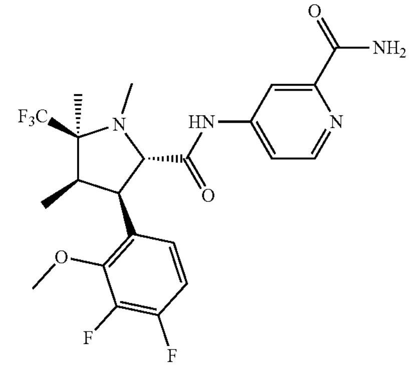

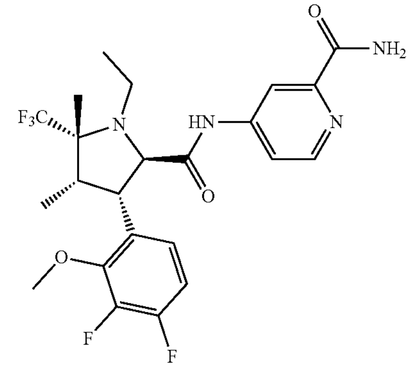

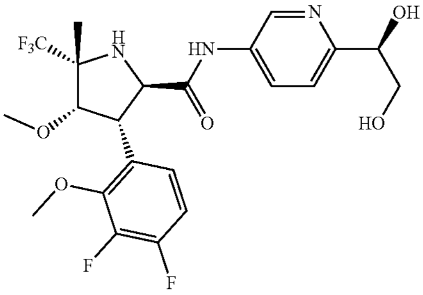

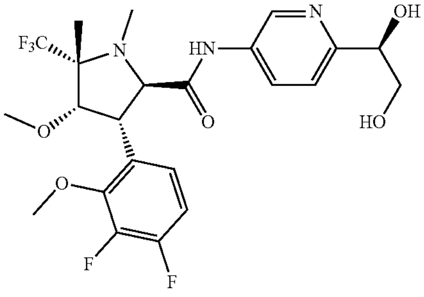

-continued
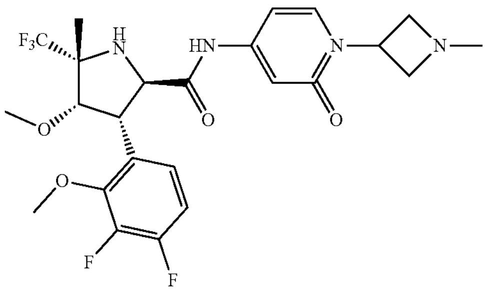
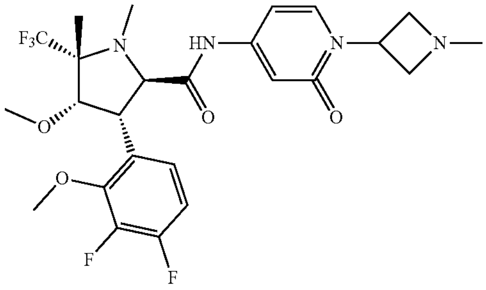
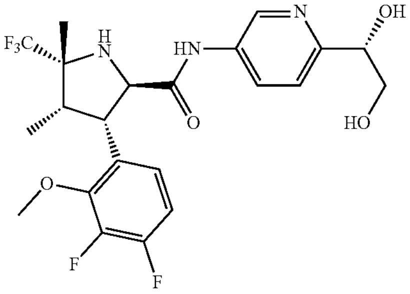
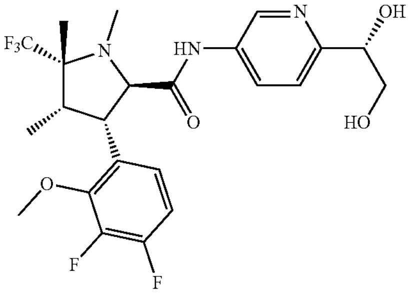
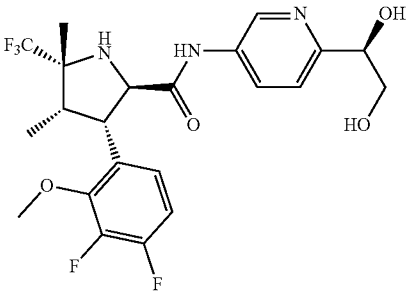
-continued
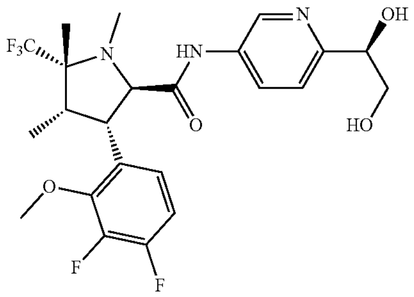
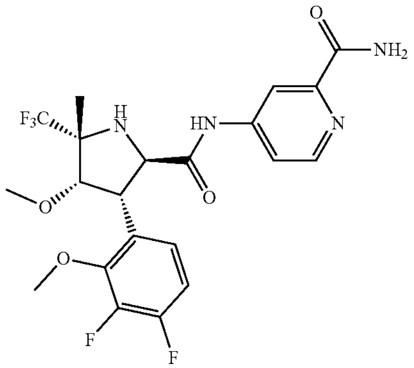
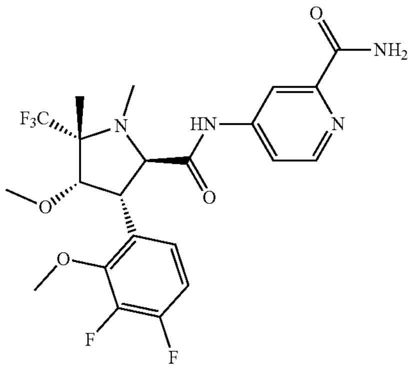
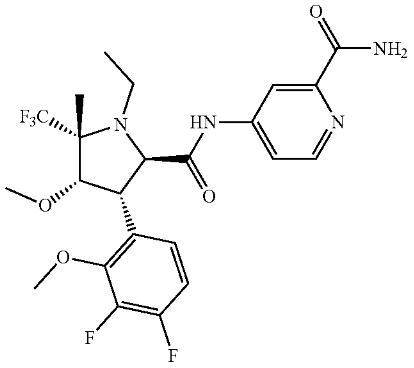
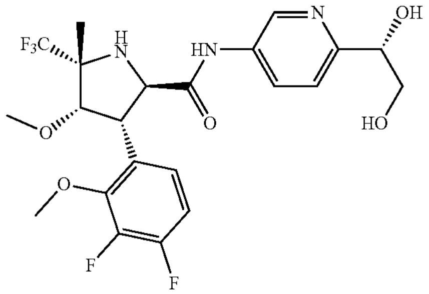

-continued
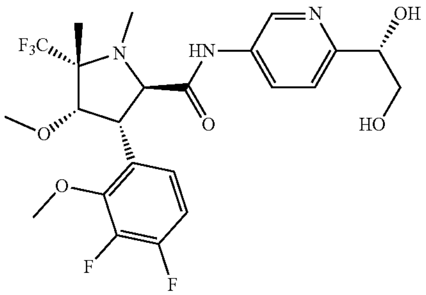
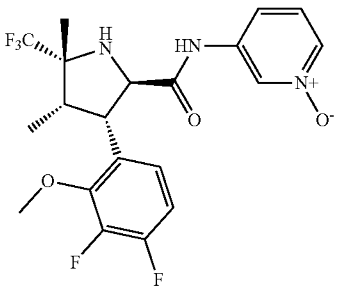
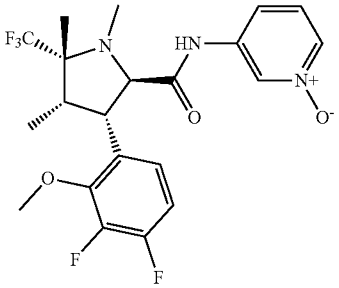
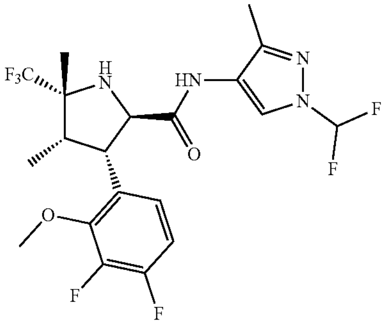
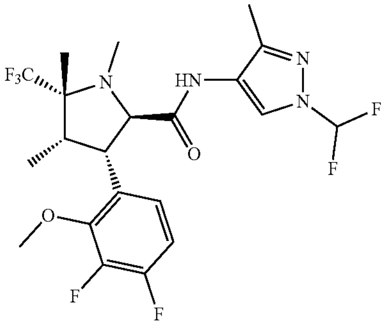
-continued
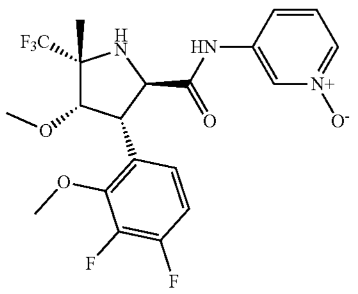
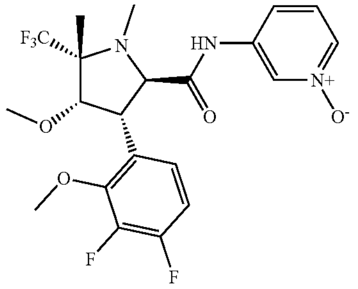
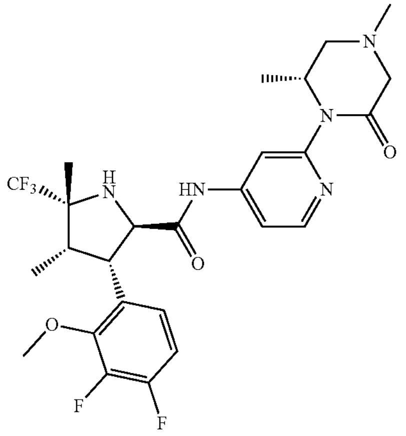
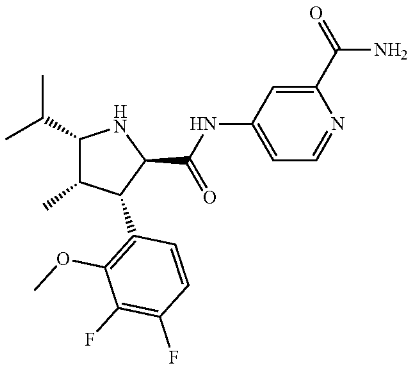

-continued
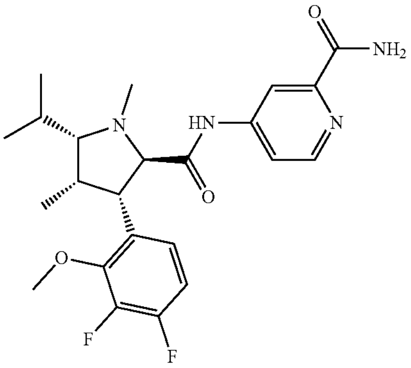
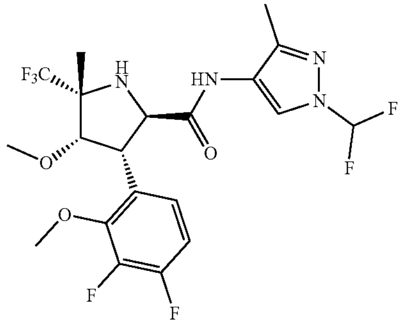
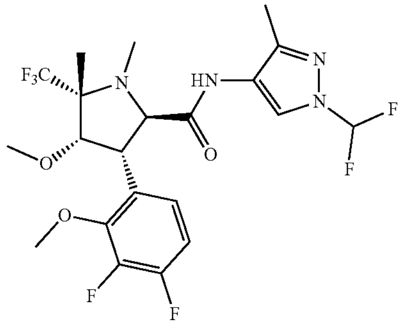
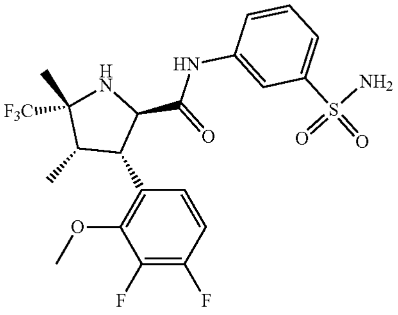
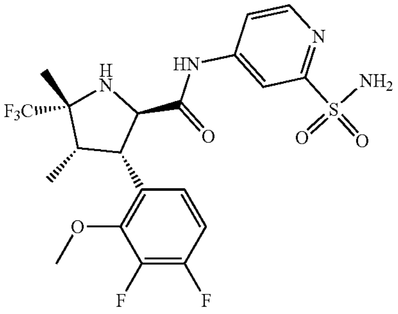
-continued
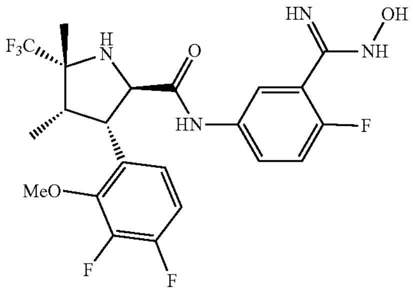
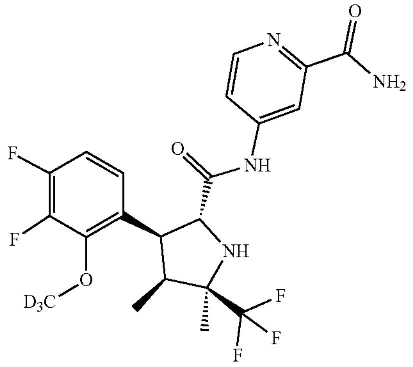
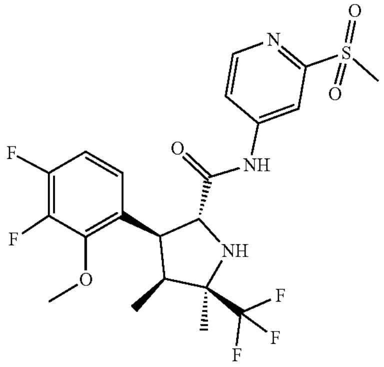
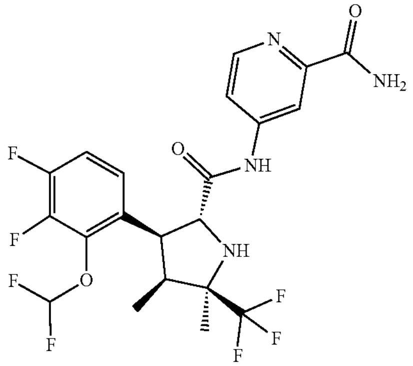
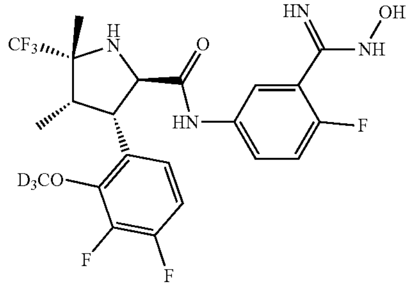

-continued
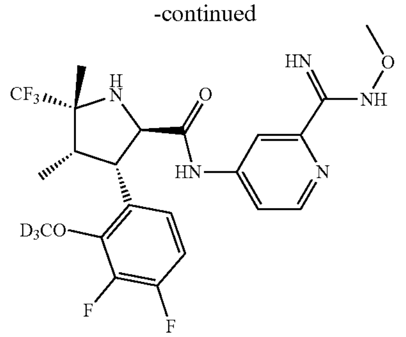
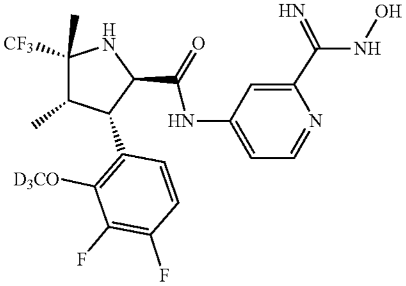
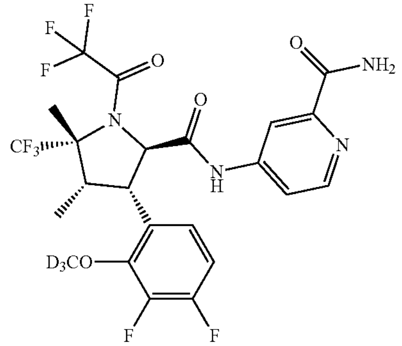
-continued
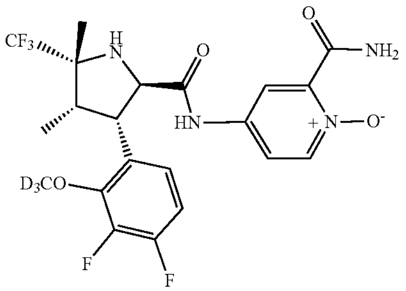
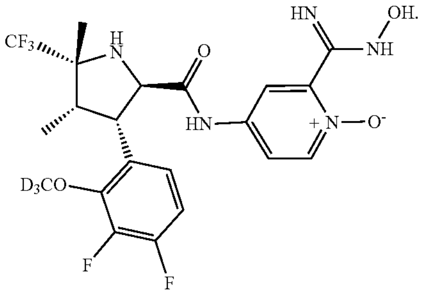
Embodiment 7. A method for the preparation of a compound represented by formula (I), or a stereoisomer, tautomer, deutero-derivative, or pharmaceutically acceptable salt thereof according to any one of Embodiments 1 to 6, wherein the method comprises the following steps:
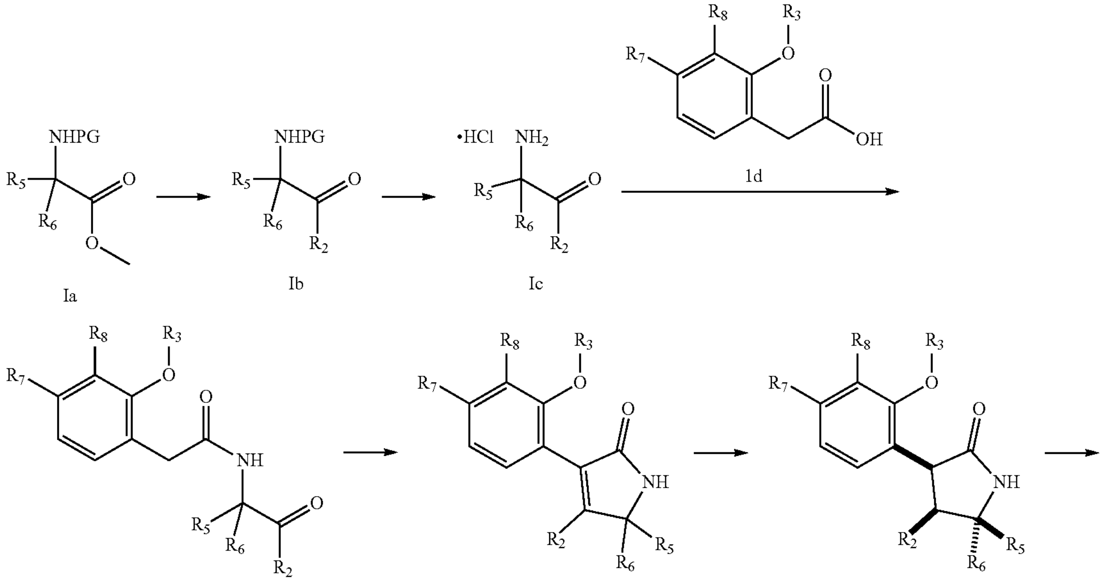
Ia Ib Ic
Ie If Ig -continued

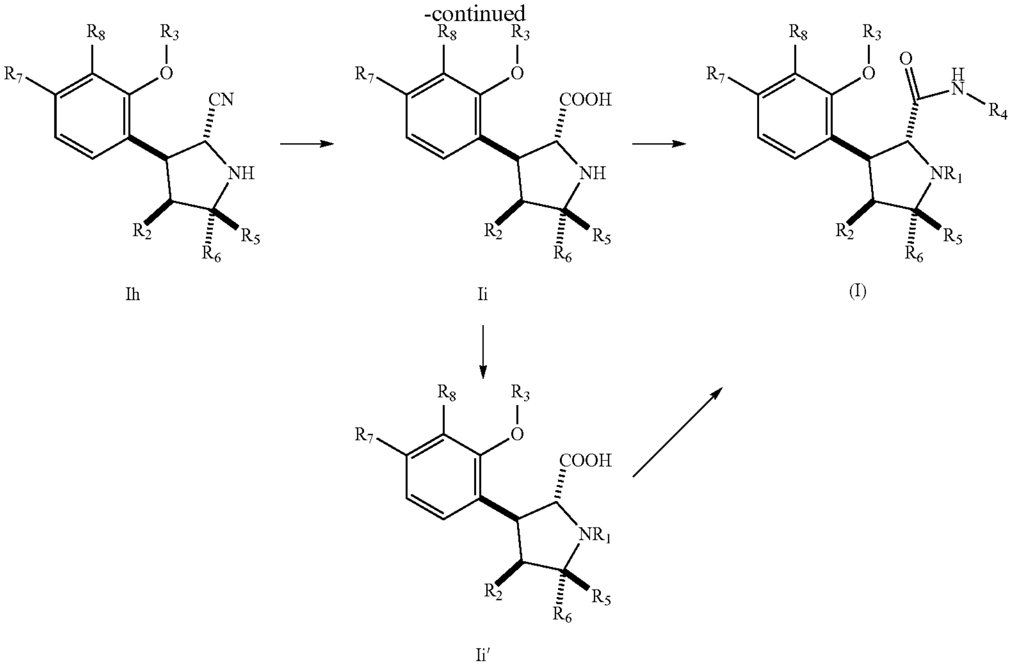

Ih Ii (I)

Ii'

Step 1: reacting compound Ia, in which the amino is protected by the amino-protecting group PG, and the PG is Boc or Cbz, with alkyl metal reagent, (e.g., alkyl lithium, alkyl Grignard reagent, trimethylsilylmethyl lithium and the like) by electrophilic addition reaction to obtain compound Ib;

Step 2: removing the amino-protecting group PG from compound Ib in a hydrogen atmosphere under a strong acidic condition (e.g. hydrochloric acid/dioxane solution) or in the presence of metallic palladium carbon to obtain compound Ic;

Step 3: condensing compound Ic with compound Id, phenylacetic acid derivatives, by amide condensation to obtain compound Ie;

Step 4: performing intramolecular cyclization dehydration reaction with compound Ie under alkaline condition (e.g., potassium hydroxide, sodium hydroxide, sodium hydrogen, etc.) to obtain compound If, Step 5: reducing the double bond in the ring with sodium borohydride and nickel chloride or palladium catalyzed hydrogenation conditions to obtain compound Ig;

Step 6: reducing lactam group in compound Ig to imine group with Schwartz reagent, then reacting with sodium cyanide or potassium cyanide by addition reaction to obtain pyrrolidine compound Ih;

Step 7: hydrolyzing the cyano in compound Ih to carboxyl group under strong acidic condition (e.g. hydrochloric acid/dioxane) or strong basic condition (e.g. aqueous potassium hydroxide) to obtain compound Ii;

Step 8: reacting compound Ii with aldehyde under palladium-catalyzed hydrogenation conditions or in the presence of a borohydride reducing agent to alkylate NH group in pyrrolidyl to obtain compound Ii';

Step 9: Reacting Ii or Ii' with an amine by amide condensation to obtain the final product compound I.

Embodiment 8. Use of a compound represented by formula (I), or a stereoisomer, tautomer, deutero-derivative, or pharmaceutically acceptable salt thereof according to any one of Embodiments 1 to 6 as a Nav1.8 inhibitor.

Embodiment 9. A pharmaceutical composition, comprising a therapeutically effective amount of a compound represented by formula (I), or a stereoisomer, tautomer, deutero-derivative, or pharmaceutically acceptable salt thereof according to any one of Embodiments 1 to 6 as an active ingredient, and a pharmaceutically acceptable excipient.

Embodiment 10. Use of a compound represented by formula (I), or a stereoisomer, tautomer, deutero-derivative, or pharmaceutically acceptable salt thereof according to any one of claims 1 to 6, or the pharmaceutical composition according to Embodiment 9, in the preparation of a drug for the treatment of acute pain and chronic pain.

Embodiment 11. A method for treating chronic pain, comprising a step of providing to a subject a therapeutically effective amount of a compound represented by formula (I), or a stereoisomer, tautomer, deutero-derivative, or pharmaceutically acceptable salt thereof according to any one of Embodiments 1 to 6 or the pharmaceutical composition according to Embodiment 9.

The above description is only a specific embodiment of the present invention, but the scope of protection of the present invention is not limited thereto, and any person skilled in the art who is familiar with the technical field of the present invention can readily think of variations or substitutions within the technical scope of the present invention as disclosed herein, which shall be covered within the scope of protection of the present invention. Therefore, the scope of protection of the present invention shall be subject to the scope of protection of the claims.

The invention claimed is:

1. A compound or a stereoisomer, tautomer, deutero-derivative, or pharmaceutically acceptable salt thereof, wherein the compound is:

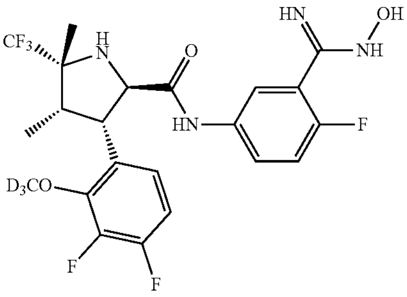
,
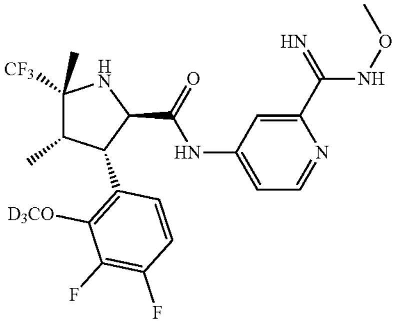
,
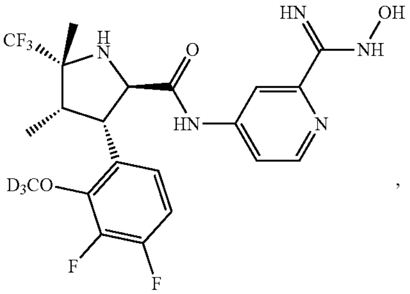
,
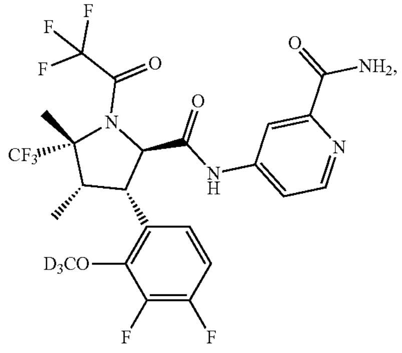
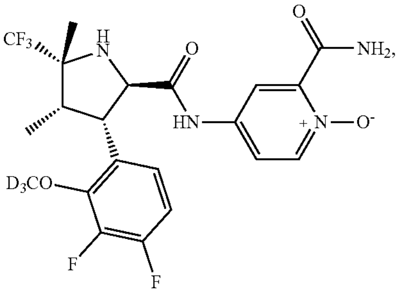
-continued
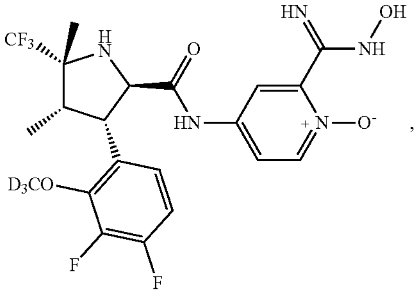
, or
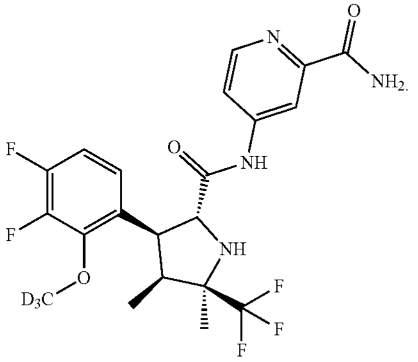
2. The compound or stereoisomer, tautomer, deutero-derivative, or pharmaceutically a acceptable salt thereof according to claim 1, wherein the compound is
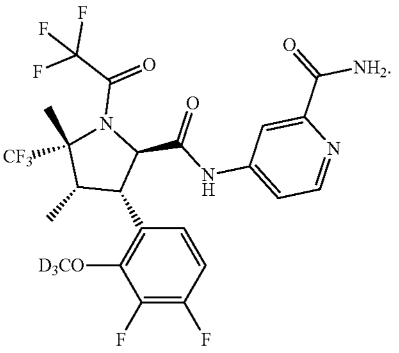
3. The compound or stereoisomer, tautomer, deutero-derivative, or pharmaceutically a acceptable salt thereof according to claim 1, wherein the compound is
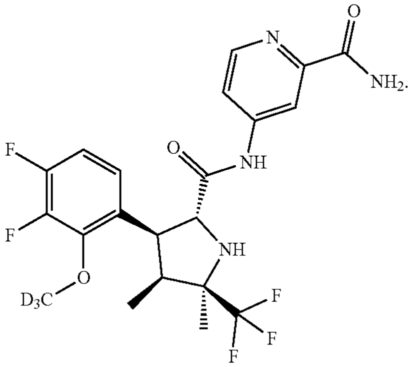 [SMILES: [2H]C([2H])([2H])Oc1c([C@H]2[C@H](C(=O)Nc3ccnc(C(N)=O)c3)N[C@@](C)(C(F)(F)F)[C@H]2C)ccc(F)c1F]

4. A pharmaceutical composition, comprising a therapeutically effective amount of the compound or stereoisomer, tautomer, deutero-derivative, or pharmaceutically acceptable salt thereof according to claim 1, and a pharmaceutically acceptable excipient.

5. A method for treating chronic pain, comprising administering a therapeutically effective amount of the compound or stereoisomer, tautomer, deutero-derivative, or pharmaceutically acceptable salt thereof according to claim 1 to a subject in need thereof.

6. The method of claim 5, wherein the compound is:

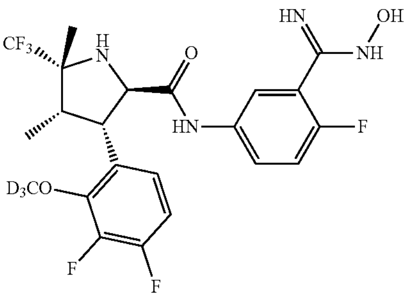

,

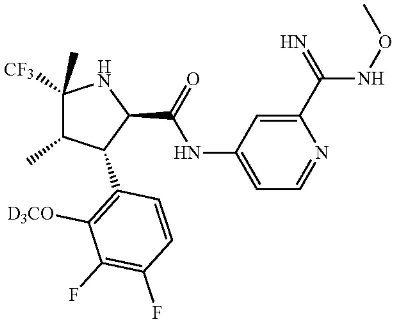

,

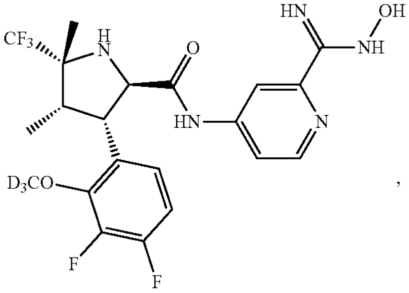

,

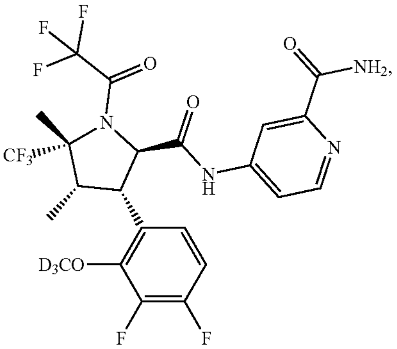

-continued

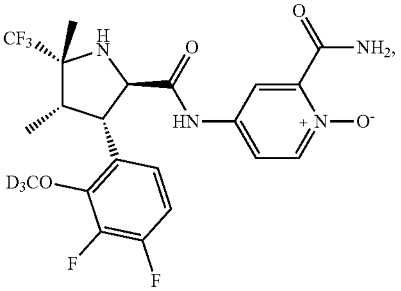

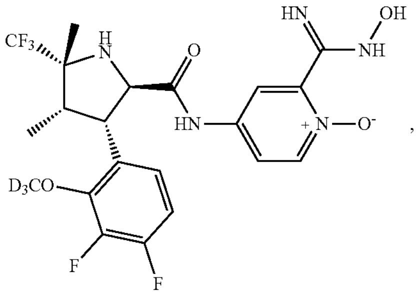

, or

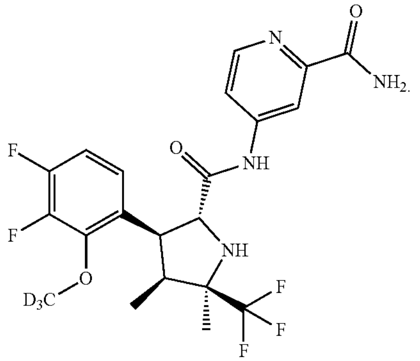

7. The method of claim 5, wherein the compound is

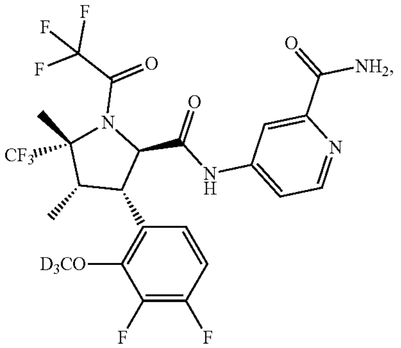

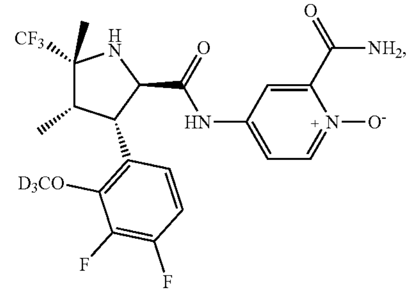

or

-continued
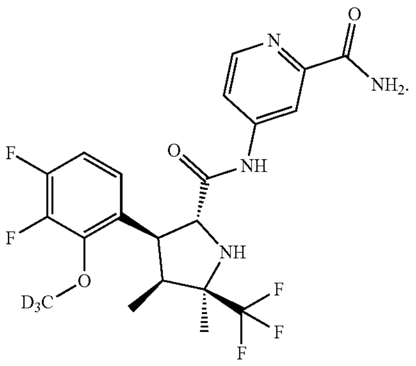
8. The method of claim 5, wherein the compound is
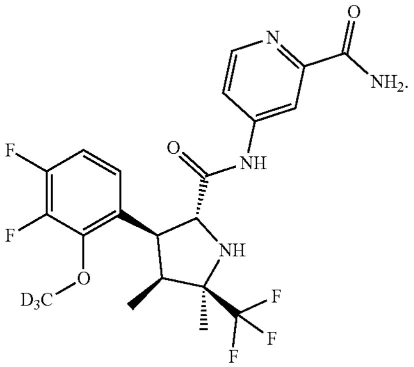 [SMILES: [2H]C([2H])([2H])Oc1c([C@H]2[C@H](C(=O)Nc3ccnc(C(N)=O)c3)N[C@@](C)(C(F)(F)F)[C@H]2C)ccc(F)c1F]
* * * * *